US012661402B2

(12) United States Patent
Lee et al.

(10) Patent No.: US 12,661,402 B2
(45) Date of Patent: Jun. 23, 2026

(54) POLYPEPTIDE SPECIFIC FOR MUCIN 1 AND USE THEREOF

(71) Applicant: LG CHEM, LTD., Seoul (KR)

(72) Inventors: Ji Hyun Lee, Daejeon (KR); Hae Youn Lee, Daejeon (KR); Yoon Aa Choi, Daejeon (KR); Dae Gwan Yi, Daejeon (KR); Jungwon Choi, Daejeon (KR); Areum Park, Daejeon (KR); Saem Jung, Daejeon (KR); Eu Rim Song, Daejeon (KR); Kyubong Na, Daejeon (KR); Min Jeong Park, Daejeon (KR); Eun Ji Jeun, Daejeon (KR); Kyuhong Choe, Daejeon (KR); Hyoju Yi, Daejeon (KR); Hee Jung Yang, Daejeon (KR); Sung Woong Jang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 394 days.

(21) Appl. No.: 18/259,205

(22) PCT Filed: Dec. 24, 2021

(86) PCT No.: PCT/KR2021/019790
§ 371 (c)(1),
(2) Date: Jun. 23, 2023

(87) PCT Pub. No.: WO2022/139537
PCT Pub. Date: Jun. 30, 2022

(65) Prior Publication Data
US 2025/0281533 A1 Sep. 11, 2025

(30) Foreign Application Priority Data

Dec. 24, 2020 (KR) ........................ 10-2020-0183768
Oct. 15, 2021 (KR) ........................ 10-2021-0137757

(51) Int. Cl.
| | |
|---|---|
| *A61K 40/42* | (2025.01) |
| *A61K 35/17* | (2015.01) |
| *A61K 40/11* | (2025.01) |
| *A61K 40/31* | (2025.01) |
| *A61P 35/00* | (2006.01) |
| *C07K 14/705* | (2006.01) |
| *C07K 16/30* | (2006.01) |
| *C12N 5/0783* | (2010.01) |
| *C12N 15/86* | (2006.01) |

(52) U.S. Cl.
CPC .......... *A61K 40/4257* (2025.01); *A61K 35/17* (2013.01); *A61K 40/11* (2025.01); *A61K 40/31* (2025.01); *A61P 35/00* (2018.01); *C07K 14/7051* (2013.01); *C07K 14/70517* (2013.01); *C07K 14/70521* (2013.01); *C07K 16/3092* (2013.01); *C12N 5/0636* (2013.01); *C12N 15/86* (2013.01); *A61K 2239/13* (2023.05); *A61K 2239/17* (2023.05); *A61K 2239/21*

(2023.05); *A61K 2239/31* (2023.05); *A61K 2239/38* (2023.05); *A61K 2239/49* (2023.05); *A61K 2239/54* (2023.05); *C07K 2317/53* (2013.01); *C07K 2317/565* (2013.01); *C07K 2317/622* (2013.01); *C07K 2319/02* (2013.01); *C07K 2319/03* (2013.01); *C12N 2510/00* (2013.01); *C12N 2740/15043* (2013.01)

(58) Field of Classification Search
CPC ..... A61K 40/4257; A61K 40/31; A61P 35/00; C07K 14/7051; C12N 5/0636; C12N 15/86
See application file for complete search history.

(56) References Cited

U.S. PATENT DOCUMENTS

| | | |
|---|---|---|
| 2016/0340442 A1 | 11/2016 | Kufe et al. |
| 2017/0198056 A1 | 7/2017 | Nishimura et al. |
| 2017/0204191 A1 | 7/2017 | Bamdad et al. |
| 2019/0328784 A1 | 10/2019 | Ostertag et al. |
| 2020/0024361 A1 | 1/2020 | Moon et al. |
| 2020/0061216 A1 | 2/2020 | Mukherjee |
| 2020/0261603 A1 | 8/2020 | Morinaka et al. |

FOREIGN PATENT DOCUMENTS

| | | |
|---|---|---|
| EP | 1383802 A2 | 1/2004 |
| KR | 10-2016-0132012 A | 11/2016 |
| KR | 10-2020-0079226 A | 7/2020 |
| RU | 2016144178 A | 5/2018 |
| WO | 01-075110 A2 | 10/2001 |

(Continued)

OTHER PUBLICATIONS

Bose et al., "Potential of Anti-MUCI Antibodies as a Targeted Therapy for Gastrointestinal Cancers" vaccines, 2020, 8, 659, 21 pages.

(Continued)

*Primary Examiner* — Prema M Mertz

(74) *Attorney, Agent, or Firm* — ROTHWELL, FIGG, ERNST & MANBECK, P.C.

(57) ABSTRACT

The present invention relates to a polypeptide binding to mucin 1, an isolated polynucleotide encoding same, a vector carrying the polynucleotide, and a cell including the vector. In addition, the present invention relates to a chimeric antigen receptor including the polypeptide binding to mucin 1, an isolated polynucleotide encoding the chimeric antigen receptor, a vector carrying the polynucleotide, an immune cell expressing the chimeric antigen receptor, a composition comprising same for treatment of cancer, and a method for treatment of cancer.

31 Claims, 17 Drawing Sheets

Specification includes a Sequence Listing.

(56)　　　　　　References Cited

FOREIGN PATENT DOCUMENTS

| WO | 02079429 A2 | 10/2002 |
| WO | 2015-009740 A2 | 1/2015 |
| WO | 2018-174544 A2 | 9/2018 |

OTHER PUBLICATIONS

European Search Report issued for European Patent Application No. 21911602.7 on Nov. 12, 2024, 15 pages.

Abate-Daga et al., "CAR models: next-generation CAR modifications for enhanced T-cell function", Mol Ther Oncolytics, 2016, 3:16014, 7 pages.

Partial Supplementary European Search Report dated Jul. 30, 2024, of the corresponding European Patent Application No. 21911602.7, 16 pages.

International Search Report issued for International Application No. PCT/KR2021/019790 on Jul. 12, 2022, 6 pages.

Wu et al., "A Novel Monoclonal Antibody Targets Mucin1 and Attenuates Growth in Pancreatic Cancer Model", International Journal of Molecular Sciences, 2018, 19(7): 2004, 14 pages.

NCBI, GenBank Accession No. BAA82041.1, single chain Fv antibody, partial, synthetic construct, 2016, 2 pages.

【FIG. 1】
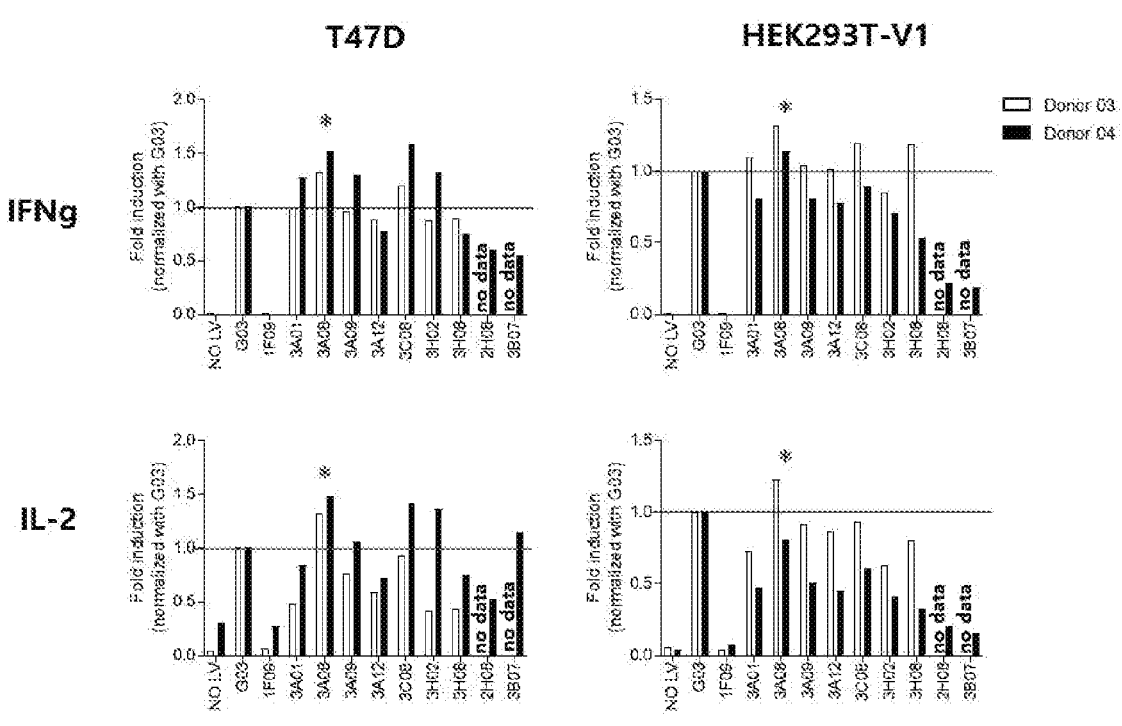

【FIG. 2】
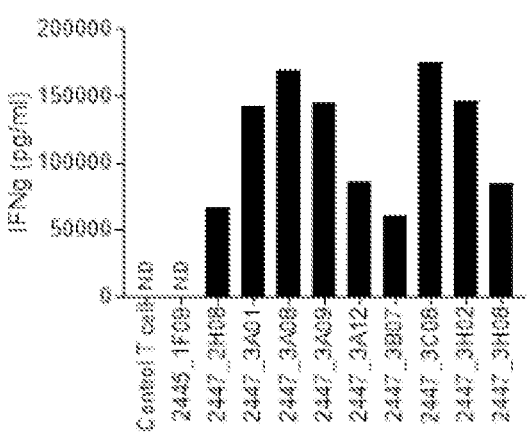 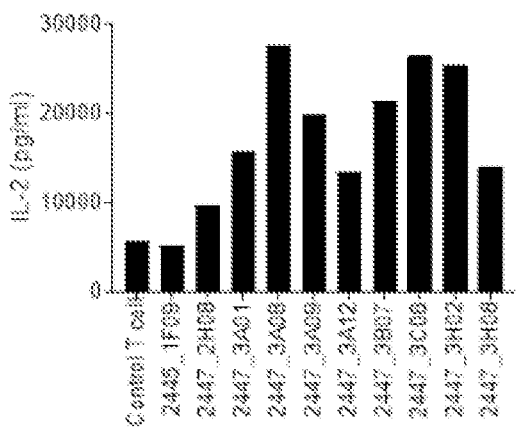
【FIG. 3】
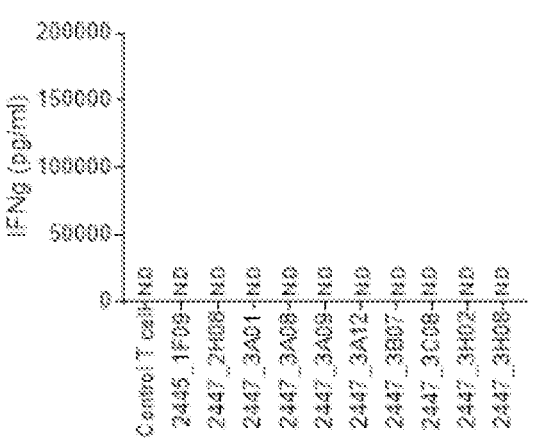 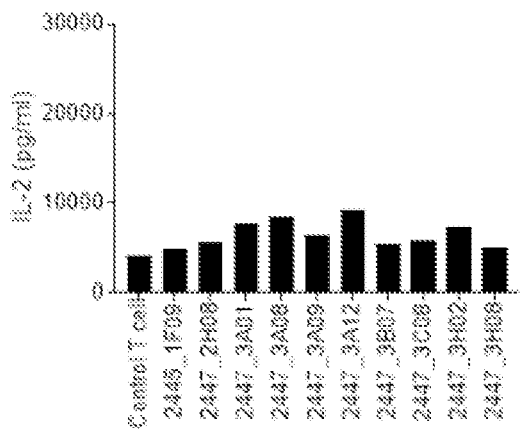

【FIG. 4】
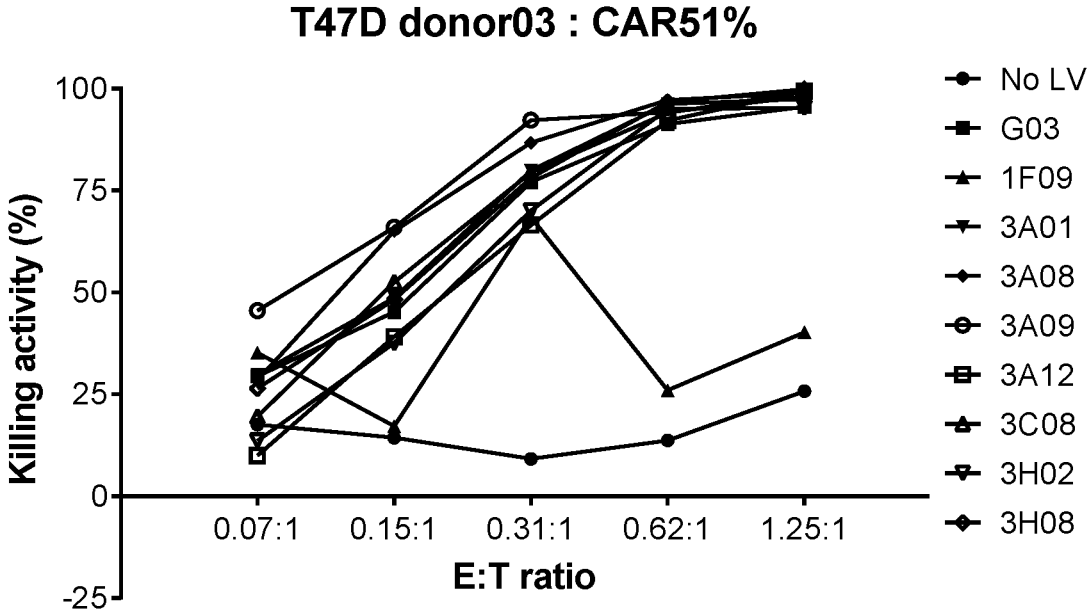

【FIG. 5】
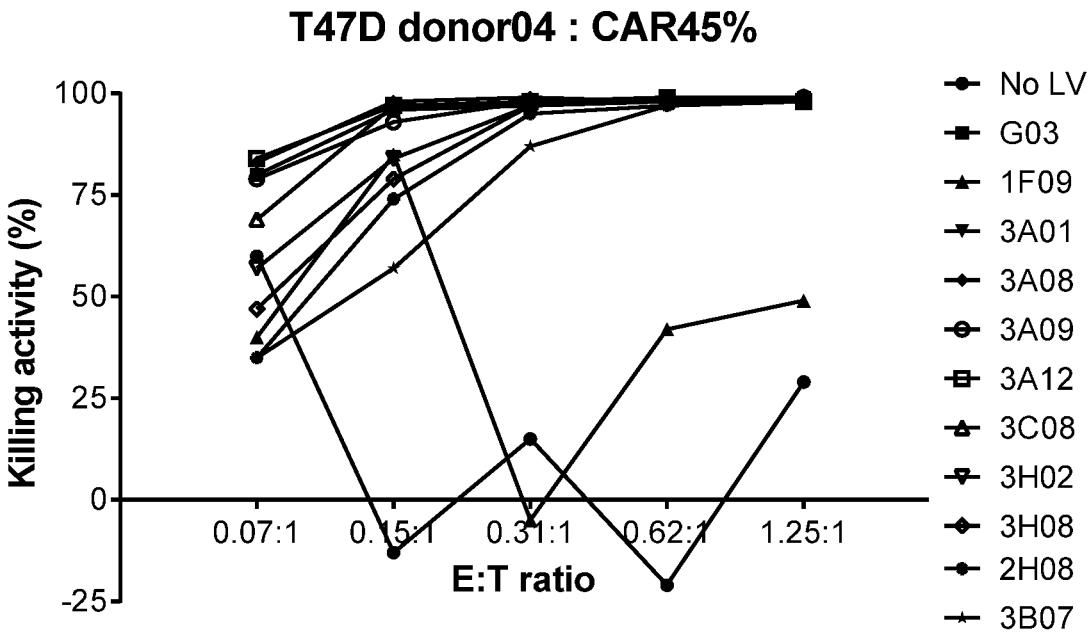

【FIG. 6】
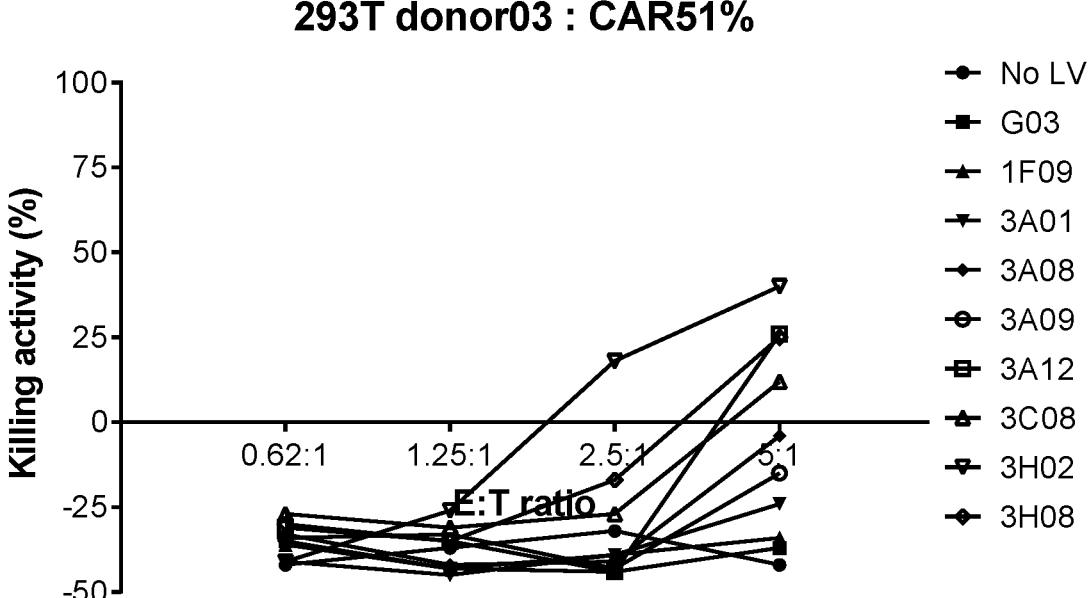

【FIG. 7】
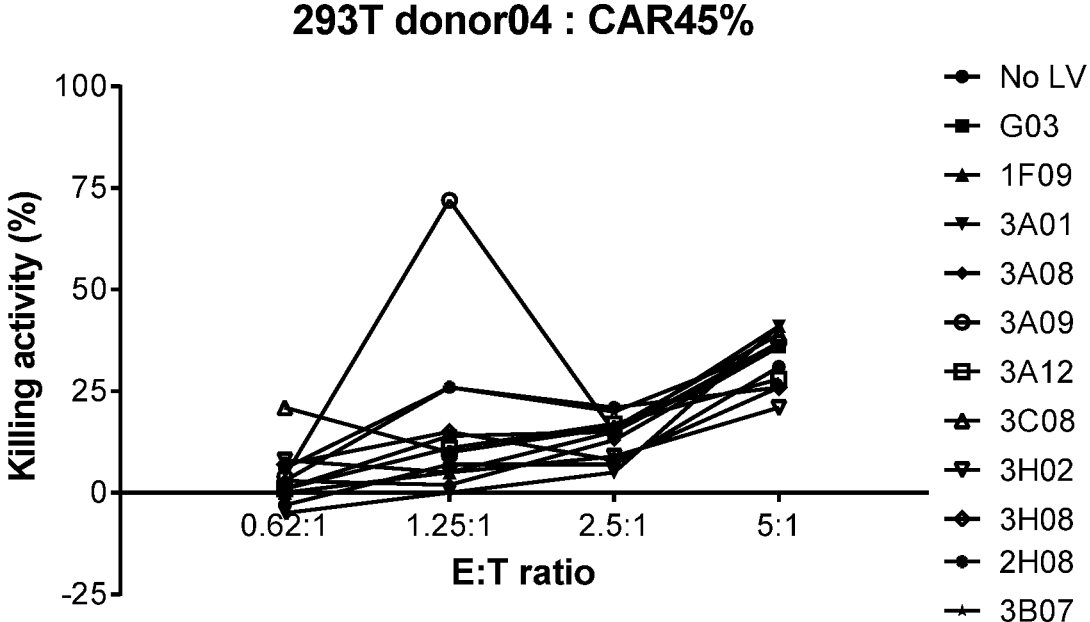

【FIG. 8】
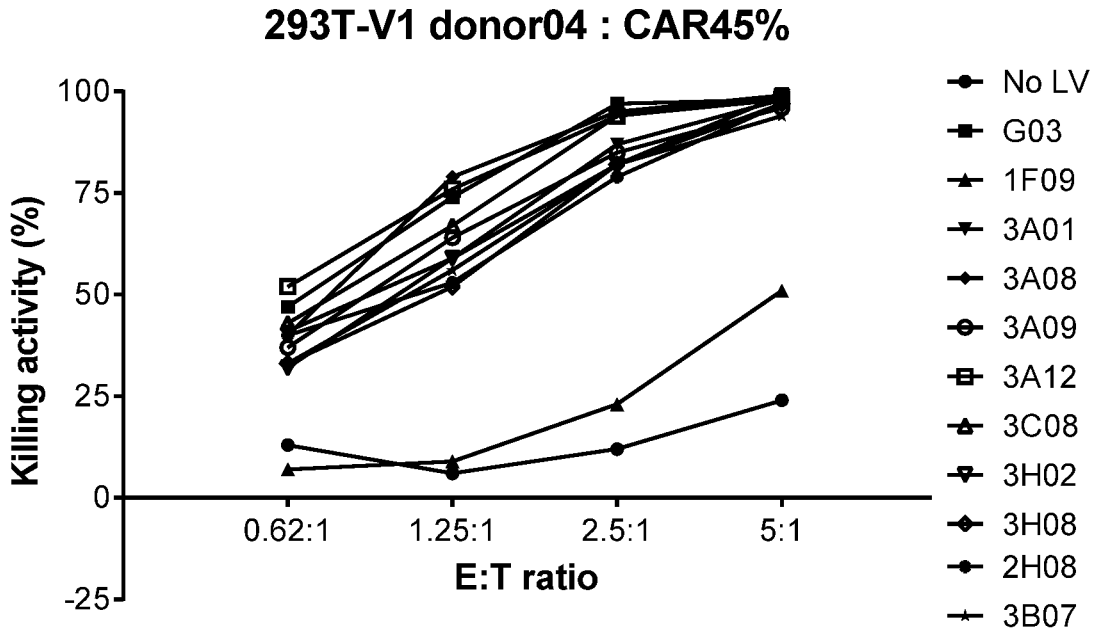

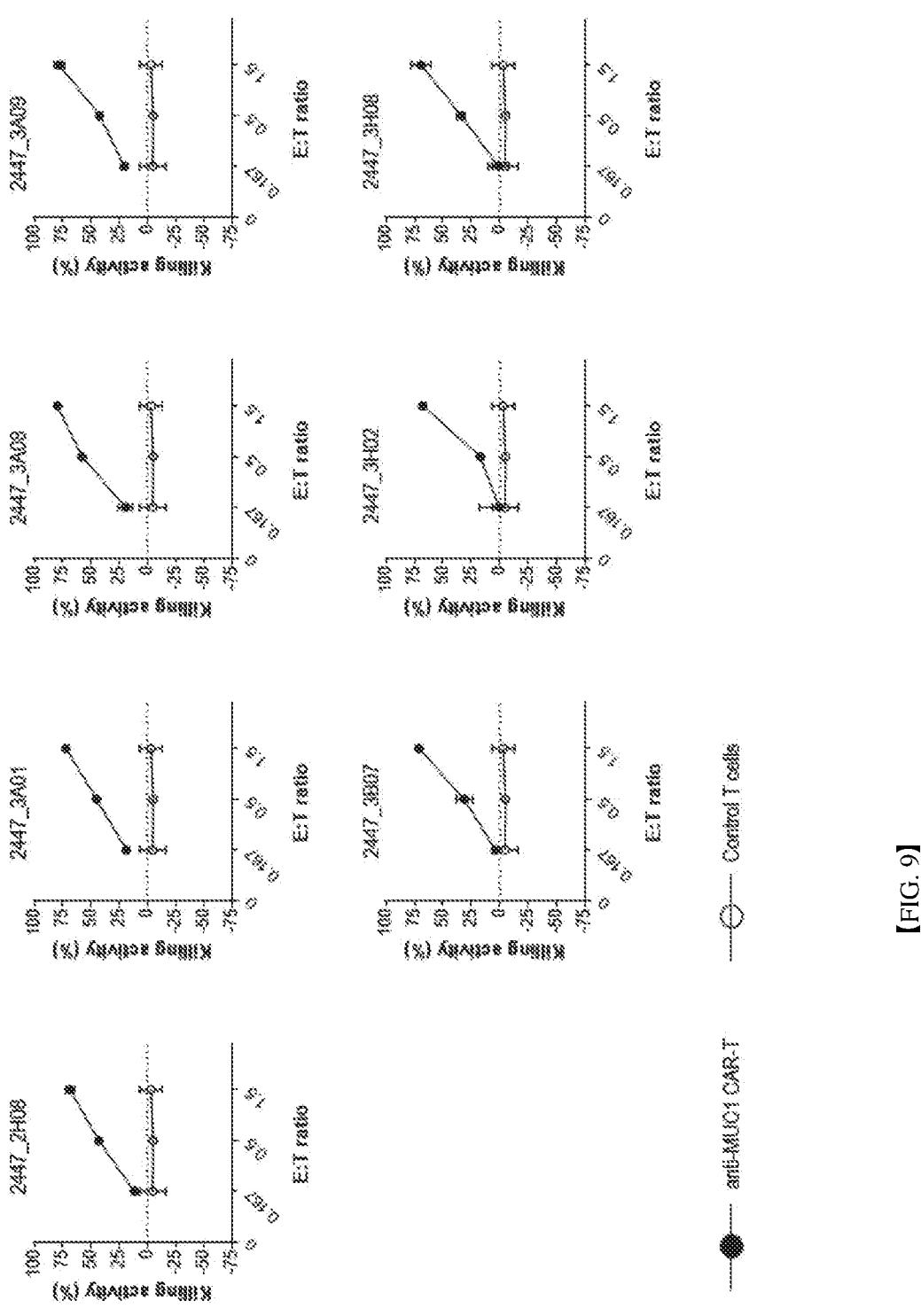
[FIG. 9]

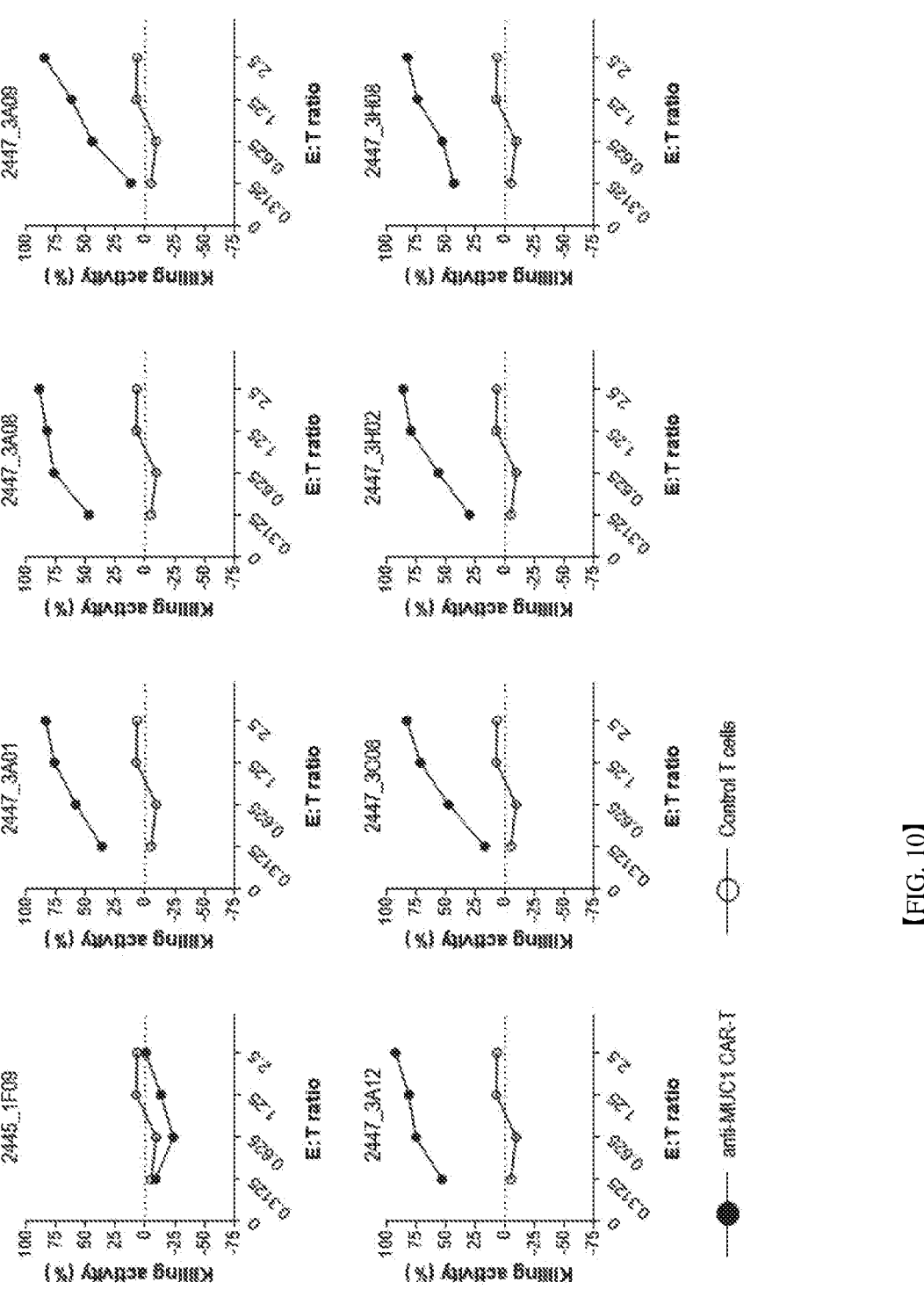
[FIG. 10]

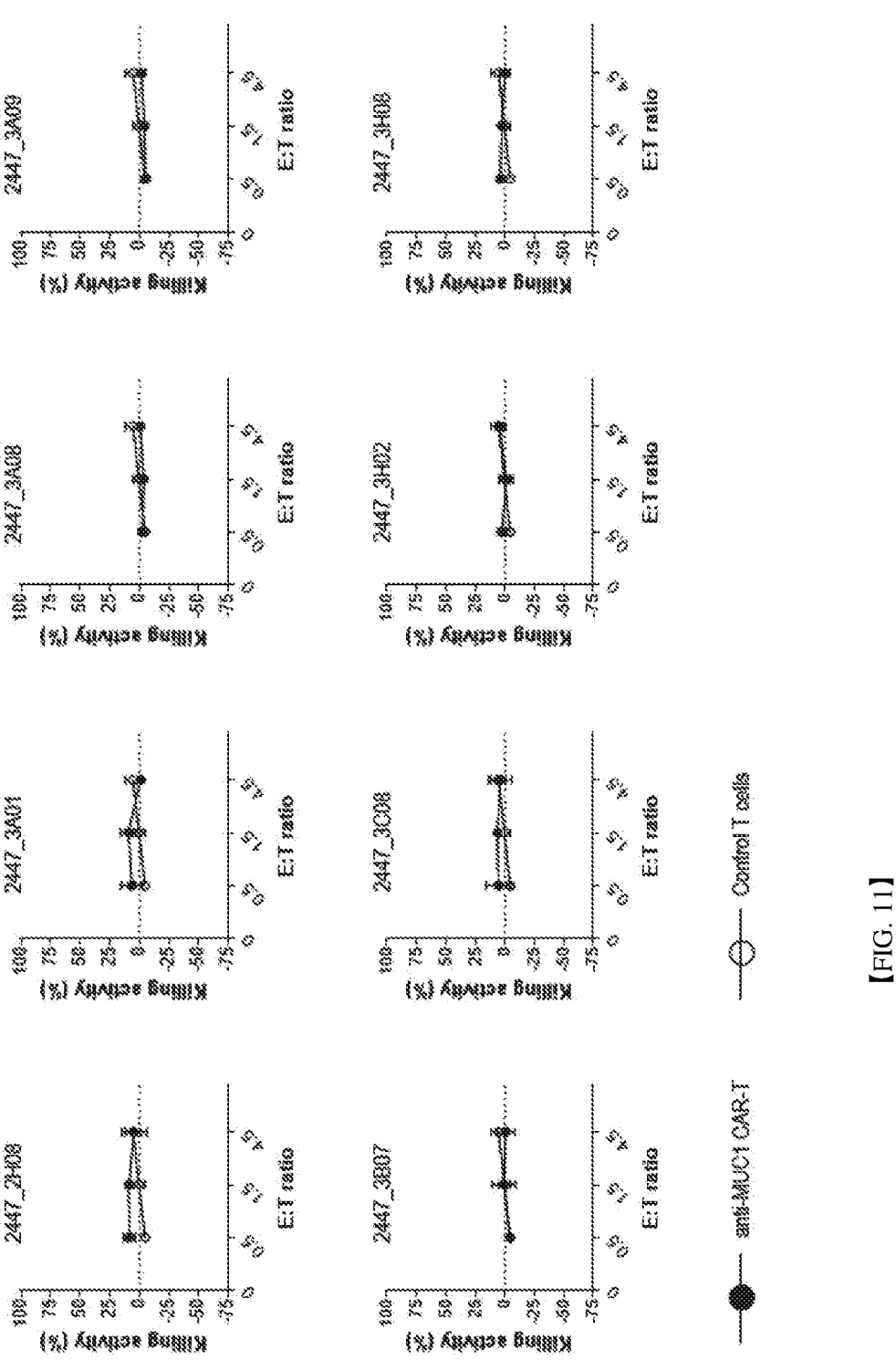
[FIG. 11]

【FIG. 12】
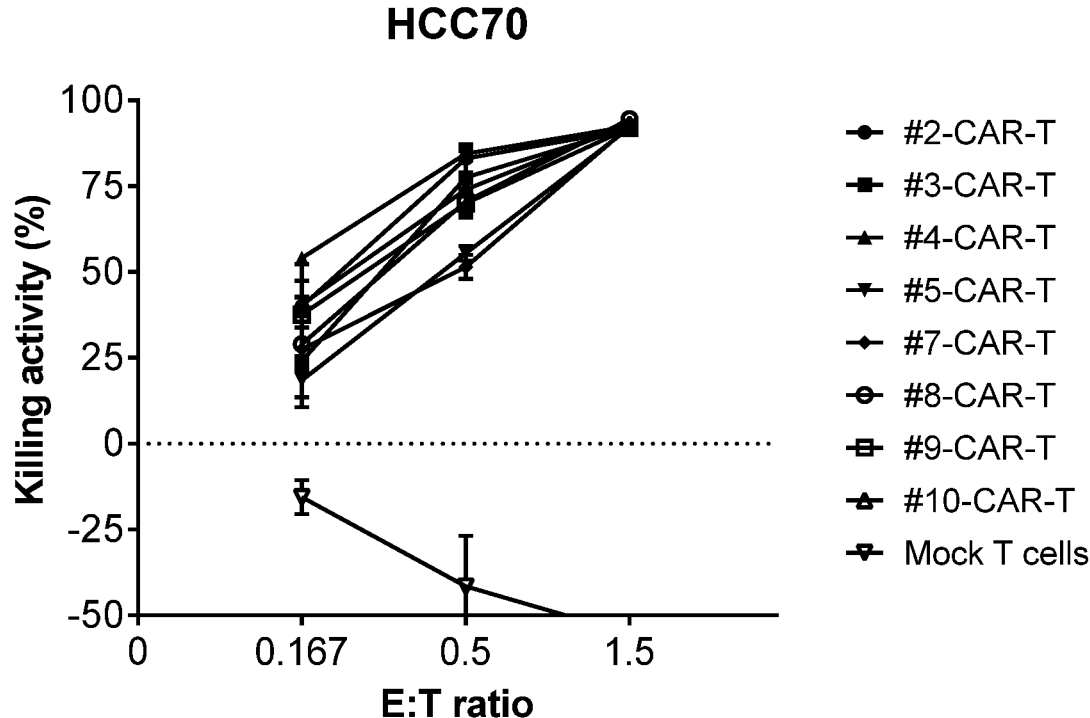

【FIG. 13】
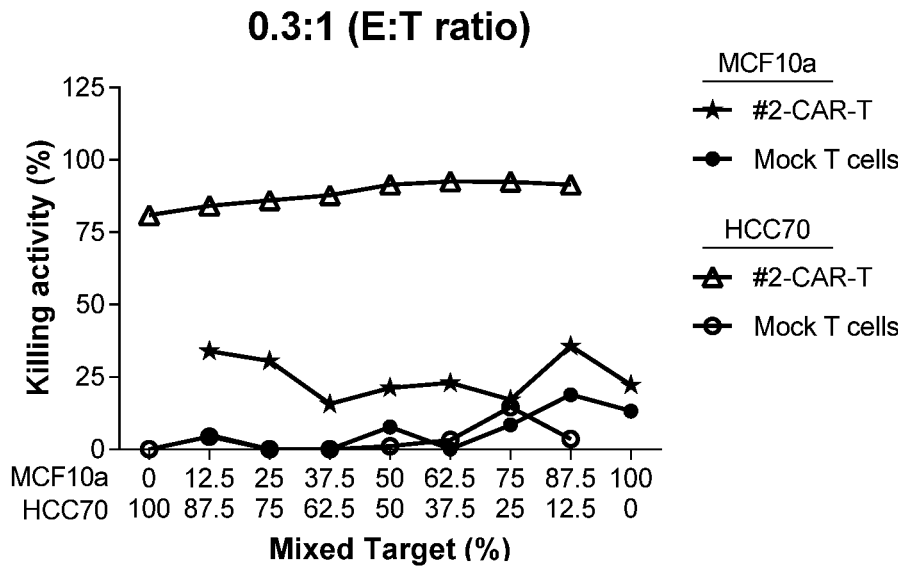

【FIG. 14】
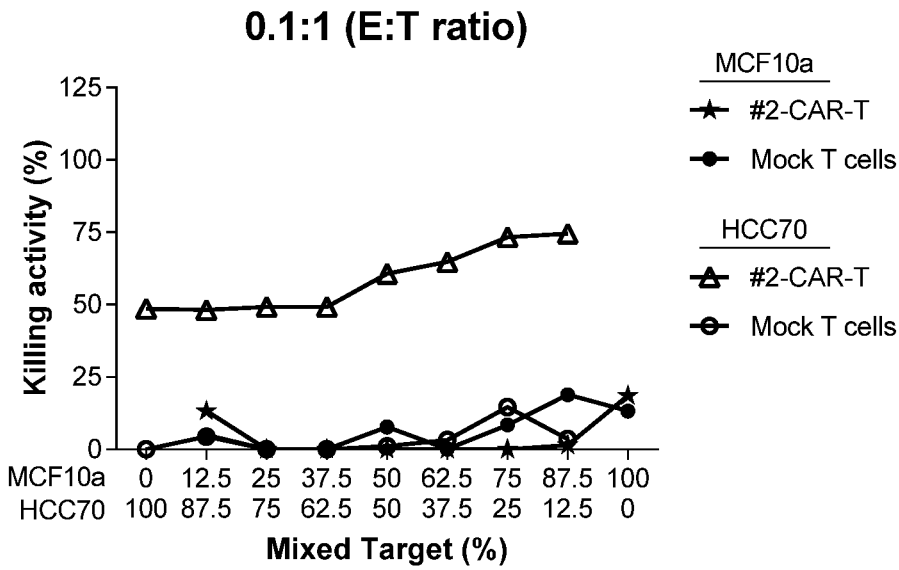

【FIG. 15】
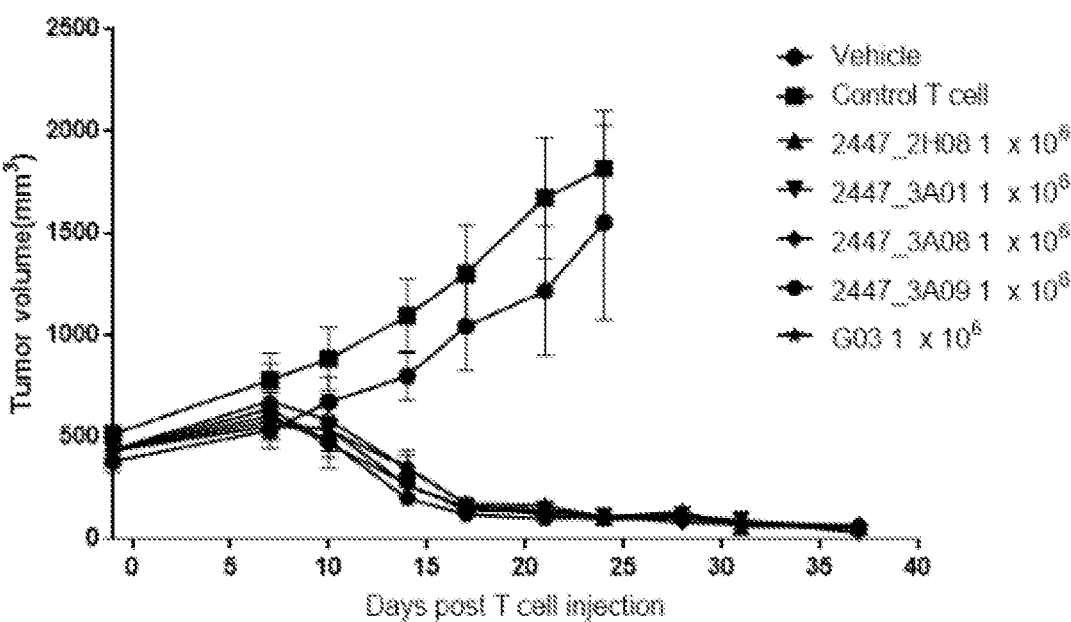

【FIG. 16】
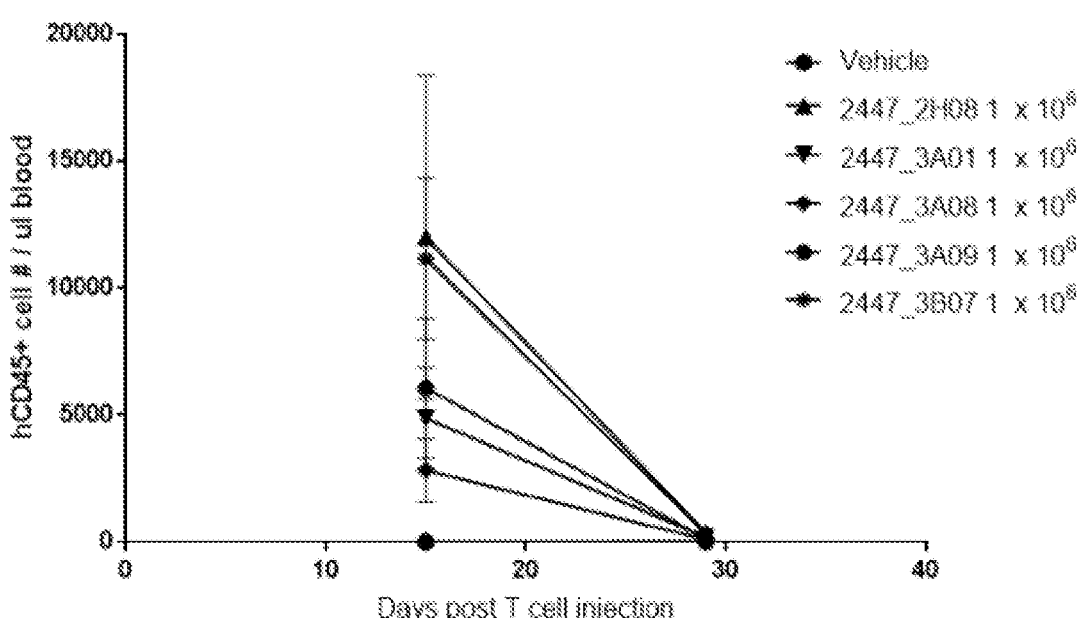

【FIG. 17】
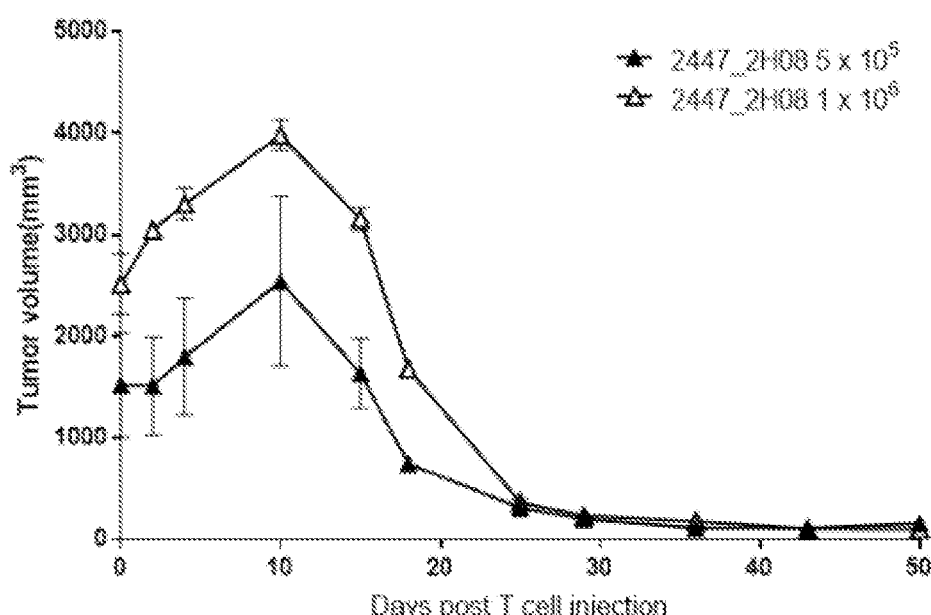

【FIG. 18】
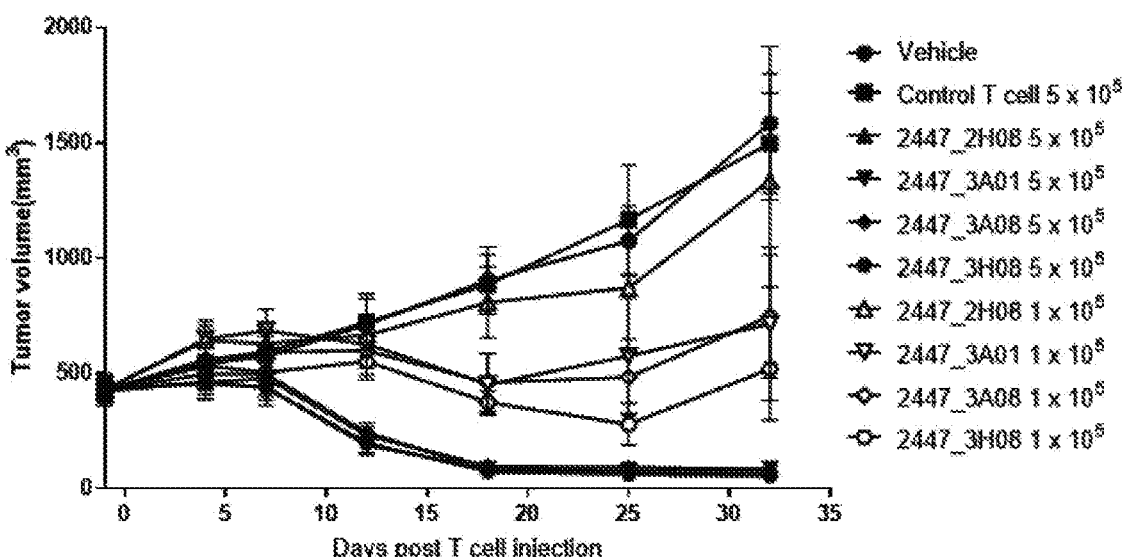
【FIG. 19】
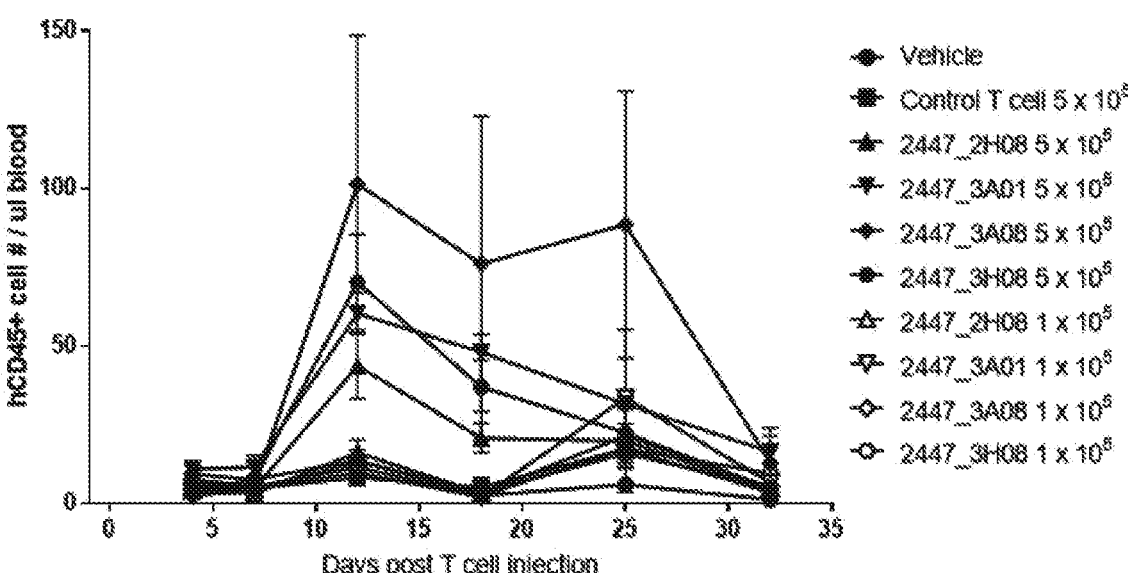

POLYPEPTIDE SPECIFIC FOR MUCIN 1 AND USE THEREOF

TECHNICAL FIELD

Cross-Reference to Related Application

This application is a 35 U.S.C. 371 National Phase Entry Application from PCT/KR2021/019790 filed on Dec. 24, 2021, which claims priority from, Korean Patent Application Nos. 10-2020-0183768 and 10-2021-0137757, filed on Dec. 24, 2020 and Oct. 15, 2021, respectively, the disclosures of which are hereby incorporated by reference herein in their entirety.

The present application includes a Sequence Listing filed in electronic format. The Sequence Listing is entitled "Updated-Revised-Opp20230750US_Sequence listing.txt" created on Jan. 9, 2026, and is 77,824 bytes in size. The information in the electronic format of the Sequence Listing is part of the present application and is incorporated herein by reference in its entirety.

TECHNICAL FIELD

Provided is a polypeptide binding to mucin1, an isolated polynucleotide encoding the same, a vector comprising the polynucleotide, and a cell comprising the vector. Further, provided is a chimeric antigen receptor comprising the polypeptide binding to mucin1, an isolated polynucleotide encoding the chimeric antigen receptor, a vector comprising the polynucleotide, an immune cell expressing the chimeric antigen receptor, and a composition for and a method of treating cancer, each comprising the same.

BACKGROUND

Mucin1 is a membrane-bound glycoprotein present in epithelial cells of almost all organs in the body. Mucin1 is a heterodimeric protein formed by a non-covalent interaction of an N-terminal subunit (MUC1-N) and a C-terminal subunit (MUC1-C). MUC1-C forms an extracellular domain, a transmembrane domain, and a cytoplasmic tail. MUC1-N repeatedly includes tandem repeats (TRs) containing 20 amino acids (HGVTSAPDTRPAPGSTAPPA) (SEQ ID NO: 121), including glycosylation sites, and interacts with the extracellular domain of MUC1-C and continues to be linked with MUC1-C.

In normal epithelial cells, mucin1 is expressed at a low level, and its expression is limited to the apical membranes of the epithelium. However, mucin1 is known to be overexpressed in solid cancer such as breast cancer, lung cancer, colorectal cancer, skin cancer, thyroid cancer, gastric cancer, pancreatic cancer, kidney cancer, ovarian cancer, cervical cancer, etc., and known to be randomly expressed on the entire cell surface and abnormally glycosylated. Therefore, mucin1 is known to be useful as a target molecule for detecting cancer lesions or as a target molecule for treating cancer.

BRIEF SUMMARY

Technical Problem

Currently, there are many reports of anti-MUC1 antibodies for cancer treatment. However, anticancer therapy using antibodies is applicable only to cancer cells that have antigens specifically recognized by the antibodies, duration of the effect is short, and resistance often occurs during prolonged use thereof. Accordingly, there is a demand for developing a technology capable of continuously exerting strong anticancer effects on various cancers by activating the immune system in the body.

Technical Solution

There is provided a polypeptide binding to mucin1.

An embodiment provides an isolated polynucleotide encoding the mucin1-binding polypeptide.

Other embodiment provides a vector comprising the polynucleotide encoding the mucin1-binding polypeptide.

Other embodiment provides a cell comprising the vector comprising the polynucleotide encoding the mucin1-binding polypeptide.

Other embodiment provides a chimeric antigen receptor comprising the mucin1-binding polypeptide.

Other embodiment provides an isolated polynucleotide encoding the chimeric antigen receptor.

Other embodiment provides a vector comprising the polynucleotide encoding the chimeric antigen receptor.

Other embodiment provides an immune cell expressing the chimeric antigen receptor, or comprising the polynucleotide encoding the chimeric antigen receptor.

Other embodiment provides a composition for treating cancer, the composition comprising the mucin1-binding polypeptide; the isolated polynucleotide encoding the mucin1-binding polypeptide; the vector comprising the polynucleotide encoding the mucin1-binding polypeptide; the cell comprising the polynucleotide encoding the mucin1-binding polypeptide; the chimeric antigen receptor comprising the mucin1-binding polypeptide; the isolated polynucleotide encoding the chimeric antigen receptor; the vector comprising the polynucleotide encoding the chimeric antigen receptor; or the immune cell comprising the polynucleotide encoding the chimeric antigen receptor, or expressing the chimeric antigen receptor.

BRIEF DESCRIPTION OF DRAWINGS

FIG. 1 shows results of analyzing cytokine secretion for evaluating responses of CAR-T cells according to one exemplary embodiment of the present disclosure, which were prepared using donor 03- and donor 04-derived T cells, against MUC1-positive tumor cells (T47D, HEK293T-V1);

FIG. 2 shows results of analyzing cytokine secretion for evaluating responses of CAR-T cells according to one exemplary embodiment of the present disclosure, which were prepared using donor 06-derived T cells, against MUC1-positive tumor cells (T47D);

FIG. 3 shows results of analyzing cytokine secretion for evaluating responses of CAR-T cells according to one exemplary embodiment of the present disclosure, which were prepared using donor 06-derived T cells, against cells not expressing mucin1 (HEK293T);

FIG. 4 shows results of testing cytotoxicity of CAR-T cells according to one exemplary embodiment of the present disclosure, which were prepared using donor 03-derived T cells, against a human breast cancer cell line T47D;

FIG. 5 shows results of testing cytotoxicity of CAR-T cells, which were prepared using donor 04-derived T cells, against a human breast cancer cell line T47D;

FIG. 6 shows results of testing cytotoxicity of CAR-T cells, which were prepared using donor 03-derived T cells, against a human embryonic kidney cell HEK293T;

FIG. 7 shows results of testing cytotoxicity of CAR-T cells, which were prepared using donor 04-derived T cells, against a human embryonic kidney cell HEK293T;

FIG. 8 shows results of testing cytotoxicity of CAR-T cells, which were prepared using donor 04-derived T cells, against HEK293T-V1 obtained by expressing exogenous MUC1-C in a human embryonic kidney cell line;

FIG. 9 shows results of testing cytotoxicity of CAR-T cells according to one exemplary embodiment of the present disclosure, which were prepared using donor 05-derived T cells, against a human breast cancer cell line T47D;

FIG. 10 shows results of testing cytotoxicity of CAR-T cells according to one exemplary embodiment of the present disclosure, which were prepared using donor 06-derived T cells, against a human breast cancer cell line T47D;

FIG. 11 shows results of testing cytotoxicity of CAR-T cells according to one exemplary embodiment of the present disclosure, which were prepared using donor 07-derived T cells, against a human embryonic kidney cell line HEK293T;

FIG. 12 shows results of testing cytotoxicity of CAR-T cells according to one exemplary embodiment of the present disclosure, which were prepared using donor 08-derived T cells, against a human breast cancer cell line HCC70 (#2: 2447_2H08; #3: 2447_3A01; #4: 2447_3A08; #5: 2447_3A09; #6: 2447_3A12; #7: 2447_3B07; #8: 2447_3C08; #9: 2447_3H02; #10: 2447_3H08);

FIG. 13 shows results of differential cytotoxicity of CAR-T cells according to one exemplary embodiment of the present disclosure against a human breast cancer cell line (HCC70) and a normal human breast cell line (MCF10A) at an effector cell (E): target cell (T) ratio of 0.3:1 (#2: 2447_2H08);

FIG. 14 shows results of differential cytotoxicity of CAR-T cells according to one exemplary embodiment of the present disclosure against a human breast cancer cell line (HCC70) and a normal human breast cell line (MCF10A) at an effector cell (E): target cell (T) ratio of 0.1:1 (#2: 2447_2H08);

FIG. 15 shows results of examining tumor growth inhibition after injection of CAR-T cells according to one exemplary embodiment of the present disclosure into cancer animal models which had been injected with PANC1-v1 cells (PANC1 pancreatic cancer cells expressing MUC1);

FIG. 16 shows results of examining the number of human immune cells (hCD45+ cells) in blood 14 days and 28 days after injection of CAR-T cells according to one exemplary embodiment of the present disclosure into cancer animal models which had been injected with PANC1-v1 cells (PANC1 pancreatic cancer cells expressing MUC1);

FIG. 17 shows results of examining tumor growth inhibition after injection of two different doses of CAR-T cells according to one exemplary embodiment of the present disclosure into cancer animal models which had been injected with PANC1-v1 cells (PANC1 pancreatic cancer cells expressing MUC1);

FIG. 18 shows results of examining tumor growth inhibition after injection of CAR-T cells according to one exemplary embodiment of the present disclosure into cancer animal models which had been injected with HCC1954 cells (breast cancer cells naturally expressing MUC1); and FIG. 19 shows results of examining the number of human immune cells (hCD45+ cells) in blood at regular time intervals after injection of CAR-T cells according to one exemplary embodiment of the present disclosure into cancer animal models which had been injected with HCC1954 cells (breast cancer cells naturally expressing MUC1).

DETAILED DESCRIPTION

According to one aspect of the present invention, provided is a polypeptide binding to mucin1. In one preferred embodiment, the polypeptide binding to mucin1 of the present disclosure may be an antibody or an antigen-binding fragment thereof.

In one embodiment, provided is a polypeptide binding to mucin1, the polypeptide comprising a pair of a heavy chain variable (VH) region and a light chain variable (VL) region selected from the following VH and VL regions:

a VH region comprising complementarity-determining region (CDR) 1, 2, and 3 represented by amino acid sequences of SEQ ID NO: 1, SEQ ID NO: 2, and SEQ ID NO: 3, respectively, and a VL region comprising CDR 1, 2, and 3 represented by amino acid sequences of SEQ ID NO: 4, SEQ ID NO: 5, and SEQ ID NO: 6, respectively;

a VH region comprising CDR 1, 2, and 3 represented by amino acid sequences of SEQ ID NO: 11, SEQ ID NO: 12, and SEQ ID NO: 13, respectively, and a VL region comprising CDR 1, 2, and 3 represented by amino acid sequences of SEQ ID NO: 14, SEQ ID NO: 15, and SEQ ID NO: 16, respectively;

a VH region comprising CDR 1, 2, and 3 represented by amino acid sequences of SEQ ID NO: 21, SEQ ID NO: 22, and SEQ ID NO: 23, respectively, and a VL region comprising CDR 1, 2, and 3 represented by amino acid sequences of SEQ ID NO: 24, SEQ ID NO: 25, and SEQ ID NO: 26, respectively;

a VH region comprising CDR 1, 2, and 3 represented by amino acid sequences of SEQ ID NO: 31, SEQ ID NO: 32, and SEQ ID NO: 33, respectively, and a VL region comprising CDR 1, 2, and 3 represented by amino acid sequences of SEQ ID NO: 34, SEQ ID NO: 35, and SEQ ID NO: 36, respectively;

a VH region comprising CDR 1, 2, and 3 represented by amino acid sequences of SEQ ID NO: 41, SEQ ID NO: 42, and SEQ ID NO: 43, respectively, and a VL region comprising CDR 1, 2, and 3 represented by amino acid sequences of SEQ ID NO: 44, SEQ ID NO: 45, and SEQ ID NO: 46, respectively;

a VH region comprising CDR 1, 2, and 3 represented by amino acid sequences of SEQ ID NO: 51, SEQ ID NO: 52, and SEQ ID NO: 53, respectively, and a VL region comprising CDR 1, 2, and 3 represented by amino acid sequences of SEQ ID NO: 54, SEQ ID NO: 55, and SEQ ID NO: 56, respectively;

a VH region comprising CDR 1, 2, and 3 represented by amino acid sequences of SEQ ID NO: 61, SEQ ID NO: 62, and SEQ ID NO: 63, respectively, and a VL region comprising CDR 1, 2, and 3 represented by amino acid sequences of SEQ ID NO: 64, SEQ ID NO: 65, and SEQ ID NO: 66, respectively;

a VH region comprising CDR 1, 2, and 3 represented by amino acid sequences of SEQ ID NO: 71, SEQ ID NO: 72, and SEQ ID NO: 73, respectively, and a VL region comprising CDR 1, 2, and 3 represented by amino acid sequences of SEQ ID NO: 74, SEQ ID NO: 75, and SEQ ID NO: 76, respectively;

a VH region comprising CDR 1, 2, and 3 represented by amino acid sequences of SEQ ID NO: 81, SEQ ID NO: 82, and SEQ ID NO: 83, respectively, and a VL region comprising CDR 1, 2, and 3 represented by amino acid sequences of SEQ ID NO: 84, SEQ ID NO: 85, and SEQ ID NO: 86, respectively; and a VH region comprising CDR 1, 2, and 3 represented by amino acid sequences of SEQ ID NO: 91, SEQ ID NO: 92, and SEQ ID NO: 93, respectively, and a VL region comprising CDR 1, 2, and 3 represented by amino acid sequences of SEQ ID NO: 94, SEQ ID NO: 95, and SEQ ID NO: 96, respectively.

a VH region comprising an amino acid sequence of SEQ ID NO: 27 and a VL region comprising an amino acid sequence of SEQ ID NO: 28;

a VH region comprising an amino acid sequence of SEQ ID NO: 37 and a VL region comprising an amino acid sequence of SEQ ID NO: 38;

TABLE 1

| Clone name | CDR | | | | | |
|---|---|---|---|---|---|---|
| | VH | | | VL | | |
| | CDR1 | CDR2 | CDR3 | CDR1 | CDR2 | CDR3 |
| 2445_1F09 | GFTVSSNY (SEQ ID NO: 1) | IYSGGST (SEQ ID NO: 2) | DRGWNHGMDV (SEQ ID NO: 3) | SSEVGSRY (SEQ ID NO: 4) | KND (SEQ ID NO: 5) | AAWDDSLNGYV (SEQ ID NO: 6) |
| 2447_2H08 | GYTFTNYG (SEQ ID NO: 11) | ISAYNGNT (SEQ ID NO: 12) | DPHILTGYYRGGWFDP (SEQ ID NO: 13) | SLRTSY (SEQ ID NO: 14) | GKT (SEQ ID NO: 15) | HSRDSNDNYLEVV (SEQ ID NO: 16) |
| 2447_3A01 | GFTFDDYA (SEQ ID NO: 21) | ISWNSGSI (SEQ ID NO: 22) | DISSGWYPGTFDY (SEQ ID NO: 23 | SLRSYY (SEQ ID NO: 24) | GKN (SEQ ID NO: 25) | SSRDSSDDVV (SEQ ID NO: 26) |
| 2447_3A08 | GYTFTSYG (SEQ ID NO: 31) | ISAYNGNT (SEQ ID NO: 32) | DRATIFGVVTPFDY (SEQ ID NO: 33 | SIRSYS (SEQ ID NO: 34) | GKN (SEQ ID NO: 35) | NSRDSSGNRVV (SEQ ID NO: 36) |
| 2447_3A09 | GFTFDDYA (SEQ ID NO: 41) | ISWNSGSI (SEQ ID NO: 42) | DVSSGWYWYAFDI (SEQ ID NO: 43) | SLRSYY (SEQ ID NO: 44) | GKN (SEQ ID NO: 45) | NSRDSGGSVV (SEQ ID NO: 46) |
| 2447_3A12 | GYTFTSYG (SEQ ID NO: 51) | ISAYNGNT (SEQ ID NO: 52) | DPHILTGYYRGGWFDP (SEQ ID NO: 53) | SLRSYY (SEQ ID NO: 54) | GKN (SEQ ID NO: 55) | NSRDSSGNHRV (SEQ ID NO: 56) |
| 2447_3B07 | GFTFDDYA (SEQ ID NO: 61) | TSWDGGST (SEQ ID NO: 62) | DHSSGWYNGGMDV (SEQ ID NO: 63) | SLRSYY (SEQ ID NO: 64) | GKN (SEQ ID NO: 65) | NSRDSSGNHVV (SEQ ID NO: 66) |
| 2447_3C08 | GFTFDDYA (SEQ ID NO: 71) | ISWNSGSI (SEQ ID NO: 72) | DRGSGYEGNYYGMDV (SEQ ID NO: 73) | SLRSYY (SEQ ID NO: 74) | GKN (SEQ ID NO: 75) | NSRDSSGNHYV (SEQ ID NO: 76) |
| 2447_3H02 | GFTFDDYA (SEQ ID NO: 81) | ISWDSGSI (SEQ ID NO: 82) | DVSSGWYWYAFDI (SEQ ID NO: 83) | ILRSYY (SEQ ID NO: 84) | GKN (SEQ ID NO: 85) | NSRDSSGNRVV (SEQ ID NO: 86) |
| 2447_3H08 | GFTFDDYA (SEQ ID NO: 91) | ISWNSGSI (SEQ ID NO: 92) | DRSSGWYTGSFDY (SEQ ID NO: 93) | SLRSYY (SEQ ID NO: 94) | GKN (SEQ ID NO: 95) | QSRDSSDNRVL (SEQ ID NO: 96) |

In another embodiment, provided is a polypeptide binding to mucin1, the polypeptide comprising a pair of a heavy chain variable (VH) region and a light chain variable (VL) region selected from the following VH and VL regions:

a VH region comprising an amino acid sequence of SEQ ID NO: 7 and a VL region comprising an amino acid sequence of SEQ ID NO: 8;

a VH region comprising an amino acid sequence of SEQ ID NO: 17 and a VL region comprising an amino acid sequence of SEQ ID NO: 18;

a VH region comprising an amino acid sequence of SEQ ID NO: 47 and a VL region comprising an amino acid sequence of SEQ ID NO: 48;

a VH region comprising an amino acid sequence of SEQ ID NO: 57 and a VL region comprising an amino acid sequence of SEQ ID NO: 58;

a VH region comprising an amino acid sequence of SEQ ID NO: 67 and a VL region comprising an amino acid sequence of SEQ ID NO: 68;

a VH region comprising an amino acid sequence of SEQ
ID NO: 77 and a VL region comprising an amino acid
sequence of SEQ ID NO: 78;

a VH region comprising an amino acid sequence of SEQ
ID NO: 87 and a VL region comprising an amino acid
sequence of SEQ ID NO: 88; and a VH region comprising an amino acid sequence of SEQ
ID NO: 97 and a VL region comprising an amino acid
sequence of SEQ ID NO: 98.

TABLE 2

| Clone name | VH | VL |
|---|---|---|
| 2445_1F09 | EVQLLETGGGLIQPGGSLRLSCAAS GFTVSSNYMSWVRQAPGKGLEWVS VIYSGGSTYYADSVKGRFTISRDNS KNTLYLQMNSLRAEDTAVYYCARD RGWNHGMDVWGQGTLVTVSS (SEQ ID NO: 7) | QSGLTQPPSASGTPGQRVTISCSGG SSEVGSRYVSWYQQLPGTAPRLLI YKNDRRPSGVPDRESGSKSGSSAS LAISGLRSEDEADYYCAAWDDSLN GYVFGTGTKLTVL (SEQ ID NO: 8) |
| 2447_2H08 | EVQLVQSGAEVKKPGASVKVSCKA SGYTFTNYGISWVRQAPGQGLEWM GWISAYNGNTNYAQKLQGRVTMTT DTSTSTAYMELRSLRSDDTAVYYCA RDPHILTGYYRGGWFDPWGQGTTV TVSS (SEQ ID NO: 17) | SYELTQDPAVSVALGQTVTITCQG DSLRTSYAGWLQQKPGQAPVLVL YGKTSRPSGIPDRESGSTSGNTASL TITGAQAEDEAEYFCHSRDSNDNY LEVVFGGGTKLTVL (SEQ ID NO: 18) |
| 2447_3A01 | EVQLLESGGGLVQPGGSLRLSCAAS GFTFDDYAMHWVRQAPGKGLEWV SGISWNSGSIVYADFVKGRFTISRDN AKNSLYLQMNSLRAEDTALYYCAK DISSGWYPGTFDYWGQGTLVTVSS (SEQ ID NO: 27) | SYELTQDPAVSVALGQTVRITCQG DSLRSYYASWYQQKPGQAPVLVIY GKNNRPSGIPDRFSGSSSGNTASLT VTGAQAEDEADYYCSSRDSSDDV VFGGGTQLTVL (SEQ ID NO: 28) |
| 2447_3A08 | EVQLVQSGAEVKKPGASVKVSCKA SGYTFTSYGISWVRQAPGQGLEWM GWISAYNGNTNYAQKLQGRVTMTT DTSTSTAYMELRSLRSDDTAVYYCA RDRATIFGVVTPFDYWGQGTLVTVS S (SEQ ID NO: 37) | SYELTQDPAVSVALGQTVRITCQG DSIRSYSASWYQQKPGQAPRLVIY GKNNRPSGIPDRVSGSTSGNTASLT VTGAQAEDEADYYCNSRDSSGNR VVFGGGTQLTVL (SEQ ID NO: 38) |
| 2447_3A09 | EVQLLESGGGLVQPGRSLRLSCAAT GFTFDDYAMHWVRQAPGKGLEWV SGISWNSGSIGYADSVKGRFTISRDN AKNSLYLQMNSLRAEDTASYYCAK DVSSGWYWYAFDIWGQGTLVTVSS (SEQ ID NO: 47) | SYELTQDPAVSVALGQTVRITCQG DSLRSYYASWYQQKPGQAPVLVIY GKNNRPSGIPGRFSGSSSGNTASLT VTGAQAEDEADYYCNSRDSGGSV VFGGGTKLTVL (SEQ ID NO: 48) |
| 2447_3A12 | EVQLVQSGAEVKKPGASVKVSCKA SGYTFTSYGISWVRQAPGQGLEWM GWISAYNGNTNYAQKLRGRVTMTT DTSTSTAYMELRSLRSDDTAVYYCA RDPHILTGYYRGGWFDPWGQGTLV TVSS (SEQ ID NO: 57) | SYELTQDPAVSVALGQTVRITCQG DSLRSYYASWYQQKPGQAPVLVIY GKNNRPSGIPDRESGSSSGNTASLTI TGAQAEDEADYYCNSRDSSGNHR VFGGGTKLTVL (SEQ ID NO: 58) |
| 2447_3B07 | QVQLVESGGVVVQPGGSLRLSCAA SGFTFDDYAMHWVRQAPGRGLEW VSLTSWDGGSTYYADSVKGRFTISR DNSKNSLYLQMNSLRAEDTALYYC AKDHSSGWYNGGMDVWGQGTMV TVSS (SEQ ID NO: 67) | SYELTQDPAVSVALGQTVRITCQG DSLRSYYASWYQQKPGQAPVLVIY GKNNRPSGIPDRFSGSSSGNTASLTI TGAQAEDEADYYCNSRDSSGNHV VFGGGTKLTVL (SEQ ID NO: 68) |
| 2447_3C08 | EVQLLESGGGLVQPGGSLRLSCAAS GFTFDDYAMHWVRQAPGKGLEWV SGISWNSGSIGYADSVKGRFTISRDN AKNSLYLQMNSLRAEDTALYYCAK DRGSGYEGNYYGMDVWGQGTLVT VSS (SEQ ID NO: 77) | SYELTQDPAVSVALGQTVRITCQG DSLRSYYASWYQQKPGQAPVLVIY GKNNRPSGIPDRFSGTTSGNTASLT ITGAQAEDEADYYCNSRDSGNHY VFGTGTKVTVL (SEQ ID NO: 78) |
| 2447_3H02 | EVQLLESGGGLVQPGRSLRLSCAAS GFTFDDYAMHWVRQAPGKGLEWV SGISWDSGSIGYADSVKGRFTISRDN AKNSLYLQMNSLRAEDTALYYCAK DVSSGWYWYAFDIWGQGTLVTVSS (SEQ ID NO: 87) | SYELTQDPAVSVALGQTVRITCQG DILRSYYASWYQQKPGQAPVLVIY GKNNRPSGIPDRFSGSSSGNTASLTI TGAQAEDEADYYCNSRDSSGNRV VFGGGTKLTVL (SEQ ID NO: 88) |

TABLE 2-continued

| Clone name | VH | VL |
|---|---|---|
| 2447_3H08 | EVQLLESGGGLVQPGRSLRLSCAAS GFTFDDYAMHWVRQAPGKGLEWV SGISWNSGSIDYADSVKGRFTISRDN SKNTLYLQMNSLRAEDTAVYYCAR DRSSGWYTGSFDYWGQGTLVTVSS (SEQ ID NO: 97) | SYELTQDPAVSVALGQTVRITCQG DSLRSYYASWYRQKPGQAPVLVIY GKNNRPSGIPDRFSGSSSGNTASLTI IGAQAEDEADYYCQSRDSSDNRVL FGGGTKVTVL (SEQ ID NO: 98) |

As used herein, the term "antibody" collectively refers to a protein that specifically binds to a specific antigen, and is used in the broadest sense, and it may be a protein produced in the immune system by stimulation of an antigen or a protein synthesized chemically or prepared recombinantly. The type thereof is not particularly limited. Specifically, the antibody encompasses monoclonal antibodies (including full-length monoclonal antibodies), polyclonal antibodies, multispecific antibodies (e.g., bispecific antibodies), synthetic antibodies (also called antibody mimetics), chimeric antibodies, humanized antibodies, human antibodies, or antibody fusion proteins (also called antibody conjugates), provided such antibodies exhibit a desired biological activity.

An intact antibody (e.g., IgG-type) has a structure having two full-length light chains and two full-length heavy chains, each light chain associated with the heavy chain through disulfide bonds. A constant region of an antibody is divided into a heavy chain constant region and a light chain constant region, wherein the heavy chain constant region has a gamma (γ), mu (μ), alpha (α), delta (δ), or epsilon (ε) type, and a subclass of gamma1 (γ1), gamma2 (γ2), gamma3 (γ3), gamma4 (γ4), alpha1 (α1), or alpha2 (α2), and the light chain constant region has a kappa (κ) or lambda (λ) type.

The term "antigen-binding fragment" refers to a fragment of an antibody, which is able to specifically bind to an antigen even though at least part of amino acids present in the full-length chain is absent. Such a fragment is biologically active in that it binds to a target antigen, and competes with other antigen-binding molecules including an intact antibody for binding to a given epitope. The antigen-binding fragment may not include a constant heavy chain domain (i.e., CH2, CH3, and CH4 according to antibody isotypes) of Fc region of an intact antibody. Examples of the antigen-binding fragment may include single chain variable fragments (scFvs) (e.g., scFv, (scFv)$_2$, etc.), fragment antigen binding (Fab) (e.g., Fab, Fab', F(ab')$_2$, etc.), domain antibodies, peptibodies, minibodies, intrabodies, diabodies, triabodies, tetrabodies, or and single-chain antibodies, etc., but are not limited thereto. Further, the antigen-binding fragment may be scFv, or a fusion polypeptide (scFv-Fc), in which scFv is fused with an Fc region of an immunoglobulin (e.g., IgA, IgD, IgE, IgG (IgG1, IgG2, IgG3, IgG4), IgM, etc.), or a fusion polypeptide (scFv-Ck (kappa constant region) or scFv-Cλ (lambda constant region), in which scFv is fused with a light chain constant region (e.g., kappa or lambda), but is not limited thereto.

The term "heavy chain" is interpreted as having a meaning including a full-length heavy chain including a variable region domain VH including an amino acid sequence having a variable region sequence sufficient to impart specificity to an antigen and three constant region domains, $C_{H1}$, $C_{H2}$ and $C_{H3}$, and a hinge, and fragments thereof. Further, the term "light chain" is interpreted as having a meaning including a full-length light chain including a variable region domain $V_L$ including an amino acid sequence having a variable region sequence sufficient to impart specificity to an antigen and a constant region domain $C_L$, and fragments thereof.

The term "complementarity-determining region (CDR)" refers to a region in a variable region of an antibody, which imparts binding specificity or binding affinity to an antigen. Generally, there are three CDRs (CDR-H1, CDR-H2, CDR-H3) in a heavy chain variable region, and three CDRs (CDR-L1, CDR-L2, CDR-L3) in a light chain variable region. The CDRs may provide key contact residues for an antibody or a fragment thereof binding to an antigen or an epitope. The term "framework region (FR)" refers to non-CDR regions of variable regions of heavy and light chains. Generally, there are four FRs (FR-H1, FR-H2, FR-H3, and FR-H4) in a heavy chain variable region, and four FRs (FR-L1, FR-L2, FR-L3 and FR-L4) in a light chain variable region. The precise amino acid sequence boundaries of a given CDR or FR may be readily determined using any of a number of well-known schemes, such as Kabat numbering scheme, Chothia numbering scheme, Contact numbering scheme, IMGT numbering scheme, Aho numbering scheme, AbM numbering scheme, etc.

The term "variable region" refers to a domain of a heavy chain or light chain of an antibody, which is involved in binding of the antibody to an antigen. The heavy chain variable (VH) region and the light chain variable (VL) region generally have the similar structure, and each domain includes four conserved framework regions (FRs) and three CDRs.

In a specific embodiment, the mucin1-binding polypeptide of the present disclosure may be a single chain variable fragment (scFv), a peptibody, a fragment antigen binding (Fab), a monoclonal antibody, a bispecific antibody, a minibody, a domain antibody, a synthetic antibody, a chimeric antibody, a humanized antibody, a human antibody, or an antibody fusion protein, but is not limited thereto.

In a preferred specific embodiment, the mucin1-binding polypeptide of the present disclosure may be a single chain variable fragment (scFv).

The term "single chain variable fragment (scFv)" refers to a single chain antibody fragment, in which a heavy chain variable (VH) region and a light chain variable (VL) region of an antibody are linked via a covalent bond. The VH region and the VL region may be linked to each other directly or via a linker.

The linker may be a water-soluble and/or flexible linker. For example, the N-terminus of VH and the C-terminus of VL or the C-terminus of VH and the N-terminus of VL may be linked to each other via the linker. The linker may be a peptide linker, for example, having a length of 10 to 30 amino acids, 10 to 25 amino acids, 10 to 20 amino acids, 10 to 15 amino acids, 15 to 30 amino acids, 15 to 25 amino acids, 15 to 20 amino acids, specifically, 10, 11, 12, 13, 14, 15, 16, 17, 18, 19, 20, 21, 22, 23, 24, 25, 26, 27, 28, 29, or 30 amino acids, but is not limited thereto.

Amino acid sequences suitable for the linker are known in the art. For example, the linker may be rich in glycine for flexibility, and may include serine (Ser), asparagine (Asn), alanine (Ala), or threonine (Thr) for solubility. The linker may consist of a total of 1 to 100, 2 to 50, or 5 to 25 of one or more selected from the group consisting of Gly, Asn, Ser, Thr, and Ala. For non-limiting example, the amino acid sequence of the linker may be a sequence having various numbers of repeats of GGGS (SEQ ID NO: 117) or GGGGS (SEQ ID NO: 118), for example, 2, 3, 4, and 5 repeats thereof. For example, the linker may be GGGGSGGGGSGGGGS (SEQ ID NO: 119), GGGGSGGGGSGGGGSGGGGS (SEQ ID NO: 120), or GGGGSGGGGSGGGAS (SEQ ID NO: 116), but is not limited thereto.

scFv retains antigen specificity of the original antibody despite removal of constant regions and introduction of a linker. scFv may be expressed from polynucleotides encoding the VH region and the VL region, but is not limited thereto.

In a preferred embodiment, provided is an scFv polypeptide comprising an amino acid sequence selected from the group consisting of SEQ ID NO: 9, SEQ ID NO: 19, SEQ ID NO: 29, SEQ ID NO: 39, SEQ ID NO: 49, SEQ ID NO: 59, SEQ ID NO: 69, SEQ ID NO: 79, SEQ ID NO: 89, and SEQ ID NO: 99.

In the present disclosure, variants retaining an activity equivalent to that of the antibody or the antigen-binding fragment, for example, variants having about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% or more identity to the amino acid sequences described herein and retaining a biological activity equivalent thereto may be also included in the scope of the present disclosure.

According to another aspect of the present invention, provided is an isolated polynucleotide encoding the mucin1-binding polypeptide.

In one preferred embodiment, the polynucleotide may include a nucleotide sequence selected from the group consisting of SEQ ID NO: 10, SEQ ID NO: 20, SEQ ID NO: 30, SEQ ID NO: 40, SEQ ID NO: 50, SEQ ID NO: 60, SEQ ID NO: 70, SEQ ID NO: 80, SEQ ID NO: 90, and SEQ ID NO: 100. Further, the present invention may include an isolated polynucleotide encoding a polypeptide having about 90%, about 91%, about 92%, about 93%, about 94%, about 95%, about 96%, about 97%, about 98% or about 99% or more identity to the sequence and retaining equivalent activity thereto. In an embodiment, the polynucleotide may be codon-optimized for expression in humans.

According to still another aspect, provided is a vector comprising the polynucleotide encoding the mucin1-binding polypeptide.

In the vector, the polynucleotide may be operably linked to a promoter. The term "operatively linked" refers to a functional linkage between a nucleotide expression control sequence (e.g., a promoter sequence) and another nucleotide sequence. The control sequence may be operably linked to control transcription and/or translation of another nucleotide sequence.

The vector may be constructed as a vector for typically cloning or expression. The vector for expression may be those commonly used in the art to express a foreign protein in plants, animals, or microorganisms. The vector may be constructed through various methods known in the art.

The vector may be constructed using a prokaryotic cell or a eukaryotic cell as a host. For example, when the vector to be used is an expression vector and a prokaryotic cell is used as a host, the vector may generally include a strong promoter capable of initiating transcription (e.g., pL$^\lambda$ promoter, CMV promoter, trp promoter, lac promoter, tac promoter, T7 promoter, etc.), a ribosome binding site for initiating translation, and a transcription/translation termination sequence. When a eukaryotic cell is used as a host, an origin of replication which is included in the vector and acts in the eukaryotic cell may include f1 origin of replication, SV40 origin of replication, pMB1 origin of replication, adeno origin of replication, AAV origin of replication, BBV origin of replication, etc., but is not limited thereto. Further, a promoter derived from genomes of mammalian cells (e.g., a metallothionein promoter) or a promoter derived from mammalian viruses (e.g., an adenovirus late promoter, a vaccinia virus 7.5K promoter, a SV40 promoter, a cytomegalovirus promoter, and a tk promoter of HSV) may be used, and a transcription termination sequence may be, in general, a polyadenylation sequence. As needed, the vector may further include an enhancer sequence, 5'- and 3'-untranslated regions, a secretion signal sequence, a splice junction, a selection marker (e.g., an antibiotic resistance gene), etc.

According to still another aspect, provided is a cell comprising the vector comprising the polynucleotide encoding the mucin1-binding polypeptide.

The cell may be obtained by introducing the vector into an appropriate host cell. The host cell comprising the vector may be useful for cloning or expressing the polynucleotide included in the vector. The host cell is a cell capable of stably and continuously cloning or expressing the vector, and any host cell known in the art may be used. For example, a prokaryotic cell may include, e.g., *E. coli* JM109, *E. coli* BL21, *E. coli* RR1, *E. coli* LE392, *E. coli* B, *E. coli* X 1776, *E. coli* W3110, strains of the genus *Bacillus* such as *Bacillus subtilis, Bacillus thuringiensis*, and strains of the family enterobacteriaceae such as *Salmonella typhimurium, Serratia marcescens* and various *Pseudomonas* species. When transformed into a eukaryotic cell, the host cell may include a yeast (*Saccharomyces cerevisiae*) cell, an insect cell, a plant cell, and an animal cell, e.g., Sp2/0, Chinese hamster ovary (CHO) K1, CHO DG44, PER.C6, W138, BHK, COS-7, 293, HepG2, Huh7, 3T3, RIN, MDCK cell line, etc., but is not limited thereto.

Delivery (introduction) of the polynucleotide or the vector comprising the same into the host cell may be carried out by using a delivering method widely known in the art. With regard to the delivering method, for example, when the host cell is a prokaryotic cell, a CaCl$_2$) method or an electroporation method may be used, and when the host cell is a eukaryotic cell, a microinjection method, a calcium phosphate precipitation method, an electroporation method, a liposome-mediated transfection method, and gene bombardment may be used, but is not limited thereto.

A method of selecting the transformed host cell may be easily carried out using a phenotype expressed by a selection marker according to a method well known in the art. For example, when the selection marker is a specific antibiotic resistance gene, the transformant may be easily selected by culturing the transformant in a medium containing the antibiotic. The transformed host cells may be cultured for a period sufficient for polypeptide expression or secretion, and the polypeptide may be separated and purified by a method of separating and purifying proteins commonly used, for example, a method of using solubility, such as salting out, solvent precipitation, etc., a method of using a molecular weight difference, such as dialysis, ultrafiltration, gel filtration, sodium dodecyl sulfate-polyacrylamide gel electrophoresis, etc., a method of using a charge, such as ion exchange chromatography or hydroxylapatite chromatography, etc., a method of using specific affinity, such as affinity chromatography, etc., a method of using a hydrophobicity difference, such as reverse-phase high performance liquid chromatography, etc., a method of using an isoelectric point difference, such as isoelectric point electrophoresis, etc.

According to still another aspect of the present invention, provided is a chimeric antigen receptor (CAR) comprising the mucin1-binding polypeptide. The mucin1-binding polypeptide is suitable for use in chimeric antigen receptors because it may be engineered to be expressed as part of a single chain along with other CAR components.

The chimeric antigen receptor may typically include an extracellular domain comprising the mucin1-binding polypeptide; a transmembrane domain; an intracellular signaling domain or a T cell activation domain. Further, the extracellular domain may further include a spacer region (or hinge region) between the polypeptide and the transmembrane domain. Further, the chimeric antigen receptor may further include one or more co-stimulatory domains, and preferably, the co-stimulatory domains may be placed between the transmembrane domain and the intracellular signaling domain.

Accordingly, in one preferred embodiment, the chimeric antigen receptor may include an extracellular domain comprising the mucin1-binding polypeptide; a hinge domain; a transmembrane domain; one or more co-stimulatory domains; and an intracellular signaling domain. Each domain may be heterogeneous. In other words, it may consist of sequences derived from different protein chains. Each domain may be linked by a short oligo- or polypeptide linker, for example, a linker having a length of 2 to 10 amino acids. In addition, the chimeric antigen receptor may consist of one polypeptide chain in which the respective domains are linked.

The extracellular domain includes the mucin1-binding polypeptide as described above, which recognizes mucin1 expressed on the cancer cell surface.

The extracellular domain may further include a spacer region (or hinge region). The spacer region may be placed between the mucin1-binding polypeptide and the transmembrane domain. The spacer region allows the mucin1-binding polypeptide to more flexibly recognize the target antigen at a predetermined distance from the cell membrane of CAR-T cell. The spacer region may be typically a polypeptide having a length of 10 or more amino acids, for example, a length of 10 to 300 amino acids, a length of 10 to 250 amino acids, a length of 10 to 200 amino acids, a length of 10 to 150 amino acids, a length of 10 to 100 amino acids, a length of 10 to 50 amino acids, but is not limited thereto.

The spacer region may be exemplified by a hinge region of CD8α or CD28, a constant region of an immunoglobulin (IgG), etc., and mutations may be introduced to remove off-target effects thereby. For example, the immunoglobulin constant region may be derived from an IgG hinge alone, a part or all of CH2 and CH3 domains, for example, an Fc region. IgG may be preferably IgG2 or IgG4. In a specific embodiment, the spacer may be a chimeric polypeptide containing one or more of hinge, CH2 and CH3 sequences derived from IgG2, IgG4, and/or IgG2 and IgG4. In a specific embodiment, the hinge domain may be represented by a sequence of SEQ ID NO: 112, but is not limited thereto.

The transmembrane domain serves to connect a cell membrane domain and a signaling domain inside the cell membrane, and may be derived from natural or synthetic sources. When derived from a natural source, the domain may be derived from any membrane-binding or transmembrane protein. For example, the transmembrane domain may be a transmembrane domain of a T cell receptor alpha, beta, or zeta chain, CD3 epsilon, CD4, CD5, CD8, CD9, CD16, CD22, CD28, CD33, CD37, CD45, CD64, CD80, CD86, CD134, CD137, or CD154, but is not limited thereto. In one preferred embodiment, the transmembrane domain may be a transmembrane domain of CD28 or CD8, but is not limited thereto. When derived from a synthetic source, the synthetic transmembrane domain may include hydrophobic residues, such as leucine and valine, and may include phenylalanine, tryptophan, and valine at each end thereof, but is not limited thereto. In one embodiment, the transmembrane domain may be represented by a sequence of SEQ ID NO: 113, but is not limited thereto.

The co-stimulatory domain is a site to which co-stimulatory signals are transmitted, and it is a site that transmits signals for CAR-T cells to trigger an immune response and proliferation. The co-stimulatory domain may be selectively introduced to improve CAR-T cell proliferation, cytotoxicity, sustained response, and lifespan extension. The co-stimulatory domain may be one or more, for example, one, two, or three selected from signaling domains of CD28, OX-40 (CD134), 4-1BB (CD137), CD2, CD7, CD27, CD30, CD40, PD-1, ICOS, LFA-1 (CD11a/CD18), CD3 gamma, CD3 delta, CD3 epsilon, CD247, CD276 (B7-H3), LIGHT, (TNFSF14), NKG2C, Ig alpha (CD79a), DAP-10, Fc gamma receptor, MHC class I molecule, TNF receptor protein, immunoglobulin protein, cytokine receptor, integrin, signaling lymphocytic activation molecule (SLAM), activating NK cell receptor, BTLA, Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8 beta, IL-2R beta, IL-2R gamma, IL-7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAMF1 (CD150, IPO-3), BLAME (SLAMF8), SELPLG (CD162), LTBR, LAT, GADS, SLP-76, PAG/Cbp, or CD19a, but is not limited thereto. In one preferred embodiment, the co-stimulatory domain may be one or more, for example, one, two, or three selected from signaling domains of CD28, OX-40 (CD134), 4-1BB (CD137), CD27, or ICOS, but is not limited thereto. In an embodiment, the co-stimulatory domain may be represented by a sequence of SEQ ID NO: 114, but is not limited thereto.

The intracellular signaling domain is a site that activates a T cell immune response to an antigen bound to the mucin1-binding polypeptide. The intracellular signaling domain may be a component of the T cell receptor (TCR) or may include a signaling motif known as an immunoreceptor tyrosine-based activation motif (ITAM). For example, the intracellular signaling domain may be a signaling domain derived from TCR or CD3 zeta, FcR gamma, CD3 gamma, CD3 delta and CD3 epsilon, but is not limited thereto. For a preferred example, the intracellular signaling domain may be a signaling domain of CD3 zeta, but is not limited thereto. The intracellular signaling domain may activate CAR-T cells when the mucin1-binding polypeptide region of the extracellular domain binds to a target. For example, CAR may stimulate T cell function, e.g., cell lytic activity or T-helper activity, and may induce secretion of cytokines or other factors. In some embodiments, the intracellular signaling domain may be represented by a sequence of SEQ ID NO: 115, but is not limited thereto.

In some embodiments, CAR may be expressed in a form comprising a signal sequence. In addition, CAR may be expressed together with additional sequences useful for monitoring expression, for example, a ribosomal skip sequence such as 2A peptide or a truncated cell surface polypeptide (tHER2 or tEGFR or truncated PSMA, etc.).

According to still another aspect of the present invention, provided is an isolated polynucleotide encoding the chimeric antigen receptor. In some embodiments, the polynucleotide may be codon optimized for expression in humans.

According to still another aspect of the present invention, provided is a vector comprising the polynucleotide encoding the chimeric antigen receptor. The vector may be constructed as a vector for gene cloning, a vector for protein expression, or a vector for gene delivery. The details of the vector for cloning or expression are as described above.

Any vector known in the art may be suitable for the present invention. For example, the vector may be a viral vector. For example, the vector is a retrovirus vector, a DNA vector, a murine leukemia virus vector, an SFG vector, a plasmid, an RNA vector, an adenovirus vector, a baculovirus vector, an Epstein Barr virus vector, a papovavirus vector, a vaccinia virus vector, a herpes simplex virus vector, an adenovirus-associated vector (AAV), or a lentivirus vector, but is not limited thereto.

According to still another aspect of the present invention, provided is an immune cell expressing the chimeric antigen receptor comprising the mucin1-binding polypeptide.

The immune cell may include T cells, tumor infiltrating lymphocytes (TIL), natural killer (NK) cells, TCR-expressing cells, dendritic cells, or NK-T cells, but is not limited thereto. In addition, the immune cell may be derived from human induced pluripotent stem cells (iPSCs). The immune cell may be derived from any known source. For example, the immune cell may be differentiated in vitro from a population of hematopoietic stem cells, or obtained from a patient. The immune cell may be obtained from, for example, peripheral blood mononuclear cells (PBMC), bone marrow, a lymph node tissue, umbilical cord blood, a thymus tissue, a tissue from an infection site, ascites, pleural effusion, a splenic tissue, and a tumor. In addition, the immune cell may be derived from one or more immune cell lines available in the related art.

The immune cell may be autologous or allogenic. Autologous means those derived from a patient to be treated. Allogeneic means those derived from another individual of the same species as the patient to be treated.

In addition, the immune cell may be derived from human induced pluripotent stem cells (iPSCs). As compared with autologous or allogeneic immune cells, iPSC-derived immune cells may self-proliferate. Thus, mass-proliferation thereof is easy, and it is possible to prepare a general-purpose cell therapy applicable to all people, and there are advantages of homogeneous production and cost reduction.

The immune cell may be transfected or transduced by a vector using a method of microinjection, electroporation, sonication, biolistics (e.g., gene gun), lipid transfection, polymer transfection, calcium phosphate precipitation, protoplast fusion, liposome-mediated transfection, nanoparticles or polyplexes, etc., but is not limited thereto.

According to still another aspect, provided is a composition for preventing or treating cancer, the composition comprising the mucin1-binding polypeptide; the isolated polynucleotide encoding the mucin1-binding polypeptide; the vector comprising the polynucleotide encoding the mucin1-binding polypeptide; the cell comprising the polynucleotide encoding the mucin1-binding polypeptide; the chimeric antigen receptor comprising the mucin1-binding polypeptide; the isolated polynucleotide encoding the chimeric antigen receptor; the vector comprising the polynucleotide encoding the chimeric antigen receptor; or the immune cell comprising the polynucleotide encoding the chimeric antigen receptor, or expressing the chimeric antigen receptor.

According to still another aspect, provided is a method of preventing or treating cancer, the method comprising administering, to a patient in need of preventing or treating cancer, an effective amount of the mucin1-binding polypeptide; the isolated polynucleotide encoding the mucin1-binding polypeptide; the vector comprising the polynucleotide encoding the mucin1-binding polypeptide; the cell comprising the polynucleotide encoding the mucin1-binding polypeptide; the chimeric antigen receptor comprising the mucin1-binding polypeptide; the isolated polynucleotide encoding the chimeric antigen receptor; the vector comprising the polynucleotide encoding the chimeric antigen receptor; or the immune cell comprising the polynucleotide encoding the chimeric antigen receptor, or expressing the chimeric antigen receptor.

According to still another aspect, provided is a composition for preventing or treating cancer, the composition comprising T cells comprising the chimeric antigen receptor comprising the mucin1-binding polypeptide.

According to still another aspect, provided is a method of preventing or treating cancer, the method comprising administering, to a patient in need of preventing or treating cancer, an effective amount of the T cells comprising the chimeric antigen receptor comprising the mucin1-binding polypeptide.

For example, the cancer may be a solid cancer or a blood cancer. Non-limiting examples thereof may include breast cancer, lung cancer, prostate cancer, ovarian cancer, brain cancer, liver cancer, cervical cancer, endometrial cancer, uterine cancer, colon cancer, colorectal cancer, colorectal cancer, rectal cancer, kidney cancer, nephroblastoma, skin cancer, oral squamous cell carcinoma, epidermoid carcinoma, nasopharyngeal cancer, head and neck cancer, bone cancer, esophageal cancer, bladder cancer, lymphoma (e.g., Hodgkin's lymphoma or non-Hodgkin's lymphoma), gastric cancer, pancreatic cancer, testicular cancer, thyroid cancer, follicular carcinoma, melanoma, myeloma, multiple myeloma, mesothelioma, osteosarcoma, myelodysplastic syndrome, tumor of mesenchymal origin, soft tissue sarcoma, liposarcoma, gastrointestinal stromal sarcoma, malignant peripheral nerve sheath tumor (MPNST), Ewing's sarcoma, leiomyosarcoma, mesenchymal chondrosarcoma, lymphosarcoma, fibrosarcoma, rhabdomyosarcoma, teratocarcinoma, neuroblastoma, medulloblastoma, glioma, benign skin tumor, or leukemia. The lung cancer may be, for example, small cell lung carcinoma (SCLC) or non-small cell lung carcinoma (NSCLC). The leukemia may be, for example, acute myeloid leukemia (AML), chronic myelogenous leukemia (CML), acute lymphocytic leukemia (ALL), or chronic lymphocytic leukemia (CLL).

Preferably, the cancer may be MUC1 protein-expressing cancer, and it may be breast cancer, skin cancer, pancreatic cancer, prostate cancer, lung cancer, thyroid cancer, gastric cancer, ovarian cancer, colorectal cancer, liver cancer, gallbladder cancer, kidney cancer, cervical cancer, or bladder cancer, but is not limited thereto. The cancer may be primary or metastatic cancer.

The patient to be treated may be a patient receiving a secondary anti-hyperproliferative therapy. For example, the secondary anti-hyperproliferative therapy may be chemotherapy, radiation therapy, immunotherapy, phototherapy, cryotherapy, toxin therapy, hormone therapy, or surgery.

CAR-T anticancer therapy using T cells including the chimeric antigen receptor including the mucin1-binding polypeptide of the present disclosure may be performed by a series of processes including extracting T cells from the blood of a healthy person or a patient to be treated, genetically engineering the T cells to express the chimeric antigen receptor including the mucin1-binding polypeptide of the present disclosure, expanding and culturing the engineered T cells, and administering the engineered T cells thus cultured to the patient.

In a preferred embodiment, the step of extracting T cells from the blood of a healthy person or a patient to be treated may be performed by extracting T cells after isolating leukocytes from the blood using leukapheresis or aphresis and enriching T cells. T cells may be separated using specific antibody bead conjugates or markers at the level of CD4/CD8 composition. Alternatively, it is also possible to stably obtain a large amount of T cells through differentiation from stem cells.

The step of genetically engineering the extracted T cells to express the chimeric antigen receptor provided in the present disclosure may be performed by, for example, injecting a nucleotide molecule designed to express the chimeric antigen receptor (CAR) into T cells using a vector, for example, a viral vector (a lentivirus vector, a retrovirus vector, etc.). CAR may be introduced in the form of DNA, or CAR may be introduced in the form of RNA, RNA is then reverse-transcribed into DNA by reverse transcriptase, which may be integrated into the genome of T cells. In addition, in the case of allogeneic cell therapy, genetic manipulation to remove or correct genes inducing graft rejection in donor T cells may be additionally performed to prevent rejection, such as graft-versus-host disease (GvHD).

The step of expanding and culturing the engineered T cells may be performed by culturing, proliferating, and expanding T cells according to a culture technique known in the art. In this regard, safety against virus use and a technology for selecting well-made CAR-T cells are required.

Lastly, the step of administering the engineered T cells to the patient may be performed by, for example, infusion. In a preferred embodiment, before CAR-T cell injection, the patient may receive a lymphodepletion chemotherapy with cyclophosphamide or fludarabine to reduce the level of white blood cells. In addition, to improve the persistence of CAR-T cells, cytokines such as IL-2 may be administered together.

The engineered T cells administered to the patient may mediate immune responses against mucin1-expressing tumor cells. These immune responses include activation of T cells, secretion of cytokines such as IL-2 and IFN-gamma by T cells, proliferation and expansion of T cells recognizing tumor antigens, and T cell-mediated specific killing (removal of tumor) of target-positive cells. For example, when CAR specifically binds to mucin1 in CAR-T cells, T cells are activated through phosphorylation of an immunoreceptor tyrosine-based activation motif (ITAM) of CD3 zeta, and subsequently, T cell proliferation, cytotoxicity and/or cytokine secretion may be induced.

As described above, the anticancer therapy using CAR-T cells fundamentally activates the immune system of a patient and exerts a continuous anticancer effect, and thus, it is advantageous in that there is no need to continue administration, and personalized treatment is possible by using the patient's own T cells.

Administration of the composition of the present disclosure may cause, induce, or promote an immune response that inhibits, stops, delays, or prevents the onset or progression of a disease.

The term "effective amount" refers to an amount sufficient to achieve the desired result, e.g., an amount effective to treat or prevent cancer, when administered to subjects, including humans. The effective amount may vary depending on various factors such as a formulation method, administration mode, a patient's age, body weight, sex, disease severity, diet, administration time, administration route, excretion rate, and response sensitivity. Administration dosage or therapeutic regimen may be adjusted to provide an optimal therapeutic response as will be understood by those skilled in the art.

A therapeutic regimen with a therapeutically effective amount may consist of a single-dose administration, or alternatively, may include a series of applications. The duration of the treatment phase is determined by various factors such as a formulation method, administration mode, a patient's age, body weight, sex, disease severity, diet, administration time, administration route, excretion rate, and response sensitivity. It will also be appreciated that the effective dosage of the anti-cancer composition used for treatment may be increased or lowered during the course of an individual therapeutic regimen. Variations in dosage may occur and will be apparent through standard diagnostic analysis known in the art. The composition of the present invention, in some aspects, may be administered before, during, or after treatment with common anticancer agents, radiation therapy, hormone therapy, biotherapy and/or surgical resection of tumor.

The composition of the present disclosure may be provided together with one or more additives selected from the group consisting of pharmaceutically acceptable carriers, diluents, and excipients.

The pharmaceutically acceptable carrier, which is commonly used in the formulation of antibody, may be one or more selected from the group consisting of lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, mineral oil, etc., but is not limited thereto. The composition may further include one or more selected from the group consisting of diluents, excipients, lubricants, wetting agents, sweeteners, flavoring agents, emulsifiers, suspending agents, preservatives, etc., which are commonly used in the preparation of pharmaceutical compositions, in addition to the above components.

The composition may be administered orally or parenterally. When administered parenterally, intravenous injection, subcutaneous injection, intramuscular injection, intraperitoneal injection, endothelial administration, topical administration, intranasal administration, intrapulmonary administration and rectal administration may be used. When administered orally, proteins or peptides are digested, and thus compositions for oral administration may be formulated to coat the active agent or to protect it from degradation in the stomach. In addition, the composition may be administered by any device capable of transporting the active substance to a target cell.

The cells may be administered using standard administration techniques, formulations, or devices. Formulations and devices such as syringes and vials for storage and administration of the composition may be appropriately used. Administration of cells may be autologous, allogeneic, or xenogenic. Peripheral blood-derived immune cells or progeny thereof (e.g., derived in vivo, ex vivo, or in vitro) may be administered via catheter administration, systemic injection, local injection, intravenous injection, or local injection including parenteral administration. When immune cell therapeutics are administered, they may be generally formulated into injectable unit dosage forms (solutions, suspensions, emulsions). In some embodiments, a population of cells may be administered parenterally. Formulations include those for intravenous injection, subcutaneous injection, intramuscular injection, intraperitoneal injection, endothelial administration, topical administration, intranasal administration, intrapulmonary administration, and rectal administration.

In some embodiments, the composition is provided as a sterile liquid preparation, for example, as an isotonic aqueous solution, a suspension, an emulsion, a dispersion, or a viscous composition, which, in some aspects, may be buffered to a selected pH. Liquid preparations are normally easier to prepare than gels, other viscous compositions, and solid compositions. In addition, liquid compositions are particularly convenient to administer by injection. Viscous compositions, on the other hand, may be formulated within the appropriate viscosity range to provide longer contact periods with a specific tissue. Liquid or viscous compositions may include a carrier which may be a solvent or dispersion medium containing, for example, water, saline, phosphate buffered saline, polyol (e.g., glycerol, propylene glycol, liquid polyethylene glycol) and appropriate mixtures thereof.

Sterile injectable solutions may be prepared by incorporating the binding molecule in a solvent, such as in admixture with a suitable carrier, diluent, or excipient such as sterile water, physiological saline, glucose, dextrose, or the like. The compositions may also be lyophilized. The compositions may include auxiliary substances such as wetting, dispersing, or emulsifying agents (e.g., methylcellulose), pH buffering agents, gelling or viscosity enhancing additives, preservatives, flavoring agents, colors, etc., depending upon the route of administration and the desired preparation.

Various additives which enhance stability and sterility of the compositions, including antimicrobial preservatives, antioxidants, chelating agents, and buffers, may be added. Prevention of microbial actions may be ensured by various antibacterial and antifungal agents, for example, parabens, chlorobutanol, phenol, sorbic acid, etc. Prolonged absorption of the injectable pharmaceutical form may be brought about by the use of agents delaying absorption, for example, aluminum monostearate and gelatin.

Hereinafter, the present invention will be described in more detail with reference to the following exemplary embodiments. However, these exemplary embodiments are only for illustrating the present invention, and the scope of the present invention is not limited by these exemplary embodiments.

Example 1. Preparation of scFv Binding to Mucin1

Human mucin1 (SEQ ID NO: 110) was conjugated with CD4 (SEQ ID NO: 111) to prepare a recombinant antigen. From scFv libraries, clones secreting scFv specific to the antigen were screened, and 10 kinds of scFvs specifically binding to mucin1 were selected. Sequence information of 10 kinds of scFvs thus selected and a positive control scFv G03 (a positive control prepared using an amino acid sequence of G3 antibody of Table 6 of WO2018/174544) used in subsequent experiments are shown in Table 3.

TABLE 3

| Clone name | scFv amino acid sequence |
|---|---|
| 2445_ 1F09 | EVQLLETGGGLIQPGGSLRLSCAASGFTVSSNYMSWVRQAPGKGLEWVS VIYSGGSTYYADSVKGRFTISRDNSKNTLYLQMNSLRAEDTAVYYCARDR GWNHGMDVWGQGTLVTVSSGGGGSGGGGSGGGASQSGLTQPPSASGTP GQRVTISCSGGSSEVGSRYVSWYQQLPGTAPRLLIYKNDRRPSGVPDRESG SKSGSSASLAISGLRSEDEADYYCAAWDDSLNGYVFGTGTKLTVL (SEQ ID NO: 9) |
| 2447_ 2H08 | EVQLVQSGAEVKKPGASVKVSCKASGYTFTNYGISWVRQAPGQGLEWM GWISAYNGNTNYAQKLQGRVTMTTDTSTSTAYMELRSLRSDDTAVYYCA RDPHILTGYYRGGWFDPWGQGTTVTVSSGGGGSGGGGSGGGASSYELTQ DPAVSVALGQTVTITCQGDSLRTSYAGWLQQKPGQAPVLVLYGKTSRPSG IPDRESGSTSGNTASLTITGAQAEDEAEYFCHSRDSNDNYLEVVFGGGTKL TVL (SEQ ID NO: 19) |
| 2447_ 3A01 | EVQLLESGGGLVQPGGSLRLSCAASGFTFDDYAMHWVRQAPGKGLEWV SGISWNSGSIVYADFVKGRFTISRDNAKNSLYLQMNSLRAEDTALYYCAK DISSGWYPGTEDYWGQGTLVTVSSGGGGSGGGGSGGGASSYELTQDPAV SVALGQTVRITCQGDSLRSYYASWYQQKPGQAPVLVIYGKNNRPSGIPDR FSGSSSGNTASLTVTGAQAEDEADYYCSSRDSSDDVVFGGGTQLTVL (SEQ ID NO: 29) |
| 2447_ 3A08 | EVQLVQSGAEVKKPGASVKVSCKASGYTFTSYGISWVRQAPGQGLEWM GWISAYNGNTNYAQKLQGRVTMTTDTSTSTAYMELRSLRSDDTAVYYCA RDRATIFGVVTPFDYWGQGTLVTVSSGGGGSGGGGSGGGASSYELTQDP AVSVALGQTVRITCQGDSIRSYSASWYQQKPGQAPRLVIYGKNNRPSGIPD RVSGSTSGNTASLTVTGAQAEDEADYYCNSRDSSGNRVVFGGGTQLTVL (SEQ ID NO: 39) |
| 2447_ 3A09 | EVQLLESGGGLVQPGRSLRLSCAATGFTFDDYAMHWVRQAPGKGLEWV SGISWNSGSIGYADSVKGRFTISRDNAKNSLYLQMNSLRAEDTASYYCAK |

TABLE 3-continued

| Clone name | scFv amino acid sequence |
| --- | --- |
| | DVSSGWYWYAFDIWGQGTLVTVSSGGGGSGGGGSGGGASSYELTQDPA<br>VSVALGQTVRITCQGDSLRSYYASWYQQKPGQAPVLVIYGKNNRPSGIPG<br>RFSGSSSGNTASLTVTGAQAEDEADYYCNSRDSGGSVVFGGGTKLTVL<br>(SEQ ID NO: 49) |
| 2447_<br>3A12 | EVQLVQSGAEVKKPGASVKVSCKASGYTFTSYGISWVRQAPGQGLEWM<br>GWISAYNGNTNYAQKLRGRVTMTTDTSTSTAYMELRSLRSDDTAVYYCA<br>RDPHILTGYYRGGWFDPWGQGTLVTVSSGGGGSGGGGSGGGASSYELTQ<br>DPAVSVVLGQTVRITCQGDSLRSYYASWYQQKPGQAPVLVIYGKNNRPS<br>GIPDRFSGSSSGNTASLTITGAQAEDEADYYCNSRDSSGNHRVFGGGTKLT<br>VL (SEQ ID NO: 59) |
| 2447_<br>3B07 | QVQLVESGGVVVQPGGSLRLSCAASGFTFDDYAMHWVRQAPGRGLEWV<br>SLTSWDGGSTYYADSVKGRFTISRDNSKNSLYLQMNSLRAEDTALYYCA<br>KDHSSGWYNGGMDVWGQGTMVTVSSGGGGSGGGGSGGGASSYELTQD<br>PAVSVALGQTVRITCQGDSLRSYYASWYQQKPGQAPVLVIYGKNNRPSGI<br>PDRFSGSSSGNTASLTITGAQAEDEADYYCNSRDSSGNHVVFGGGTKLTV<br>L (SEQ ID NO: 69) |
| 2447_<br>3C08 | EVQLLESGGGLVQPGGSLRLSCAASGFTFDDYAMHWVRQAPGKGLEWV<br>SGISWNSGSIGYADSVKGRFTISRDNAKNSLYLQMNSLRAEDTALYYCAK<br>DRGSGYEGNYYGMDVWGQGTLVTVSSGGGGSGGGGSGGGASSYELTQD<br>PAVSVALGQTVRITCQGDSLRSYYASWYQQKPGQAPVLVIYGKNNRPSGI<br>PDRFSGTTSGNTASLTITGAQAEDEADYYCNSRDSSGNHYVFGTGTKVTV<br>L (SEQ ID NO: 79) |
| 2447_<br>3H02 | EVQLLESGGGLVQPGRSLRLSCAASGFTFDDYAMHWVRQAPGKGLEWVS<br>GISWDSGSIGYADSVKGRFTISRDNAKNSLYLQMNSLRAEDTALYYCAKD<br>VSSGWYWYAFDIWGQGTLVTVSSGGGGSGGGGSGGGASSYELTQDPAVS<br>VALGQTVRITCQGDILRSYYASWYQQKPGQAPVLVIYGKNNRPSGIPDRFS<br>GSSSGNTASLTITGAQAEDEADYYCNSRDSSGNRVVFGGGTKLTVL (SEQ<br>ID NO: 89) |
| 2447_<br>3H08 | EVQLLESGGGLVQPGRSLRLSCAASGFTFDDYAMHWVRQAPGKGLEWVS<br>GISWNSGSIDYADSVKGRFTISRDNSKNTLYLQMNSLRAEDTAVYYCARD<br>RSSGWYTGSFDYWGQGTLVTVSSGGGGSGGGGSGGGASSYELTQDPAVS<br>VALGQTVRITCQGDSLRSYYASWYRQKPGQAPVLVIYGKNNRPSGIPDRF<br>SGSSSGNTASLTIIGAQAEDEADYYCQSRDSSDNRVLFGGGTKVTVL (SEQ<br>ID NO: 99) |
| G03 | EVQLVQSGAEVKKPGATVKISCKVSGYTFTSYWMHWVQQAPGKGLEWI<br>GYINPGTGYIEYNQKFKDRVTITADKSTDTAYMELSSLRSEDTAVYYCASS<br>TAPFDYWGQGTLVTVSSGGGGSGGGGSGGGASEIVLTQSPGTLSLSPGER<br>ATLSCKASQDIKSYLSWYQQKPGQAPRLLIYYATRLADGIPDRESGSGSGT<br>DFTLTISRLEPEDFAVYYCLQYDESPYTFGQGTKLEIK (SEQ ID NO: 109) |

TABLE 4

| Clone name | scFv nucleotide sequence |
| --- | --- |
| 2445_<br>1F09 | GAGGTGCAGCTGTTGGAGACTGGAGGAGGCTTGATCCAGCCTGGGGG<br>GTCCCTGAGACTCTCCTGTGCAGCCTCTGGGTTCACCGTCAGTAGCAAC<br>TACATGAGCTGGGTCCGCCAGGCTCCAGGGAAGGGGCTGGAGTGGGTC<br>TCAGTTATTTATAGCGGTGGTAGCACATATTACGCAGACTCCGTGAAG<br>GGCCGATTCACCATCTCCAGAGACAATTCCAAGAACACGCTGTATCTT<br>CAAATGAACAGCCTGAGAGCCGAGGACACGGCCGTGTATTACTGTGCG<br>AGAGATCGCGGCTGGAACCACGGTATGGACGTCTGGGGCCAGGGAAC<br>CCTGGTCACCGTCTCGAGTGGTGGAGGCGGTTCAGGCGGAGGTGGCTC<br>TGGCGGTGGCGCTAGCCAGTCTGGGCTGACTCAGCCACCCTCAGCGTC<br>TGGGACCCCCGGGCAGAGGGTCACCATCTCTTGTTCTGGGGGCAGCTC<br>AGAAGTCGGAAGTAGATATGTGTCCTGGTACCAGCAACTCCCAGGAAC<br>GGCCCCCAGACTCCTCATCTATAAGAATGATCGGCGGCCCTCAGGGGT<br>CCCTGACCGATTCTCTGGCTCCAAGTCTGGCTCCTCAGCCTCCCTGGCC<br>ATCAGTGGGCTCCGGTCGAGGATGAGGCTGATTATTACTGTGCAGCA<br>TGGGATGACAGCTGAATGGTTATGTCTTCGGAACTGGGACCAAGCTG<br>ACCGTCCTA (SEQ ID NO: 10) |
| 2447_<br>2H08 | GAAGTGCAGCTGGTGCAGTCTGGAGCTGAGGTGAAGAAGCCTGGGGC<br>CTCAGTGAAGGTCTCCTGCAAGGCTTCTGGTTACACCTTTACCAACTAC<br>GGTATCAGCTGGGTGCGACAGGCCCCTGGACAAGGGCTTGAGTGGATG<br>GGATGGATCAGCGCTTACAATGGTAACACAAACTATGCACAGAAGCTC<br>CAGGGCAGAGTCACCATGACCACAGACACATCCACGAGCACAGCCTA<br>CATGGAGCTGAGGAGCCTGAGATCTGACGACACGGCCGTGTATTACTG |

TABLE 4-continued

| Clone name | scFv nucleotide sequence |
|---|---|
| | TGCGAGAGATCCGCATATTTTGACTGGTTATTATAGGGGAGGGTGGTT<br>CGACCCCTGGGGGCAAGGGACCACGGTCACCGTCTCGAGTGGTGGAG<br>GCGGTTCAGGCGGAGGTGGCTCTGGCGGTGGCGCTAGCTCCTATGAGC<br>TGACTCAGGACCCTGCTGTGTCTGTGGCCTTGGGTCAGACAGTCACCAT<br>CACGTGCCAAGGAGACAGCCTCAGAACCTCTTATGCAGGCTGGCTCCA<br>GCAGAAGCCAGGACAGGCCCCTGTACTCGTCCTCTATGGTAAAACCAG<br>CCGGCCCTCAGGGATCCCAGACCGATTCTCTGGCTCCACCTCAGGAAA<br>CACAGCTTCCTTGACCATCACTGGGGCTCAGGCGGAGGATGAGGCTGA<br>GTATTTCTGTCACTCCCGGGACAGCAATGATAACTATCTAGAGGTGGTT<br>TTCGGCGGAGGGACCAAGCTGACCGTCCTA (SEQ ID NO: 20) |
| 2447_<br>3A01 | GAGGTGCAGCTGTTGGAGTCTGGGGGAGGCTTGGTACAGCCTGGGGGG<br>TCCCTGAGACTCTCCTGTGCAGCCTCTGGATTCACCTTTGATGATTATG<br>CCATGCACTGGGTCCGGCAAGCTCCAGGGAAGGGCCTGGAGTGGGTCT<br>CAGGTATTAGTTGGAATAGTGGTAGCATAGTCTATGCGGACTTTGTGA<br>AGGGCCGATTCACCATCTCCAGAGACAACGCCAAGAACTCCCTGTATC<br>TGCAAATGAACAGTCTGAGAGCTGAGGACACGGCCTTGTATTACTGTG<br>CAAAAGATATTTCAAGTGGCTGGTACCCAGGGACCTTTGACTACTGGG<br>GCCAGGGAACCCTGGTCACCGTCTCGAGTGGTGGAGGCGGTTCAGGCG<br>GAGGTGGCTCTGGCGGTGGCGCTAGCTCCTATGAGCTGACTCAGGACC<br>CTGCTGTGTCTGTGGCCTTGGGACAGACAGTCAGGATCACATGCCAAG<br>GAGACAGCCTCAGAAGCTATTATGCAAGCTGGTACCAGCAGAAGCCA<br>GGACAGGCCCCTGTACTTGTCATCTATGGTAAAAACAACCGGCCCTCA<br>GGGATCCCAGACCGATTCTCTGGCTCCAGCTCAGGAAACACAGCTTCC<br>TTGACCGTCACTGGGGCTCAGGCGGAAGACGAGGCTGACTATTACTGT<br>AGCTCCCGGGACAGCAGTGATGATGTGGTATTCGGCGGAGGGACCCAG<br>CTCACCGTCCTA (SEQ ID NO: 30) |
| 2447_<br>3A08 | GAAGTGCAGCTGGTGCAGTCTGGAGCTGAGGTGAAGAAGCCTGGGGC<br>CTCAGTGAAGGTCTCCTGCAAGGCTTCTGGTTACACCTTTACCAGCTAC<br>GGTATCAGCTGGGTGCGACAGGCCCCTGGACAAGGGCTTGAGTGGATG<br>GGATGGATCAGCGCTTACAATGGTAACACAAACTATGCACAGAAGCTC<br>CAGGGCAGAGTCACCATGACCACAGACACATCCACGAGCACAGCCTA<br>CATGGAGCTGAGGAGCCTGAGATCTGACGACACGGCCGTGTATTACTG<br>TGCGAGAGATCGGGCTACGATTTTTGGAGTGGTTACCCCCTTTGACTAC<br>TGGGGCCAAGGAACCCTGGTCACCGTCTCGAGTGGTGGAGGCGGTTCA<br>GGCGGAGGTGGCTCTGGCGGTGGCGCTAGCTCCTATGAGCTGACTCAG<br>GACCCCGCTGTGTCTGTGGCCTTGGGACAGACAGTCAGGATCACATGC<br>CAGGGAGACAGTATTGAAGTTATTCTGCCAGCTGGTACCAGCAGAAG<br>CCAGGGCAGGCCCCTCGCCTTGTTATCTATGGTAAAAACAACCGGCCC<br>TCAGGGATCCCAGACCGAGTCTCTGGCTCCACTTCAGGAAATACAGCT<br>TCCTTGACCGTCACTGGGGCTCAGGCGGAAGATGAGGCTGACTATTAC<br>TGTAACTCCCGGGACAGCAGTGGTAACCGTGTGGTATTCGGCGGAGGG<br>ACCCAGCTCACCGTCCTA (SEQ ID NO: 40) |
| 2447_<br>3A09 | GAGGTGCAGCTGTTGGAGTCTGGGGGAGGCTTGGTACAGCCTGGCAGG<br>TCCCTGAGACTCTCCTGTGCAGCCACTGGATTCACCTTTGATGATTATG<br>CCATGCACTGGGTCCGGCAAGCTCCAGGGAAGGGCCTGGAGTGGGTCT<br>CAGGTATTAGTTGGAATAGTGGTAGCATAGGCTATGCGGACTCTGTGA<br>AGGGCCGATTCACCATCTCCAGAGACAACGCCAAGAACTCCCTGTATC<br>TGCAAATGAACAGTCTGAGAGCTGAGGACACGGCCTCGTATTACTGTG<br>CAAAAGATGTTAGCAGTGGCTGGTACTGGTATGCTTTTGATATCTGGG<br>GCCAAGGAACCCTGGTCACCGTCTCGAGTGGTGGAGGCGGTTCAGGCG<br>GAGGTGGCTCTGGCGGTGGCGCTAGCTCCTATGAGCTGACTCAGGACC<br>CTGCTGTGTCTGTGGCCTTGGGACAGACAGTCAGGATCACATGCCAAG<br>GAGACAGCCTCAGAAGCTATTATGCAAGCTGGTACCAGCAGAAGCCA<br>GGACAGGCCCCTGTACTTGTCATCTATGGTAAAAACAACCGGCCCTCA<br>GGGATCCCAGGCCGATTCTCTGGCTCCAGCTCAGGAAACACAGCTTCC<br>TTGACCGTCACTGGGGCTCAGGCGGAAGATGAGGCTGACTATTACTGT<br>AATTCCCGGGACAGCGGTGGTTCTGTGGTTTTCGGCGGAGGGACCAAG<br>CTGACCGTCCTA (SEQ ID NO: 50) |
| 2447_<br>3A12 | GAAGTGCAGCTGGTGCAGTCTGGAGCTGAGGTGAAGAAGCCTGGGGC<br>CTCAGTGAAGGTCTCCTGCAAGGCTTCTGGTTACACCTTTACCAGCTAT<br>GGTATCAGCTGGGTGCGACAGGCCCCTGGACAAGGGCTTGAGTGGATG<br>GGATGGATCAGCGCTTACAATGGTAACACAAACTATGCACAGAAGCTC<br>CGGGGCAGAGTCACCATGACCACAGACACATCCACGAGCACAGCCTA<br>CATGGAGCTGAGGAGCCTGAGATCTGACGACACGGCCGTGTATTACTG<br>TGCGAGAGATCCGCATATTTTGACTGGTTATTATAGGGGAGGGTGGTT<br>CGACCCCTGGGGCCAGGGCACCCTGGTCACCGTCTCGAGTGGTGGAGG<br>CGGTTCAGGCGGAGGTGGCTCTGGCGGTGGCGCTAGCTCCTATGAGCT<br>GACTCAGGACCCTGCTGTGTCTGTGGTCTTGGGACAGACAGTCAGGAT<br>CACATGCCAAGGAGACAGCCTCAGAAGCTATTATGCAAGCTGGTACCA<br>GCAGAAGCCAGGACAGGCCCCTGTACTTGTCATCTATGGTAAAAACAA<br>CCGGCCCTCAGGGATCCCAGACCGATTCTCTGGCTCCAGCTCAGGAAA<br>CACAGCTTCCTTGACCATCACTGGGGCTCAGGCGGAAGATGAGGCTGA<br>CTATTACTGTAACTCCCGGGACAGCAGTGGTAACCATCGTGTATTCGG |

TABLE 4-continued

| Clone name | scFv nucleotide sequence |
|---|---|
| | CGGAGGGACCAAGCTGACCGTCCTA (SEQ ID NO: 60) |
| 2447_3B07 | CAGGTGCAGCTGGTGGAGTCTGGGGGAGTCGTGGTACAGCCTGGGGG<br>GTCCCTGAGACTCTCCTGTGCAGCCTCTGGATTCACCTTTGATGATTAT<br>GCCATGCACTGGGTCCGTCAAGCTCCGGGGAGGGGTCTGGAGTGGGTC<br>TCTCTTACTAGTTGGGATGGTGGTAGCACATACTATGCAGACTCTGTGA<br>AGGGTCGATTCACCATCTCCAGAGACAACAGCAAAAACTCCCTGTATC<br>TGCAAATGAACAGTCTGAGAGCTGAGGACACCGCCTTGTATTACTGTG<br>CAAAAGATCATAGCAGCGGCTGGTACAACGGGGGTATGGACGTCTGG<br>GGCCAAGGGACAATGGTCACCGTCTCGAGTGGTGGAGGCGGTTCAGGC<br>GGAGGTGGCTCTGGCGGTGGCGCTAGCTCCTATGAGCTGACTCAGGAC<br>CCTGCTGTGTCTGTGGCCTTGGGACAGACAGTCAGGATCACATGCCAA<br>GGAGACAGCCTCAGAAGCTATTATGCAAGCTGGTACCAGCAGAAGCC<br>AGGACAGGCCCCTGTACTTGTCATCTATGGTAAAAACAACCGGCCCTC<br>AGGGATCCCAGACCGATTCTCTGGCTCCAGCTCAGGAAACACAGCTTC<br>CTTGACCATCACTGGGGCTCAGGCGGAAGATGAGGCTGACTATTACTG<br>TAACTCCCGGGACAGCAGTGGTAACCATGTGGTATTCGGCGGAGGGAC<br>CAAGCTGACCGTCCTA (SEQ ID NO: 70) |
| 2447_3C08 | GAGGTGCAGCTGTTGGAGTCTGGGGGAGGCTTGGTACAGCCTGGGGGG<br>TCCCTGAGACTCTCCTGTGCAGCCTCTGGATTCACCTTTGATGATTATG<br>CCATGCACTGGGTCCGGCAAGCTCCAGGGAAGGGCCTGGAGTGGGTCT<br>CAGGTATTAGTTGGAATAGTGGTAGCATAGGCTATGCGGACTCTGTGA<br>AGGGCCGATTCACCATCTCCAGAGACAACGCCAAGAACTCCCTGTATC<br>TGCAAATGAACAGTCTGAGAGCTGAGGACACGGCCTTGTATTACTGTG<br>CAAAAGATAGGGGTAGTGGCTACGAAGGAAACTACTACGGTATGGAC<br>GTCTGGGGCCAAGGAACCCTGGTCACCGTCTCGAGTGGTGGAGGCGGT<br>TCAGGCGGAGGTGGCTCTGGCGGTGGCGCTAGCTCCTATGAGCTGACT<br>CAGGACCCTGCTGTGTCTGTGGCCTTGGGACAGACAGTCAGGATCACA<br>TGCCAAGGAGACAGCCTCAGAAGCTATTATGCAAGCTGGTACCAGCAG<br>AAGCCAGGACAGGCCCCTGTACTTGTCATCTATGGTAAAAACAACCGG<br>CCCTCAGGGATCCCAGACCGATTCTCTGGTACCACCTCAGGAAACACA<br>GCCTCCTTGACCATCACTGGGGCTCAGGCGGAAGATGAGGCTGACTAT<br>TACTGTAACTCCCGGGACAGCAGTGGTAACCATTATGTCTTCGGAACT<br>GGGACCAAGGTCACCGTCCTA (SEQ ID NO: 80) |
| 2447_3H02 | GAGGTGCAGCTGTTGGAGTCTGGGGGAGGCTTGGTACAGCCTGGCAGG<br>TCCCTGAGACTCTCCTGTGCAGCCTCTGGATTCACCTTTGATGATTATG<br>CCATGCACTGGGTCCGGCAAGCTCCAGGGAAGGGCCTGGAGTGGGTCT<br>CAGGTATTAGTTGGGATAGTGGTAGCATAGGCTATGCGGACTCTGTGA<br>AGGGCCGATTCACCATCTCCAGAGACAACGCCAAGAACTCCCTGTATC<br>TGCAAATGAACAGTCTGAGAGCTGAGGACACGGCCTTGTATTACTGTG<br>CAAAAGATGTTAGCAGTGGCTGGTACTGGTATGCTTTTGATATCTGGG<br>GCCAGGGAACCCTGGTCACCGTCTCGAGTGGTGGAGGCGGTTCAGGCG<br>GAGGTGGCTCTGGCGGTGGCGCTAGCTCCTATGAGCTGACTCAGGACC<br>CTGCTGTGTCTGTGGCCTTGGGACAGACAGTCAGGATCACATGCCAAG<br>GAGACATCCTCAGAAGTTATTATGCAAGTGGTACCAGCAGAAGCCAG<br>GACAGGCCCCTGTACTTGTCATTTATGGTAAAAACAACCGGCCCTCAG<br>GGATCCCAGACCGATTCTCTGGCTCCAGCTCAGGAAACACAGCTTCCT<br>TGACCATCACTGGGGCTCAGGCGGAAGATGAGGCTGACTATTACTGTA<br>ACTCCCGGGACAGCAGTGGTAACCGTGTGGTATTCGGCGGAGGGACCA<br>AGCTGACCGTCCTA (SEQ ID NO: 90) |
| 2447_3H08 | GAGGTGCAGCTGTTGGAGTCTGGGGGAGGCTTGGTACAGCCTGGCAGG<br>TCCCTGAGACTCTCCTGTGCAGCCTCTGGATTCACCTTTGATGATTATG<br>CCATGCACTGGGTCCGGCAAGCTCCAGGGAAGGGCCTGGAGTGGGTCT<br>CAGGTATTAGTTGGAATAGTGGTAGCATAGACTATGCAGACTCCGTGA<br>AGGGCCGATTCACCATCTCCAGAGACAATTCCAAGAACACGCTGTATC<br>TGCAAATGAACAGCCTGAGAGCTGAGGACACAGCTGTGTACTACTGTG<br>CGAGAGATCGGAGTAGTGGCTGGTACACGGGGTCCTTTGACTACTGGG<br>GCCAGGGCACCCTGGTCACCGTCTCGAGTGGTGGAGGCGGTTCAGGCG<br>GAGGTGGCTCTGGCGGTGGCGCTAGCTCCTATGAGCTGACTCAGGACC<br>CTGCTGTGTCTGTGGCCTTGGGACAGACAGTCAGGATCACATGCCAAG<br>GAGACAGCCTCAGAAGCTATTATGCAAGCTGGTACCGGCAGAAGCCA<br>GGACAGGCCCCTGTACTTGTCATCTATGGTAAAAACAACCGGCCCTCA<br>GGGATCCCAGACCGATTCTCTGGCTCCAGCTCGGGAAACACAGCTTCC<br>TTGACCATCATTGGGGCTCAGGCGGAAGACGAGGCTGACTATTACTGT<br>CAGTCCCGGGACAGCAGTGATAACCGTGTTCTATTCGGCGGAGGGACC<br>AAGGTCACCGTCCTA (SEQ ID NO: 100) |

Affinity of scFv-Fc antibody including the scFv for mucin1 antigen was measured using Biacore T200 (GE healthcare). Anti-human IgG (Fc) antibody (GE healthcare, Cat. No. BR-1008-39, final concentration of 25 ug/mL) was applied at a rate of 5 uL/min for 360 seconds on a Series S Sensor Chip CM5 (GE healthcare, Cat. No. BR-1005-30) using an Amine Coupling Kit (GE healthcare, Cat. No. BR-1000-50) and immobilized at about 5000-7000 RU. Human MUC1 protein as the antigen was injected at a rate of 30 μL/min at different five concentrations from 25 nM to 400 nM, and $k_a$ and $k_d$ values were obtained as in the following Table, and $K_D$ values were calculated therefrom. As a result, $K_D$ (M) values indicating binding affinity for mucin1 are shown in Table 5.

TABLE 5

| Clone name | $K_D$ (M) |
|---|---|
| 2447_2H08 | $94.8 \times 10^{-9}$ |
| 2447_3A01 | $51.5 \times 10^{-9}$ |
| 2447_3A08 | $320.3 \times 10^{-9}$ |
| 2447_3A09 | $62.1 \times 10^{-9}$ |
| 2447_3A12 | $13.8 \times 10^{-9}$ |
| 2447_3B07 | $51.7 \times 10^{-9}$ |
| 2447_3C08 | $24.0 \times 10^{-9}$ |
| 2447_3H02 | $58.8 \times 10^{-9}$ |
| 2447_3H08 | $39.9 \times 10^{-9}$ |
| G03 | $27.6 \times 10^{-9}$ |

Example 2. Preparation of CAR-T Cells Using scFv Binding to Mucin1

2-1. Preparation of CAR-Expressing Lentivirus Transfer Vector

A lentivirus vector (transfer vector or expression vector) expressing a chimeric antigen receptor (CAR) comprising an extracellular domain comprising the scFv polypeptide sequence (a nucleotide sequence of Table 4), a hinge (CD8a) (SEQ ID NO: 112), and a transmembrane domain (CD28) (SEQ ID NO: 113), a co-stimulatory domain (CD28) (SEQ ID NO: 114), and an intracellular signaling domain (CD3 zeta) (SEQ ID NO: 115) was prepared. The scFv region of CAR was isolated by PCR from a plasmid supplied by the screening company, and the hinge, transmembrane protein, and CD28 and CD3z signaling domains were isolated from the synthesized plasmid by PCR. Two fragments were cloned into a Clonetech's pLVX-EF1alpha vector using a Takara's In-Fusion HD cloning kit. The lentivirus vector thus cloned was transfected into Takara's Lenti-X 293T cell line (product code 632180) together with a packaging plasmid provided by the same company's Lenti-X Expression System (EF1a Version) (product code 631253), and 24 hours later, the soup was separated and the lentivirus therein was used for further research.

2-2. Production of Lentivirus Particles

To produce the lentivirus, the lentivirus transfer vector (transfer vector or expression vector) prepared above and a packaging plasmid mix were transfected into Lenti-X 293T cells (Takara product no. 632180) using a liposome nucleic acid transfection reagent (lipofectamine, Gibco). One day before transfection, HEK293T cells were prepared at confluency of about 6% to 70% of a culture plate area. Dulbecco's modified Eagle medium (DMEM, Gibco) supplemented with 10% heat-inactivated fetal bovine serum (FBS, Gibco) was used as a medium, and a culture plate of 100 mm or 150 mm in size was used. Culture conditions were maintained at 37° C., 5% $CO_2$, and humidified conditions. The transfer vector, the lentivirus packaging plasmid mix, and the liposome nucleic acid transfection reagent were mixed at room temperature by adjusting their ratio according to the manufacturer's instructions, and dropped on the HEK293T cells on the plate during culture to transfect the HEK293T cells. After transfection, the lentiviruses produced in the HEK293T cells were burst out of the cells and was present in the form of virus particles in the cell culture. 48 hours after transfection, only the cell culture solution was removed from the culture plate and centrifuged to obtain lentivirus particles in the form of pellet. The pellet was suspended using a solution, which was then immediately used or stored in a cryogenic freezer. As the solution, a DMEM medium used above, or a solution was used, which was prepared by adding Optimizer T-Cell Expansion Supplement (26 ml) to a 1 L bottle of CTS optimizer T cell Expansion SFM (Gibco) used in T cell culture, adding CTS Immune Cell SR (Serum Replacement, Gibo) at a final concentration of 2%, and then adding CTS GlutaMAX-I Supplement 100x (Gibco) at a final concentration of 1x.

2-3. Preparation of CAR-T Cell

Peripheral blood mononuclear cell (PBMC) samples were supplied through a research agreement with the Catholic University of Korea, and donor recruitment and blood collection were carried out with the approval of the Catholic University of Korea-Institutional Review Board. All blood was of normal people. In exemplary embodiments of the present disclosure, "Donor" refers to the donor of the PBMC sample used in the experiment, and the number after Donor means that the donor is different (for example, indicated by Donor 03, Donor 04, Donor 05, Donor 06, Donor 07, Donor 08, Donor 18-09, Donor 20-01, etc.). To prepare CAR-T cells expressing the chimeric antigen receptor (CAR) on the surface of T cells, frozen PBMC vials were thawed in a water bath at 37° C. The next day after thawing of frozen PBMCs, the number of cells was counted, followed by replacement with a fresh medium. At the same time, T-cells were activated using T cell-specific expansion beads (Dynabeads Human T-expander CD3/CD28, Gibco), and chimeric antigen receptor (CAR) in the form of lentivirus was transduced by treating T cells according to the number of activated cells. In order to culture the transduced T cells, a suspension of interleukin-2 (Norvatis) in filtered sterile distilled water was added at 100 IU/ml, based on the amount of the medium, and during the subsequent culture period, the suspension was continuously added when the medium was replaced or added. The cell culture period was 10 days to 11 days in total after activation, and cell culture was performed while replacing or newly adding the medium every 1-2 days depending on the number of cells. At the end of the culture period, the cell culture was completed and CAR-T cell production was completed. The prepared CAR-T cells were used immediately, or mixed with a cell cryopreservation solution and injected into a vial for cell freezing and stored in a liquid nitrogen tank. The expression levels of the chimeric antigen receptor (CAR) of the prepared CAR-T cells and characteristics thereof were analyzed by flow cytometry (FACS).

Example 3. Analysis of Affinity of Soluble scFv to Mucin1-Expressing Cell

Hereinafter, unless otherwise specified, information on cell lines used in the present exemplary embodiment is as follows:

PANC-1; Korean Cell Line Bank, 21469
HCC1954; Korean Cell Line Bank, 9S1954
HCC70; Korean Cell Line Bank, 9S0070
T47D; Korean Cell Line Bank, 30133
HEK293T; ATCC, CRL-3216
Huh7; Korean Cell Line Bank, 60104
HepG2; ATCC, HB-8065
SK-N-SH; Korean Cell Line Bank, 30011

A total of 4 cell lines were used in Example 3, and among them, HEK293 (ATCC) and PANC-1 (ATCC) cell lines were used as negative controls, and HEK293T-v1 (ATCC and transformed by LG Chem) and T47D (Korean Cell Line Bank) were used as positive controls. HEK293T-v1 cell line used as the positive control is a cell line obtained by expressing C subunit of MUC1 in HEK293T cell line not expressing mucin1. 11 types of scFvs were used, and among them, a positive control was G03 (Table 3). The soluble scFv prepared in Example 1 was diluted 5-fold to prepare a total of 8 serial dilutions. Each serial dilution was 380 µg/mL, 76 µg/mL, 15.2 µg/mL, 3.04 µg/mL, 0.608 µg/mL, 0.1216 µg/mL, 0.02432 µg/mL, 0.004864 µg/mL. A buffer used in soluble scFv dilution and cell washing was PBS containing 2% FBS and 10 mM EDTA. Four kinds of cells were prepared at a density of $1 \times 10^6$/mL, respectively, and put in a 96 well U-bottom cell culture plate at a density of $1 \times 10^5$/100 µl/well, followed by centrifugation at 1500 RPM for 5 minutes. The soluble scFv prepared previously was treated in an amount of 50 µl/well. The cells were left at 4° C. for 1 hour. 150 µl/well of the cell washing buffer was added thereto and then mixed, followed by centrifugation at 1500 RPM for 5 minutes. The supernatant was discarded, and 200 µl/well of the cell washing buffer was added thereto and then mixed, followed by centrifugation at 1500 RPM for 5 minutes. A goat anti-human IgG Fc-biotin antibody (Invitrogen, A18821) was diluted 500-fold, and 50 µl/well thereof was treated. The cells were left at 4° C. for 20 minutes. 150 µl/well of the cell washing buffer was added thereto and then mixed, followed by centrifugation at 1500 RPM for 5 minutes. The supernatant was discarded, and 200 µl/well of the cell washing buffer was added thereto and then mixed, followed by centrifugation at 1500 RPM for 5 minutes. PE-Streptavidin (BD Pharmigen, 554061) was diluted 1000-fold, and 50 µl/well thereof was treated. The cells were left at 4° C. for 20 minutes. 150 µl/well of the cell washing buffer was added thereto and then mixed, followed by centrifugation at 1500 RPM for 5 minutes. The supernatant was discarded, and 200 µl/well of the cell washing buffer was added thereto and then mixed, followed by centrifugation at 1500 RPM for 5 minutes. 80 µl/well of the cell washing buffer was added and mixed, followed by flow cytometry.

The affinity of the soluble scFv to the mucin1-expressing cells was confirmed by PE MFI values from the results of the flow cytometry. Each cell line without soluble scFv was stained with another fluorescent antibody (Goat anti-human IgG Fc-biotin antibody, PE-Streptavidin), which was used as a negative control value, and each cell line was treated with G03 at a concentration of 380 µg/mL, which was used as a positive control value, and MFI value was corrected as follows:

$$\text{(Experimental Value–Negative Control Value)/(Positive Control Value–Negative Control Value)} \times 100 = \text{Correction value of Experimental Value}$$

$EC_{50}$ was calculated using the corrected values, and the described results are the results of two cell lines used as positive controls (Table 6).

TABLE 6

| Clone name | $EC_{50}$ (293T-v1) (ug/ml) | $EC_{50}$ (T47D) (ug/ml) |
|---|---|---|
| G03 | 3.46 | 3.56 |
| 2445_1F09 | $1.51 \times 10^7$ | $6.19 \times 10^7$ |
| 2447_3A01 | 4.78 | 11.14 |
| 2447_3A08 | 1.73 | 3.76 |
| 2447_3A09 | 1.96 | 2.2 |
| 2447_3A12 | 1.47 | 0.75 |
| 2447_3C08 | 1.38 | 2.04 |
| 2447_3H02 | 1.41 | 1.6 |

TABLE 6-continued

| Clone name | $EC_{50}$ (293T-v1) (ug/ml) | $EC_{50}$ (T47D) (ug/ml) |
|---|---|---|
| 2447_3H08 | 2.57 | 5.6 |
| 2447_2H08 | 21.73 | 130.4 |
| 2447_3B07 | 3.86 | 3.47 |

Example 4. Analysis of Cytokine Secretion of CAR-T Cells

Responses of immune cells (T cells), into which anti MUC1 scFv was injected in the form of CAR, for MUC1-positive tumor cells (T47D, HEK293T-V1) were evaluated. T47D cells naturally expressing high levels of MUC1, and HEK293T-V1 cells overexpressing C subunit of human MUC1 were co-cultured with a total of 10 kinds of immune cells, 2445_1F09, 2447_3A01, 2447_3A08, 2447_3A09, 2447_3A12, 2447_3C08, 2447_3H02, 2447_3H08, 2447_2H08, 2447_3B07 prepared according to Example 2 (in some drawings, abbreviated as 1F09, 3A01, 3A08, 3A09, 3A12, 3C08, 3H02, 3H08, 2H08, 3B07, respectively), into which anti MUC1 scFv was injected in the form of CAR, at a ratio of tumor cell:immune cell of 1:1.5 for 24 hours. Concentrations of two kinds of cytokines, i.e., interferon-gamma (IFNg) and interleukin-2 (IL-2) in the culture media obtained therefrom were examined by ELISA. ELISA was performed in the same manner as the method commonly used, and briefly, as follows. First, a 96-well plate was coated with a capture antibody capable of capturing interferon-gamma or interleukin-2. 1 day later, the plate was sufficiently washed with a washing buffer. A block buffer was added to each well, and left at room temperature for 1 hour, followed by sufficiently washing with the washing buffer. In order to know the absolute value, along with a standard solution of known concentration, a culture solution sample was added to each well, left at room temperature for 2 hours, and allowed to react. The plate was sufficiently washed with the washing buffer, and then a detection antibody was added thereto and allowed to react at room temperature for 2 hours. The plate was sufficiently washed with the washing buffer, and then an HRP-conjugated streptavidin was added to each well, and allowed to react at room temperature for 20 minutes. The plate was sufficiently washed with the washing buffer, and then a substrate solution was added, and allowed to react at room temperature for 20 minutes. The reaction was stopped with a stop solution. The cytokine concentration in each well was calculated by absorbance according to reaction.

In FIG. 1, G03 indicates a positive control, and as a negative control, a group (NO LV) into which no CAR was injected was used. In addition, FIG. 1 shows representative graphs showing the results of independent experiments using a total of two kinds of T cells, in which they were named Donor 03 and Donor 04 according to the origin of T cells. In the present exemplary embodiment, "Donor" refers to the donor of the T cell used in the experiment, and the number after Donor means that the donor is different. FIG. 1 shows graphs in which the absorbance was normalized, based on the control G03, showing that the tested immune cells secreted cytokines.

FIG. 2 shows results of cytokine secretion analysis evaluating responses of immune cells, into which anti-MUC1 scFv was injected in the form of CAR, for MUC1-positive tumor cells (T47D), showing that the tested immune cells secreted cytokines. T cells were derived from Donor 06. A group (Control T cell) into which no CAR was injected was used as a negative control.

FIG. 3 shows results of cytokine secretion analysis evaluating responses of immune cells, into which anti-MUC1 scFv was injected in the form of CAR, for cells not expressing mucin1 (HEK293T), showing that the immune cells did not secrete interferon gamma cytokine, and the secretion amount of IL-2 did not increase significantly, as compared to that of the negative control (Control T cell). T cells were derived from Donor 06. A group (Control T cell) into which no CAR was injected was used as the negative control.

Example 5. Analysis of Cytotoxicity of CAR-T Cell

Human breast cancer cell lines (T47D, HCC70, HCC1954), human liver cancer cell lines (Huh7, HepG2), and a human neuroblastoma cell line (SK-N-SH) were purchased from Korean Cell Line Bank (KCLB, Seoul, Korea), and a human embryonic kidney cell line (HEK293T) was purchased from American Type Culture Collection (ATCC, Manassas, VA). T47D, HCC70, and HCC1954 cells were cultured in an RPMI-1640 medium (Thermo Fisher Scientific), and HEK293T, Huh7, and HepG2 were cultured in a Dulbecco's modified Eagle's medium (DMEM, Thermo Fisher Scientific), respectively. All media were used after supplemented with 10% (w/v) heat inactivated fetal bovine serum (FBS, Thermo Fisher Scientific). All cells were cultured under conditions of 37° C. and 5% $CO_2$. CAR-T cells prepared according to Example 2 were cultured in a CTS complete medium (CTS™ OpTmizer™ T Cell Expansion SFM (Gibco, A1048501), 2% (w/v) CTS™ Immune Cell SR (Gibco, A25961-01), 1× GlutaMAX™ Supplement (Gibco, 35050-061)) under conditions of 37° C. and 5% $CO_2$.

To analyze mucin1-specific cytotoxicity of CAR-T cells, cell lysis was measured for mucin1-expressing cells (including T47D, HCC70, HCC1954, HEK293T-V1 (exogenous MUC1-C-expressing cell), etc.) and cells not expressing mucin1 (including HEK293T, HepG2, Huh7, SK-N-SH, etc.) by the following method. First, target cells expressing or not expressing mucin1, which were stained with Cell-Trace™ CFSE (Invitrogen, C34554), were dispensed at a density of 0.15~0.2×10⁶ cells/150 µl/well, and cultured for one day. On the same day, CAR-T cells frozen and stored at −196° C. were thawed, and cultured at a density of 2×10⁶ cells/ml for one day in a CTS complete medium containing 30 U/ml of IL-2 (Novartis, Proleukin). The next day, the CAR expression rate of CAR-T cells during culture was measured by staining with Alexa Fluor 488-AffiniPure Goat Anti-Human IgG, F(ab')2 Fragment Specific (Jackson laboratory, 109-545-097) and APC Mouse Anti-Human CD3 (BD Pharmingen™, 561811), and obtaining the percentage of cells positive for both of them using a flow cytometer (FACS). Each type of CAR-T (E, effector cells), adjusted to have the same number of CAR+ T cells, based on the CAR expression rate, was prepared in a volume of 100 µl/well using a cell culture medium of each target cell, and added in proportion to the number of CFSE-stained cells expressing or not expressing mucin1 (T, target cells) cultured the day before. The cells were cultured under conditions of 37° C., 5% $CO_2$ for 5 hours up to 24 hours depending on the target cells. Thereafter, the CAR-T cells and target cells were all taken, and stained with Fixable Viability Dye eFluor™ 450 (eBioscience™, 65-0863-18), APC Mouse Anti-Human CD3. Then, the number of live target cells was obtained using a flow cytometer. In this regard, the number of live target cells was determined by Fixable Viability Dye-negative, CFSE-positive cells. Killing activity (%) was calculated by the following equation:

$$\text{Killing activity} =$$
$$100 - (\text{the number of live Target cells in } (T \text{ cell} + \text{Target cell}) \text{ well}/$$
$$\text{the number of live Target cells in (Target cell) well} \times 100)(\%)$$

The results are shown in FIGS. 4 to 8. In the drawings, G03 represents a positive control, and as a negative control, a group (NO LV) into which no CAR was injected was used. Further, these drawings show representative graphs showing the results of independent experiments using a total of two kinds of T cells, in which they were named Donor 03 and Donor 04 according to the origin of T cells. As shown in FIGS. 4 to 8, the tested immune cells exhibited cytotoxicity against mucin1-expressing cells.

FIGS. 9 and 10 show experimental results of cytotoxicity of CAR-T cells prepared by using Donor 05- and Donor 06-derived T cells against a human breast cancer cell line T47D, FIG. 11 shows experimental results of cytotoxicity of CAR-T cells prepared by using Donor 07-derived T cells against a human embryonic kidney cell line HEK293T, and FIG. 12 shows experimental results of cytotoxicity of CAR-T cells prepared by using Donor 08-derived T cells against a human breast cancer cell line HCC70. As shown in FIGS. 9 to 12, the tested immune cells exhibited cytotoxicity against mucin1-expressing cells.

Example 6. Analysis of Mucin1-Specific Cytotoxicity of CAR-T Cell

To examine whether CAR-T cells are able to differentiate normal cells from cancer cells according to the difference in the amount of antigen, cell lysis of a breast cancer cell line (HCC70) and a human normal breast cell line (MCF10A) was measured as follows: First, HCC70 cells overexpressing mucin1 and MCF10A cells expressing low levels of mucin1 were stained with different concentrations of CellTrace™ CFSE (Invitrogen, C34554), and mixed at different ratios, respectively. The ratios of HCC70: MCF10A were 0:0.2, 0.025:0.175, 0.05:0.15, 0.075:0.125, 0.1:0.1, 0.125:0.075, 0.15:0.05, 0.175:0025, 0.2:0. The cells mixed at the predetermined ratios were dispensed at a density of 0.2×10⁶ cells/500 µl/well, and cultured for one day. On the same day, CAR-T cells (Donor 05-derived T cells expressing CAR containing 2447_2H08 scFv) frozen and stored at −196° C. were thawed, and cultured at a density of 2×10⁶ cells/ml for one day in a CTS complete medium containing 30 U/ml of IL-2 (Novartis, Proleukin). The next day, the CAR (CAR containing 2447_2H08 scFv) expression rate of CAR-T cells during culture was measured by staining with Alexa Fluor 488-AffiniPure Goat Anti-Human IgG, F(ab')2 Fragment Specific (Jackson laboratory, 109-545-097) and APC Mouse Anti-Human CD3 (BD Pharmingen™, 561811), and obtaining the percentage of cells positive for both of them using a flow cytometer (FACS). Each type of CAR-T (E, effector cells), adjusted to have the same number of CAR+ T cells, based on the CAR expression rate, was prepared in a volume of 100 µl/well using a cell culture medium of each target cell, and added in proportion to the number of CFSE-stained cells expressing or not expressing mucin1 (T, target cells) cultured the day before. The cells were cultured under conditions of 37° C., 5% $CO_2$ for 24 hours in the target cells. Thereafter, the CAR-T cells and target cells were all taken, and stained with Fixable Viability Dye eFluor™ 450 (eBio-science™, 65-0863-18), APC Mouse Anti-Human CD3. Then, the number of live target cells was obtained using a flow cytometer. In this regard, the number of live target cells was determined by Fixable Viability Dye-negative, CFSE-positive cells (HCC70 by strong CFSE signal and MCF10A by weak CFSE signal). Killing activity (%) was calculated in the same manner as in Example 5.

The results are shown in FIGS. 13 and 14. In the drawings, as a negative control, a group (mock T cell) into which no CAR was injected was used. As shown in FIGS. 13 to 14, CAR-T cells having 2447_2H08 scFv (in the drawings, each indicated by #2-CAR-T) exhibited cell killing activity against the breast cancer cell line (HCC70) overexpressing mucin1, whereas they exhibited no cytotoxicity or remarkably reduced cytotoxicity against the normal breast cell line (MCF10A) expressing low levels of mucin1.

Example 7. Analysis of Anticancer Efficacy of CAR-T Cell Using Animal Model 7-1. Analysis of anticancer efficacy using pancreatic cancer animal model 7-week-old NOG female mice were subcutaneously (s.c.) injected with $6\times10^6$ PANC1-v1 cells (PANC1 pancreatic cancer cells expressing MUC1). When the tumor volume reached 500 mm$^3$, $1\times10^6$ anti-MUC1 CAR-T cells (Donor 18-09-derived T cells expressing scFv-containing CAR according to the present disclosure) were intravenously (i.v.) injected, and then tumor growth was observed. 14 days and 28 days after CAR-T cell injection, blood was collected, and the number of human immune cells (hCD45+ cells) in the blood was observed (n=5 per group). As negative controls, a PBS (Vehicle)-injected group, and T cells not expressing CAR (Control T cell) were used.

As a result, as shown in FIGS. 15 and 16, it was observed that tumor of 500 mm$^3$ in size became small, and about 20 days after T cell injection, no tumor was observed in appearance. In contrast, in the negative controls, the tumor size continued to increase.

Next, in the same animal model, when the tumor volume exceeded 1500 mm$^3$ (i.e., 66 days after PANC1-v1 cell injection), $1\times10^6$ or $0.5\times10^6$ anti-MUC1 CAR-T cells were intravenously (i.v.) injected, and then tumor growth was observed (n=2 per group).

As a result, as shown in FIG. 17, the tumor size increased in the early stage. However, after about 10 days, the size gradually decreased, and after 30 days, the tumor size became too small to measure.

7-2. Analysis of Anticancer Efficacy Using Breast Cancer Animal Model 9-week-old NOG female mice were subcutaneously (s.c.) injected with $4\times10^6$ HCC1954 cells (breast cancer cell line naturally expressing MUC1). When the tumor volume reached 500 mm$^3$ (23 days after cell injection), $0.5\times10^6$ or $0.1\times10^6$ anti-MUC1 CAR-T cells (Donor 20-01-derived T cells expressing scFv-containing CAR according to the present disclosure) were intravenously (i.v.) injected, and then tumor growth was observed (n=7 per group). After T cell injection, blood was collected at regular intervals, and the number of human immune cells (hCD45+ cells) in the blood was observed (n=3 per group). As negative controls, a PBS (Vehicle)-injected group, and T cells not expressing CAR (Control T cell) were used.

As a result, as shown in FIGS. 18 and 19, the tumor of 500 mm$^3$ in size remained stagnant for 7 days after CAR-T cell injection. Thereafter, the size rapidly decreased, and became too small to measure after 25 days. In addition, the number of hCD45+ cells in the mouse blood tended to increase, and the number gradually decreased after about 25 days. It seems that CAR-T cells were activated and proliferated after recognizing the antigen, and thus the number of cells in the blood increased.

Based on the above description, it will be understood by those skilled in the art that the present disclosure may be implemented in a different specific form without changing the technical spirit or essential characteristics thereof. In this regard, it should be understood that the above embodiment is not limitative, but illustrative in all aspects. The scope of the disclosure is defined by the appended claims rather than by the description preceding them, and therefore all changes and modifications that fall within metes and bounds of the claims, or equivalents of such metes and bounds are therefore intended to be embraced by the claims.

The invention claimed is:

1. An antibody or an antigen-binding fragment thereof binding to mucin1, the antibody or antigen-binding fragment thereof comprising a pair of a heavy chain variable (VH) region and a light chain variable (VL) region selected from the following VH and VL regions:

a VH region comprising complementarity-determining region (CDR) 1, CDR 2, and CDR 3 comprising amino acid sequences of SEQ ID NO: 1, SEQ ID NO: 2, and SEQ ID NO: 3, respectively, and a VL region comprising CDR 1, CDR 2, and CDR 3 comprising amino acid sequences of SEQ ID NO: 4, SEQ ID NO: 5, and SEQ ID NO: 6, respectively;

a VH region comprising CDR 1, CDR 2, and CDR 3 comprising amino acid sequences of SEQ ID NO: 11, SEQ ID NO: 12, and SEQ ID NO: 13, respectively, and a VL region comprising CDR 1, CDR 2, and CDR 3 comprising amino acid sequences of SEQ ID NO: 14, SEQ ID NO: 15, and SEQ ID NO: 16, respectively;

a VH region comprising CDR 1, CDR 2, and CDR 3 comprising amino acid sequences of SEQ ID NO: 21, SEQ ID NO: 22, and SEQ ID NO: 23, respectively, and a VL region comprising CDR 1, CDR 2, and CDR 3 comprising amino acid sequences of SEQ ID NO: 24, SEQ ID NO: 25, and SEQ ID NO: 26, respectively;

a VH region comprising CDR 1, CDR 2, and CDR 3 comprising amino acid sequences of SEQ ID NO: 31, SEQ ID NO: 32, and SEQ ID NO: 33, respectively, and a VL region comprising CDR 1, CDR 2, and CDR 3 comprising amino acid sequences of SEQ ID NO: 34, SEQ ID NO: 35, and SEQ ID NO: 36, respectively;

a VH region comprising CDR 1, CDR 2, and CDR 3 comprising amino acid sequences of SEQ ID NO: 41, SEQ ID NO: 42, and SEQ ID NO: 43, respectively, and a VL region comprising CDR 1, CDR 2, and CDR 3 comprising amino acid sequences of SEQ ID NO: 44, SEQ ID NO: 45, and SEQ ID NO: 46, respectively;

a VH region comprising CDR 1, CDR 2, and CDR 3 comprising amino acid sequences of SEQ ID NO: 51, SEQ ID NO: 52, and SEQ ID NO: 53, respectively, and a VL region comprising CDR 1, CDR 2, and CDR 3 comprising amino acid sequences of SEQ ID NO: 54, SEQ ID NO: 55, and SEQ ID NO: 56, respectively;

a VH region comprising CDR 1, CDR 2, and CDR 3 comprising amino acid sequences of SEQ ID NO: 61, SEQ ID NO: 62, and SEQ ID NO: 63, respectively, and a VL region comprising CDR 1, CDR 2, and CDR 3 comprising amino acid sequences of SEQ ID NO: 64, SEQ ID NO: 65, and SEQ ID NO: 66, respectively;

a VH region comprising CDR 1, CDR 2, and CDR 3 comprising amino acid sequences of SEQ ID NO: 71, SEQ ID NO: 72, and SEQ ID NO: 73, respectively, and a VL region comprising CDR 1, CDR 2, and CDR 3 comprising amino acid sequences of SEQ ID NO: 74, SEQ ID NO: 75, and SEQ ID NO: 76, respectively;

a VH region comprising CDR 1, CDR 2, and CDR 3 comprising amino acid sequences of SEQ ID NO: 81, SEQ ID NO: 82, and SEQ ID NO: 83, respectively, and a VL region comprising CDR 1, CDR 2, and CDR 3 comprising amino acid sequences of SEQ ID NO: 84, SEQ ID NO: 85, and SEQ ID NO: 86, respectively; or a VH region comprising CDR 1, CDR 2, and CDR 3 comprising amino acid sequences of SEQ ID NO: 91, SEQ ID NO: 92, and SEQ ID NO: 93, respectively, and a VL region comprising CDR 1, CDR 2, and CDR 3 comprising amino acid sequences of SEQ ID NO: 94, SEQ ID NO: 95, and SEQ ID NO: 96, respectively.

2. The antibody or antigen-binding fragment thereof of claim 1, comprising a pair of a heavy chain variable (VH) region and a light chain variable (VL) region selected from the following VH and VL regions:

a VH region comprising an amino acid sequence of SEQ ID NO: 7 and a VL region comprising an amino acid sequence of SEQ ID NO: 8;

a VH region comprising an amino acid sequence of SEQ ID NO: 17 and a VL region comprising an amino acid sequence of SEQ ID NO: 18;

a VH region comprising an amino acid sequence of SEQ ID NO: 27 and a VL region comprising an amino acid sequence of SEQ ID NO: 28;

a VH region comprising an amino acid sequence of SEQ ID NO: 37 and a VL region comprising an amino acid sequence of SEQ ID NO: 38;

a VH region comprising an amino acid sequence of SEQ ID NO: 47 and a VL region comprising an amino acid sequence of SEQ ID NO: 48;

a VH region comprising an amino acid sequence of SEQ ID NO: 57 and a VL region comprising an amino acid sequence of SEQ ID NO: 58;

a VH region comprising an amino acid sequence of SEQ ID NO: 67 and a VL region comprising an amino acid sequence of SEQ ID NO: 68;

a VH region comprising an amino acid sequence of SEQ ID NO: 77 and a VL region comprising an amino acid sequence of SEQ ID NO: 78;

a VH region comprising an amino acid sequence of SEQ ID NO: 87 and a VL region comprising an amino acid sequence of SEQ ID NO: 88; or a VH region comprising an amino acid sequence of SEQ ID NO: 97 and a VL region comprising an amino acid sequence of SEQ ID NO: 98.

3. The antibody or antigen-binding fragment thereof of claim 1, wherein the antibody or antigen-binding fragment thereof is a single chain variable fragment (scFv), a peptibody, a fragment antigen binding (Fab), a monoclonal antibody, a bispecific antibody, a minibody, a domain antibody, a synthetic antibody, a chimeric antibody, a humanized antibody, a human antibody, or an antibody fusion protein.

4. The antibody or antigen-binding fragment thereof of claim 1, wherein the VH region and the VL region are linked to each other via a linker.

5. The antibody or antigen-binding fragment thereof of claim 4, wherein an amino acid sequence of the linker is GGGGSGGGGSGGGAS of SEQ ID NO: 116.

6. The antibody or antigen-binding fragment thereof of claim 1, wherein the antibody or antigen-binding fragment thereof is a single chain variable fragment (scFv) and the scFv includes an amino acid sequence selected from the group consisting of SEQ ID NO: 9, SEQ ID NO: 19, SEQ ID NO: 29, SEQ ID NO: 39, SEQ ID NO: 49, SEQ ID NO: 59, SEQ ID NO: 69, SEQ ID NO: 79, SEQ ID NO: 89, and SEQ ID NO: 99.

7. An isolated polynucleotide encoding the antibody or antigen-binding fragment of claim 1.

8. A vector comprising the polynucleotide of claim 7.

9. A cell comprising the vector of claim 8.

10. A chimeric antigen receptor comprising the antibody or antigen-binding fragment of claim 1.

11. The chimeric antigen receptor of claim 10, comprising an extracellular domain comprising the antibody or antigen-binding fragment; a transmembrane domain; and an intracellular signaling domain.

12. The chimeric antigen receptor of claim 11, wherein the extracellular domain further comprises a spacer region between the antibody or antigen-binding fragment and the transmembrane domain.

13. The chimeric antigen receptor of claim 12, wherein the spacer region comprises a hinge region of CD8α or CD28, or all or part of a constant region of an immunoglobulin (IgG).

14. The chimeric antigen receptor of claim 11, wherein the transmembrane domain is a transmembrane domain of CD28 or CD8.

15. The chimeric antigen receptor of claim 11, wherein the intracellular signaling domain is a CD3 zeta signaling domain.

16. The chimeric antigen receptor of claim 11, further comprising at least one co-stimulatory domain.

17. The chimeric antigen receptor of claim 16, wherein the at least one co-stimulatory domain is placed between the transmembrane domain and the intracellular signaling domain.

18. The chimeric antigen receptor of claim 16, wherein the at least one co-stimulatory domain is a signaling domain of CD28, OX-40, 4-1BB (CD137), CD27, or ICOS.

19. An isolated polynucleotide encoding the chimeric antigen receptor of claim 10.

20. A vector comprising the polynucleotide of claim 19.

21. An immune cell expressing a chimeric antigen receptor comprising the polynucleotide according to claim 19.

22. The immune cell of claim 21, wherein the immune cell is a T cell, a tumor infiltrating lymphocyte (TIL), a natural killer (NK) cell, a TCR-expressing cell, a dendritic cell, or an NK-T cell.

23. The immune cell of claim 21, wherein the immune cell is an autologous T cell or an allogenic T cell.

24. A composition comprising the antibody or antigen-binding fragment of claim 1.

25. A composition comprising the isolated polynucleotide according to claim 7.

26. A composition comprising the vector according to claim 8.

27. A composition comprising the cell according to claim 9.

28. A composition comprising the chimeric antigen receptor according to claim 10.

29. A composition comprising the isolated polynucleotide according to claim 19.

30. A composition comprising the vector according to claim 20.

31. A composition comprising the immune cell according to claim 21.

* * * * *

SEQUENCE LISTING

```
<160> NUMBER OF SEQ ID NOS: 121

<210> SEQ ID NO 1
<211> LENGTH: 8
<212> TYPE: PRT
<213> ORGANISM: Artificial Sequence
<220> FEATURE:
<223> OTHER INFORMATION: 2445_1F09 HCDR1

<400> SEQUENCE: 1

Gly Phe Thr Val Ser Ser Asn Tyr
1               5

<210> SEQ ID NO 2
<211> LENGTH: 7
<212> TYPE: PRT
<213> ORGANISM: Artificial Sequence
<220> FEATURE:
<223> OTHER INFORMATION: 2445_1F09 HCDR2

<400> SEQUENCE: 2

Ile Tyr Ser Gly Gly Ser Thr
```

```
1               5
```

<210> SEQ ID NO 3
<211> LENGTH: 10
<212> TYPE: PRT
<213> ORGANISM: Artificial Sequence
<220> FEATURE:
<223> OTHER INFORMATION: 2445_1F09 HCDR3

<400> SEQUENCE: 3

```
Asp Arg Gly Trp Asn His Gly Met Asp Val
1               5                   10
```

<210> SEQ ID NO 4
<211> LENGTH: 8
<212> TYPE: PRT
<213> ORGANISM: Artificial Sequence
<220> FEATURE:
<223> OTHER INFORMATION: 2445_1F09 LCDR1

<400> SEQUENCE: 4

```
Ser Ser Glu Val Gly Ser Arg Tyr
1               5
```

<210> SEQ ID NO 5
<211> LENGTH: 3
<212> TYPE: PRT
<213> ORGANISM: Artificial Sequence
<220> FEATURE:
<223> OTHER INFORMATION: 2445_1F09 LCDR2

<400> SEQUENCE: 5

```
Lys Asn Asp
1
```

<210> SEQ ID NO 6
<211> LENGTH: 11
<212> TYPE: PRT
<213> ORGANISM: Artificial Sequence
<220> FEATURE:
<223> OTHER INFORMATION: 2445_1F09 LCDR3

<400> SEQUENCE: 6

```
Ala Ala Trp Asp Asp Ser Leu Asn Gly Tyr Val
1               5                   10
```

<210> SEQ ID NO 7
<211> LENGTH: 118
<212> TYPE: PRT
<213> ORGANISM: Artificial Sequence
<220> FEATURE:
<223> OTHER INFORMATION: 2445_1F09 VH

<400> SEQUENCE: 7

```
Glu Val Gln Leu Leu Glu Thr Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80
```

```
Gln Met Asn Ser Leu Arg Ala Glu Asp Thr Ala Val Tyr Tyr Cys Ala
                85                  90                  95

Arg Asp Arg Gly Trp Asn His Gly Met Asp Val Trp Gly Gln Gly Thr
            100                 105                 110

Leu Val Thr Val Ser Ser
        115
```

```
<210> SEQ ID NO 8
<211> LENGTH: 110
<212> TYPE: PRT
<213> ORGANISM: Artificial Sequence
<220> FEATURE:
<223> OTHER INFORMATION: 2445_1F09 VL

<400> SEQUENCE: 8

Gln Ser Gly Leu Thr Gln Pro Pro Ser Ala Ser Gly Thr Pro Gly Gln
1               5                   10                  15

Arg Val Thr Ile Ser Cys Ser Gly Gly Ser Ser Glu Val Gly Ser Arg
            20                  25                  30

Tyr Val Ser Trp Tyr Gln Gln Leu Pro Gly Thr Ala Pro Arg Leu Leu
            35                  40                  45

Ile Tyr Lys Asn Asp Arg Arg Pro Ser Gly Val Pro Asp Arg Phe Ser
    50                  55                  60

Gly Ser Lys Ser Gly Ser Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Leu Thr Val Leu
            100                 105                 110
```

```
<210> SEQ ID NO 9
<211> LENGTH: 243
<212> TYPE: PRT
<213> ORGANISM: Artificial Sequence
<220> FEATURE:
<223> OTHER INFORMATION: 2445_1F09 scFv

<400> SEQUENCE: 9

Glu Val Gln Leu Leu Glu Thr Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
            35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Arg Gly Trp Asn His Gly Met Asp Val Trp Gly Gln Gly Thr
            100                 105                 110

Leu Val Thr Val Ser Ser Gly Gly Gly Ser Gly Gly Gly Gly Ser
        115                 120                 125

Gly Gly Gly Ala Ser Gln Ser Gly Leu Thr Gln Pro Pro Ser Ala Ser
    130                 135                 140

Gly Thr Pro Gly Gln Arg Val Thr Ile Ser Cys Ser Gly Gly Ser Ser
145                 150                 155                 160
```

-continued

```
Glu Val Gly Ser Arg Tyr Val Ser Trp Tyr Gln Gln Leu Pro Gly Thr
                165             170             175

Ala Pro Arg Leu Leu Ile Tyr Lys Asn Asp Arg Arg Pro Ser Gly Val
            180             185             190

Pro Asp Arg Phe Ser Gly Ser Lys Ser Gly Ser Ser Ala Ser Leu Ala
        195             200             205

Ile Ser Gly Leu Arg Ser Glu Asp Glu Ala Asp Tyr Tyr Cys Ala Ala
    210             215             220

Trp Asp Asp Ser Leu Asn Gly Tyr Val Phe Gly Thr Gly Thr Lys Leu
225             230             235             240

Thr Val Leu
```

```
<210> SEQ ID NO 10
<211> LENGTH: 729
<212> TYPE: DNA
<213> ORGANISM: Artificial Sequence
<220> FEATURE:
<223> OTHER INFORMATION: 2445_1F09 scFv

<400> SEQUENCE: 10
gaggtgcagc tgttggagac tggaggaggc ttgatccagc ctggggggtc cctgagactc        60
tcctgtgcag cctctgggtt caccgtcagt agcaactaca tgagctgggt ccgccaggct       120
ccagggaagg ggctggagtg ggtctcagtt atttatagcg gtggtagcac atattacgca       180
gactccgtga agggccgatt caccatctcc agagacaatt ccaagaacac gctgtatctt       240
caaatgaaca gcctgagagc cgaggacacg gccgtgtatt actgtgcgag agatcgcggc       300
tggaaccacg gtatggacgt ctggggccag ggaaccctgg tcaccgtctc gagtggtgga       360
ggcggttcag gcggaggtgg ctctggcggt ggcgctagcc agtctgggct gactcagcca       420
ccctcagcgt ctgggacccc cgggcagagg gtcaccatct cttgttctgg gggcagctca       480
gaagtcggaa gtagatatgt gtcctggtac agcaactcc caggaacggc ccccagactc        540
ctcatctata gaatgatcg gcggccctca ggggtccctg accgattctc tggctccaag        600
tctggctcct cagcctccct ggccatcagt gggctccggt ccgaggatga ggctgattat       660
tactgtgcag catgggatga cagcctgaat ggttatgtct tcggaactgg gaccaagctg       720
accgtccta                                                                  729
```

```
<210> SEQ ID NO 11
<211> LENGTH: 8
<212> TYPE: PRT
<213> ORGANISM: Artificial Sequence
<220> FEATURE:
<223> OTHER INFORMATION: 2447_2H08 HCDR1

<400> SEQUENCE: 11

Gly Tyr Thr Phe Thr Asn Tyr Gly
1               5
```

```
<210> SEQ ID NO 12
<211> LENGTH: 8
<212> TYPE: PRT
<213> ORGANISM: Artificial Sequence
<220> FEATURE:
<223> OTHER INFORMATION: 2447_2H08 HCDR2

<400> SEQUENCE: 12

Ile Ser Ala Tyr Asn Gly Asn Thr
1               5
```

```
<210> SEQ ID NO 13
<211> LENGTH: 16
<212> TYPE: PRT
<213> ORGANISM: Artificial Sequence
<220> FEATURE:
<223> OTHER INFORMATION: 2447_2H08 HCDR3

<400> SEQUENCE: 13

Asp Pro His Ile Leu Thr Gly Tyr Tyr Arg Gly Gly Trp Phe Asp Pro
1               5                   10                  15

<210> SEQ ID NO 14
<211> LENGTH: 6
<212> TYPE: PRT
<213> ORGANISM: Artificial Sequence
<220> FEATURE:
<223> OTHER INFORMATION: 2447_2H08 LCDR1

<400> SEQUENCE: 14

Ser Leu Arg Thr Ser Tyr
1               5

<210> SEQ ID NO 15
<211> LENGTH: 3
<212> TYPE: PRT
<213> ORGANISM: Artificial Sequence
<220> FEATURE:
<223> OTHER INFORMATION: 2447_2H08 LCDR2

<400> SEQUENCE: 15

Gly Lys Thr
1

<210> SEQ ID NO 16
<211> LENGTH: 13
<212> TYPE: PRT
<213> ORGANISM: Artificial Sequence
<220> FEATURE:
<223> OTHER INFORMATION: 2447_2H08 LCDR3

<400> SEQUENCE: 16

His Ser Arg Asp Ser Asn Asp Asn Tyr Leu Glu Val Val
1               5                   10

<210> SEQ ID NO 17
<211> LENGTH: 125
<212> TYPE: PRT
<213> ORGANISM: Artificial Sequence
<220> FEATURE:
<223> OTHER INFORMATION: 2447_2H08 VH

<400> SEQUENCE: 17

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
```

-continued

```
                   85                  90                  95

Ala Arg Asp Pro His Ile Leu Thr Gly Tyr Tyr Arg Gly Gly Trp Phe
            100                 105                 110

Asp Pro Trp Gly Gln Gly Thr Thr Val Thr Val Ser Ser
        115                 120                 125

<210> SEQ ID NO 18
<211> LENGTH: 110
<212> TYPE: PRT
<213> ORGANISM: Artificial Sequence
<220> FEATURE:
<223> OTHER INFORMATION: 2447_2H08 VL

<400> SEQUENCE: 18

Ser Tyr Glu Leu Thr Gln Asp Pro Ala Val Ser Val Ala Leu Gly Gln
1               5                   10                  15

Thr Val Thr Ile Thr Cys Gln Gly Asp Ser Leu Arg Thr Ser Tyr Ala
            20                  25                  30

Gly Trp Leu Gln Gln Lys Pro Gly Gln Ala Pro Val Leu Val Leu Tyr
        35                  40                  45

Gly Lys Thr Ser Arg Pro Ser Gly Ile Pro Asp Arg Phe Ser Gly Ser
    50                  55                  60

Thr Ser Gly Asn Thr Ala Ser Leu Thr Ile Thr Gly Ala Gln Ala Glu
65                  70                  75                  80

Asp Glu Ala Glu Tyr Phe Cys His Ser Arg Asp Ser Asn Asp Asn Tyr
                85                  90                  95

Leu Glu Val Val Phe Gly Gly Gly Thr Lys Leu Thr Val Leu
            100                 105                 110

<210> SEQ ID NO 19
<211> LENGTH: 250
<212> TYPE: PRT
<213> ORGANISM: Artificial Sequence
<220> FEATURE:
<223> OTHER INFORMATION: 2447_2H08 scFv

<400> SEQUENCE: 19

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Pro His Ile Leu Thr Gly Tyr Tyr Arg Gly Gly Trp Phe
            100                 105                 110

Asp Pro Trp Gly Gln Gly Thr Thr Val Thr Val Ser Ser Gly Gly Gly
        115                 120                 125

Gly Ser Gly Gly Gly Gly Ser Gly Gly Gly Ala Ser Ser Tyr Glu Leu
    130                 135                 140

Thr Gln Asp Pro Ala Val Ser Val Ala Leu Gly Gln Thr Val Thr Ile
145                 150                 155                 160
```

```
Thr Cys Gln Gly Asp Ser Leu Arg Thr Ser Tyr Ala Gly Trp Leu Gln
            165                 170                 175

Gln Lys Pro Gly Gln Ala Pro Val Leu Val Leu Tyr Gly Lys Thr Ser
            180                 185                 190

Arg Pro Ser Gly Ile Pro Asp Arg Phe Ser Gly Ser Thr Ser Gly Asn
        195                 200                 205

Thr Ala Ser Leu Thr Ile Thr Gly Ala Gln Ala Glu Asp Glu Ala Glu
    210                 215                 220

Tyr Phe Cys His Ser Arg Asp Ser Asn Asp Asn Tyr Leu Glu Val Val
225                 230                 235                 240

Phe Gly Gly Gly Thr Lys Leu Thr Val Leu
                245                 250
```

```
<210> SEQ ID NO 20
<211> LENGTH: 750
<212> TYPE: DNA
<213> ORGANISM: Artificial Sequence
<220> FEATURE:
<223> OTHER INFORMATION: 2447_2H08 scFv

<400> SEQUENCE: 20
gaagtgcagc tggtgcagtc tggagctgag gtgaagaagc ctggggcctc agtgaaggtc      60
tcctgcaagg cttctggtta cacctttacc aactacggta tcagctgggt gcgacaggcc     120
cctggacaag ggcttgagtg gatgggatgg atcagcgctt acaatggtaa cacaaactat     180
gcacagaagc tccagggcag agtcaccatg accacagaca tccacgag  cacagcctac     240 atggagctga ggagcctgag atctgacgac acggccgtgt attactgtgc gagagatccg     300
catattttga ctggttatta taggggaggg tggttcgacc cctgggggca agggaccacg     360
gtcaccgtct cgagtggtgg aggcggttca ggcggaggtg gctctggcgg tggcgctagc     420
tcctatgagc tgactcagga ccctgctgtg tctgtggcct tgggtcagac agtcaccatc     480
acgtgccaag agacagcct  cagaacctct tatgcaggct ggctccagca gaagccagga     540
caggcccctg tactcgtcct ctatggtaaa accagccggc cctcagggat cccagaccga     600
ttctctggct ccacctcagg aaacacagct tccttgacca tcactgggc tcaggcggag     660 gatgaggctg agtatttctg tcactcccgg gacagcaatg ataactatct agaggtggtt     720
ttcggcggag ggaccaagct gaccgtccta                                      750
```

```
<210> SEQ ID NO 21
<211> LENGTH: 8
<212> TYPE: PRT
<213> ORGANISM: Artificial Sequence
<220> FEATURE:
<223> OTHER INFORMATION: 2447_3A01 HCDR1

<400> SEQUENCE: 21

Gly Phe Thr Phe Asp Asp Tyr Ala
1               5
```

```
<210> SEQ ID NO 22
<211> LENGTH: 8
<212> TYPE: PRT
<213> ORGANISM: Artificial Sequence
<220> FEATURE:
<223> OTHER INFORMATION: 2447_3A01 HCDR2

<400> SEQUENCE: 22

Ile Ser Trp Asn Ser Gly Ser Ile
1               5
```

```
<210> SEQ ID NO 23
<211> LENGTH: 13
<212> TYPE: PRT
<213> ORGANISM: Artificial Sequence
<220> FEATURE:
<223> OTHER INFORMATION: 2447_3A01 HCDR3

<400> SEQUENCE: 23

Asp Ile Ser Ser Gly Trp Tyr Pro Gly Thr Phe Asp Tyr
1               5                   10

<210> SEQ ID NO 24
<211> LENGTH: 6
<212> TYPE: PRT
<213> ORGANISM: Artificial Sequence
<220> FEATURE:
<223> OTHER INFORMATION: 2447_3A01 LCDR1

<400> SEQUENCE: 24

Ser Leu Arg Ser Tyr Tyr
1               5

<210> SEQ ID NO 25
<211> LENGTH: 3
<212> TYPE: PRT
<213> ORGANISM: Artificial Sequence
<220> FEATURE:
<223> OTHER INFORMATION: 2447_3A01 LCDR2

<400> SEQUENCE: 25

Gly Lys Asn
1

<210> SEQ ID NO 26
<211> LENGTH: 10
<212> TYPE: PRT
<213> ORGANISM: Artificial Sequence
<220> FEATURE:
<223> OTHER INFORMATION: 2447_3A01 LCDR3

<400> SEQUENCE: 26

Ser Ser Arg Asp Ser Ser Asp Asp Val Val
1               5                   10

<210> SEQ ID NO 27
<211> LENGTH: 122
<212> TYPE: PRT
<213> ORGANISM: Artificial Sequence
<220> FEATURE:
<223> OTHER INFORMATION: 2447_3A01 VH

<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Val Tyr Ala Asp Phe Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
```

```
              85                90                95

Ala Lys Asp Ile Ser Ser Gly Trp Tyr Pro Gly Thr Phe Asp Tyr Trp
          100               105               110

Gly Gln Gly Thr Leu Val Thr Val Ser Ser
        115               120

<210> SEQ ID NO 28
<211> LENGTH: 107
<212> TYPE: PRT
<213> ORGANISM: Artificial Sequence
<220> FEATURE:
<223> OTHER INFORMATION: 2447_3A01 VL

<400> SEQUENCE: 28

Ser Tyr Glu Leu Thr Gln Asp Pro Ala Val Ser Val Ala Leu Gly Gln
1               5                 10                15

Thr Val Arg Ile Thr Cys Gln Gly Asp Ser Leu Arg Ser Tyr Tyr Ala
            20                25                30

Ser Trp Tyr Gln Gln Lys Pro Gly Gln Ala Pro Val Leu Val Ile Tyr
        35                40                45

Gly Lys Asn Asn Arg Pro Ser Gly Ile Pro Asp Arg Phe Ser Gly Ser
    50                55                60

Ser Ser Gly Asn Thr Ala Ser Leu Thr Val Thr Gly Ala Gln Ala Glu
65                70                75                80

Asp Glu Ala Asp Tyr Tyr Cys Ser Ser Arg Asp Ser Ser Asp Asp Val
                85                90                95

Val Phe Gly Gly Gly Thr Gln Leu Thr Val Leu
            100               105

<210> SEQ ID NO 29
<211> LENGTH: 244
<212> TYPE: PRT
<213> ORGANISM: Artificial Sequence
<220> FEATURE:
<223> OTHER INFORMATION: 2447_3A01 scFv

<400> SEQUENCE: 29

Glu Val Gln Leu Leu Glu Ser Gly Gly Gly Leu Val Gln Pro Gly Gly
1               5                 10                15

Ser Leu Arg Leu Ser Cys Ala Ala Ser Gly Phe Thr Phe Asp Asp Tyr
            20                25                30

Ala Met His Trp Val Arg Gln Ala Pro Gly Lys Gly Leu Glu Trp Val
        35                40                45

Ser Gly Ile Ser Trp Asn Ser Gly Ser Ile Val Tyr Ala Asp Phe Val
    50                55                60

Lys Gly Arg Phe Thr Ile Ser Arg Asp Asn Ala Lys Asn Ser Leu Tyr
65                70                75                80

Leu Gln Met Asn Ser Leu Arg Ala Glu Asp Thr Ala Leu Tyr Tyr Cys
                85                90                95

Ala Lys Asp Ile Ser Ser Gly Trp Tyr Pro Gly Thr Phe Asp Tyr Trp
          100               105               110

Gly Gln Gly Thr Leu Val Thr Val Ser Ser Gly Gly Gly Gly Ser Gly
        115               120               125

Gly Gly Gly Ser Gly Gly Gly Ala Ser Ser Tyr Glu Leu Thr Gln Asp
    130               135               140

Pro Ala Val Ser Val Ala Leu Gly Gln Thr Val Arg Ile Thr Cys Gln
145               150               155               160
```

-continued

```
Gly Asp Ser Leu Arg Ser Tyr Tyr Ala Ser Trp Tyr Gln Gln Lys Pro
            165                 170                 175

Gly Gln Ala Pro Val Leu Val Ile Tyr Gly Lys Asn Asn Arg Pro Ser
        180                 185                 190

Gly Ile Pro Asp Arg Phe Ser Gly Ser Ser Ser Gly Asn Thr Ala Ser
        195                 200                 205

Leu Thr Val Thr Gly Ala Gln Ala Glu Asp Glu Ala Asp Tyr Tyr Cys
    210                 215                 220

Ser Ser Arg Asp Ser Ser Asp Asp Val Val Phe Gly Gly Gly Thr Gln
225                 230                 235                 240

Leu Thr Val Leu
```

```
<210> SEQ ID NO 30
<211> LENGTH: 732
<212> TYPE: DNA
<213> ORGANISM: Artificial Sequence
<220> FEATURE:
<223> OTHER INFORMATION: 2447_3A01 scFv

<400> SEQUENCE: 30
gaggtgcagc tgttggagtc tggggggggc ttggtacagc ctggggggtc cctgagactc      60
tcctgtgcag cctctggatt cacctttgat gattatgcca tgcactgggt ccggcaagct     120
ccagggaagg gcctggagtg ggtctcaggt attagttgga atagtggtag catagtctat     180
gcggactttg tgaagggccg attcaccatc tccagagaca acgccaagaa ctccctgtat     240
ctgcaaatga acagtctgag agctgaggac acggccttgt attactgtgc aaaagatatt     300
tcaagtggct ggtacccagg gacctttgac tactggggcc agggaaccct ggtcaccgtc     360
tcgagtggtg gaggcggttc aggcggaggt ggctctggcg gtggcgctag ctcctatgag     420
ctgactcagg accctgctgt gtctgtggcc ttgggacaga cagtcaggat cacatgccaa     480
ggagacagcc tcagaagcta ttatgcaagc tggtaccagc agaagccagg acaggcccct     540
gtacttgtca tctatggtaa aaacaaccgg ccctcaggga tcccagaccg attctctggc     600
tccagctcag gaaacacagc ttccttgacc gtcactgggg ctcaggcgga agacgaggct     660
gactattact gtagctcccg ggacagcagt gatgatgtgg tattcggcgg agggacccag     720
ctcaccgtcc ta                                                         732
```

```
<210> SEQ ID NO 31
<211> LENGTH: 8
<212> TYPE: PRT
<213> ORGANISM: Artificial Sequence
<220> FEATURE:
<223> OTHER INFORMATION: 2447_3A08 HCDR1

<400> SEQUENCE: 31

Gly Tyr Thr Phe Thr Ser Tyr Gly
1               5
```

```
<210> SEQ ID NO 32
<211> LENGTH: 8
<212> TYPE: PRT
<213> ORGANISM: Artificial Sequence
<220> FEATURE:
<223> OTHER INFORMATION: 2447_3A08 HCDR2

<400> SEQUENCE: 32

Ile Ser Ala Tyr Asn Gly Asn Thr
1               5
```

```
<210> SEQ ID NO 33
<211> LENGTH: 14
<212> TYPE: PRT
<213> ORGANISM: Artificial Sequence
<220> FEATURE:
<223> OTHER INFORMATION: 2447_3A08 HCDR3

<400> SEQUENCE: 33

Asp Arg Ala Thr Ile Phe Gly Val Val Thr Pro Phe Asp Tyr
1               5                   10

<210> SEQ ID NO 34
<211> LENGTH: 6
<212> TYPE: PRT
<213> ORGANISM: Artificial Sequence
<220> FEATURE:
<223> OTHER INFORMATION: 2447_3A08 LCDR1

<400> SEQUENCE: 34

Ser Ile Arg Ser Tyr Ser
1               5

<210> SEQ ID NO 35
<211> LENGTH: 3
<212> TYPE: PRT
<213> ORGANISM: Artificial Sequence
<220> FEATURE:
<223> OTHER INFORMATION: 2447_3A08 LCDR2

<400> SEQUENCE: 35

Gly Lys Asn
1

<210> SEQ ID NO 36
<211> LENGTH: 11
<212> TYPE: PRT
<213> ORGANISM: Artificial Sequence
<220> FEATURE:
<223> OTHER INFORMATION: 2447_3A08 LCDR3

<400> SEQUENCE: 36

Asn Ser Arg Asp Ser Ser Gly Asn Arg Val Val
1               5                   10

<210> SEQ ID NO 37
<211> LENGTH: 123
<212> TYPE: PRT
<213> ORGANISM: Artificial Sequence
<220> FEATURE:
<223> OTHER INFORMATION: 2447_3A08 VH

<400> SEQUENCE: 37

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95
```

```
Ala Arg Asp Arg Ala Thr Ile Phe Gly Val Val Thr Pro Phe Asp Tyr
            100                 105                 110

Trp Gly Gln Gly Thr Leu Val Thr Val Ser Ser
        115                 120

<210> SEQ ID NO 38
<211> LENGTH: 108
<212> TYPE: PRT
<213> ORGANISM: Artificial Sequence
<220> FEATURE:
<223> OTHER INFORMATION: 2447_3A08 VL

<400> SEQUENCE: 38

Ser Tyr Glu Leu Thr Gln Asp Pro Ala Val Ser Val Ala Leu Gly Gln
1               5                   10                  15

Thr Val Arg Ile Thr Cys Gln Gly Asp Ser Ile Arg Ser Tyr Ser Ala
            20                  25                  30

Ser Trp Tyr Gln Gln Lys Pro Gly Gln Ala Pro Arg Leu Val Ile Tyr
        35                  40                  45

Gly Lys Asn Asn Arg Pro Ser Gly Ile Pro Asp Arg Val Ser Gly Ser
    50                  55                  60

Thr Ser Gly Asn Thr Ala Ser Leu Thr Val Thr Gly Ala Gln Ala Glu
65                  70                  75                  80

Asp Glu Ala Asp Tyr Tyr Cys Asn Ser Arg Asp Ser Ser Gly Asn Arg
                85                  90                  95

Val Val Phe Gly Gly Gly Thr Gln Leu Thr Val Leu
            100                 105

<210> SEQ ID NO 39
<211> LENGTH: 246
<212> TYPE: PRT
<213> ORGANISM: Artificial Sequence
<220> FEATURE:
<223> OTHER INFORMATION: 2447_3A08 scFv

<400> SEQUENCE: 39

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Ala Thr Ile Phe Gly Val Val Thr Pro Phe Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Ala Ser Ser Tyr Glu Leu Thr Gln
    130                 135                 140

Asp Pro Ala Val Ser Val Ala Leu Gly Gln Thr Val Arg Ile Thr Cys
145                 150                 155                 160

Gln Gly Asp Ser Ile Arg Ser Tyr Ser Ala Ser Trp Tyr Gln Gln Lys
```

```
                   165                170                175
Pro Gly Gln Ala Pro Arg Leu Val Ile Tyr Gly Lys Asn Asn Arg Pro
            180                185                190

Ser Gly Ile Pro Asp Arg Val Ser Gly Ser Thr Ser Gly Asn Thr Ala
    195                200                205

Ser Leu Thr Val Thr Gly Ala Gln Ala Glu Asp Glu Ala Asp Tyr Tyr
    210                215                220

Cys Asn Ser Arg Asp Ser Ser Gly Asn Arg Val Val Phe Gly Gly Gly
225                230                235                240

Thr Gln Leu Thr Val Leu
            245
```

<210> SEQ ID NO 40
<211> LENGTH: 738
<212> TYPE: DNA
<213> ORGANISM: Artificial Sequence
<220> FEATURE:
<223> OTHER INFORMATION: 2447_3A08 scFv

<400> SEQUENCE: 40

```
gaagtgcagc tggtgcagtc tggagctgag gtgaagaagc ctgggggcctc agtgaaggtc      60 tcctgcaagg cttctggtta cacctttacc agctacggta tcagctgggt gcgacaggcc     120
cctggacaag ggcttgagtg gatgggatgg atcagcgctt acaatggtaa cacaaactat     180
gcacagaagc tccagggcag agtcaccatg accacagaca catccacgag cacagcctac     240
atggagctga ggagcctgag atctgacgac acggccgtgt attactgtgc gagagatcgg     300
gctacgattt ttggagtggt tacccccttt gactactggg gccaaggaac cctggtcacc     360
gtctcgagtg gtggaggcgg ttcaggcgga ggtggctctg gcggtggcgc tagctcctat     420
gagctgactc aggaccccgc tgtgtctgtg gccttgggac agacagtcag gatcacatgc     480
caggagacag tattagaag ttattctgcc agctggtacc agcagaagcc agggcaggcc     540
cctcgccttg ttatctatgg taaaaacaac cggccctcag ggatcccaga ccgagtctct     600
ggctccactt caggaaatac agcttccttg accgtcactg gggctcaggc ggaagatgag     660
gctgactatt actgtaactc ccgggacagc agtggtaacc gtgtggtatt cggcggaggg     720
acccagctca ccgtccta                                                   738
```

<210> SEQ ID NO 41
<211> LENGTH: 8
<212> TYPE: PRT
<213> ORGANISM: Artificial Sequence
<220> FEATURE:
<223> OTHER INFORMATION: 2447_3A09 HCDR1

<400> SEQUENCE: 41

```
Gly Phe Thr Phe Asp Asp Tyr Ala
1               5
```

<210> SEQ ID NO 42
<211> LENGTH: 8
<212> TYPE: PRT
<213> ORGANISM: Artificial Sequence
<220> FEATURE:
<223> OTHER INFORMATION: 2447_3A09 HCDR2

<400> SEQUENCE: 42

```
Ile Ser Trp Asn Ser Gly Ser Ile
1               5
```

```
<210> SEQ ID NO 43
<211> LENGTH: 13
<212> TYPE: PRT
<213> ORGANISM: Artificial Sequence
<220> FEATURE:
<223> OTHER INFORMATION: 2447_3A09 HCDR3

<400> SEQUENCE: 43

Asp Val Ser Ser Gly Trp Tyr Trp Tyr Ala Phe Asp Ile
1               5                   10

<210> SEQ ID NO 44
<211> LENGTH: 6
<212> TYPE: PRT
<213> ORGANISM: Artificial Sequence
<220> FEATURE:
<223> OTHER INFORMATION: 2447_3A09 LCDR1

<400> SEQUENCE: 44

Ser Leu Arg Ser Tyr Tyr
1               5

<210> SEQ ID NO 45
<211> LENGTH: 3
<212> TYPE: PRT
<213> ORGANISM: Artificial Sequence
<220> FEATURE:
<223> OTHER INFORMATION: 2447_3A09 LCDR2

<400> SEQUENCE: 45

Gly Lys Asn
1

<210> SEQ ID NO 46
<211> LENGTH: 10
<212> TYPE: PRT
<213> ORGANISM: Artificial Sequence
<220> FEATURE:
<223> OTHER INFORMATION: 2447_3A09 LCDR3

<400> SEQUENCE: 46

Asn Ser Arg Asp Ser Gly Gly Ser Val Val
1               5                   10

<210> SEQ ID NO 47
<211> LENGTH: 122
<212> TYPE: PRT
<213> ORGANISM: Artificial Sequence
<220> FEATURE:
<223> OTHER INFORMATION: 2447_3A09 VH

<400> SEQUENCE: 47

Glu Val Gln Leu Leu Glu Ser Gly Gly Gly Leu Val Gln Pro Gly Arg
1               5                   10                  15

Ser Leu Arg Leu Ser Cys Ala Ala Thr Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Ser Tyr Tyr Cys
                85                  90                  95
```

```
Ala Lys Asp Val Ser Ser Gly Trp Tyr Trp Tyr Ala Phe Asp Ile Trp
            100                 105                 110

Gly Gln Gly Thr Leu Val Thr Val Ser Ser
        115                 120

<210> SEQ ID NO 48
<211> LENGTH: 107
<212> TYPE: PRT
<213> ORGANISM: Artificial Sequence
<220> FEATURE:
<223> OTHER INFORMATION: 2447_3A09 VL

<400> SEQUENCE: 48

Ser Tyr Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Gly Arg Phe Ser Gly Ser
    50                  55                  60

Ser Ser Gly Asn Thr Ala Ser Leu Thr Val Thr Gly Ala Gln Ala Glu
65                  70                  75                  80

Asp Glu Ala Asp Tyr Tyr Cys Asn Ser Arg Asp Ser Gly Gly Ser Val
            85                  90                  95

Val Phe Gly Gly Gly Thr Lys Leu Thr Val Leu
        100                 105

<210> SEQ ID NO 49
<211> LENGTH: 244
<212> TYPE: PRT
<213> ORGANISM: Artificial Sequence
<220> FEATURE:
<223> OTHER INFORMATION: 2447_3A09 scFv

<400> SEQUENCE: 49

Glu Val Gln Leu Leu Glu Ser Gly Gly Gly Leu Val Gln Pro Gly Arg
1               5                   10                  15

Ser Leu Arg Leu Ser Cys Ala Ala Thr Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Ser Tyr Tyr Cys
            85                  90                  95

Ala Lys Asp Val Ser Ser Gly Trp Tyr Trp Tyr Ala Phe Asp Ile Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ala Ser Ser Tyr Glu Leu Thr Gln Asp
    130                 135                 140

Pro Ala Val Ser Val Ala Leu Gly Gln Thr Val Arg Ile Thr Cys Gln
145                 150                 155                 160

Gly Asp Ser Leu Arg Ser Tyr Tyr Ala Ser Trp Tyr Gln Gln Lys Pro
```

-continued

```
              165               170               175
Gly Gln Ala Pro Val Leu Val Ile Tyr Gly Lys Asn Asn Arg Pro Ser
            180               185               190

Gly Ile Pro Gly Arg Phe Ser Gly Ser Ser Ser Gly Asn Thr Ala Ser
        195               200               205

Leu Thr Val Thr Gly Ala Gln Ala Glu Asp Glu Ala Asp Tyr Tyr Cys
    210               215               220

Asn Ser Arg Asp Ser Gly Gly Ser Val Val Phe Gly Gly Gly Thr Lys
225               230               235               240

Leu Thr Val Leu
```

```
<210> SEQ ID NO 50
<211> LENGTH: 732
<212> TYPE: DNA
<213> ORGANISM: Artificial Sequence
<220> FEATURE:
<223> OTHER INFORMATION: 2447_3A09 scFv

<400> SEQUENCE: 50
gaggtgcagc tgttggagtc tggggggaggc ttggtacagc ctggcaggtc cctgagactc      60
tcctgtgcag ccactggatt cacctttgat gattatgcca tgcactgggt ccggcaagct     120
ccagggaagg gcctggagtg ggtctcaggt attagttgga atagtggtag cataggctat     180
gcggactctg tgaagggccg attcaccatc tccagagaca acgccaagaa ctccctgtat     240
ctgcaaatga acagtctgag agctgaggac acggcctcgt attactgtgc aaaagatgtt     300
agcagtggct ggtactggta tgctttttgat atctgggggcc aaggaaccct ggtcaccgtc     360
tcgagtggtg gaggcggttc aggcggaggt ggctctggcg gtggcgctag ctcctatgag     420
ctgactcagg accctgctgt gtctgtggcc ttgggacaga cagtcaggat cacatgccaa     480
ggagacagcc tcagaagcta ttatgcaagc tggtaccagc agaagccagg acaggcccct     540
gtacttgtca tctatggtaa aaacaaccgg ccctcaggga tcccaggccg attctctggc     600
tccagctcag gaaacacagc ttccttgacc gtcactgggg ctcaggcgga agatgaggct     660
gactattact gtaattcccg ggacagcggt ggttctgtgg ttttcggcgg agggaccaag     720
ctgaccgtcc ta                                                         732
```

```
<210> SEQ ID NO 51
<211> LENGTH: 8
<212> TYPE: PRT
<213> ORGANISM: Artificial Sequence
<220> FEATURE:
<223> OTHER INFORMATION: 2447_3A12 HCDR1

<400> SEQUENCE: 51

Gly Tyr Thr Phe Thr Ser Tyr Gly
1               5
```

```
<210> SEQ ID NO 52
<211> LENGTH: 8
<212> TYPE: PRT
<213> ORGANISM: Artificial Sequence
<220> FEATURE:
<223> OTHER INFORMATION: 2447_3A12 HCDR2

<400> SEQUENCE: 52

Ile Ser Ala Tyr Asn Gly Asn Thr
1               5
```

```
<210> SEQ ID NO 53
<211> LENGTH: 16
<212> TYPE: PRT
<213> ORGANISM: Artificial Sequence
<220> FEATURE:
<223> OTHER INFORMATION: 2447_3A12 HCDR3

<400> SEQUENCE: 53

Asp Pro His Ile Leu Thr Gly Tyr Tyr Arg Gly Gly Trp Phe Asp Pro
1               5                   10                  15

<210> SEQ ID NO 54
<211> LENGTH: 6
<212> TYPE: PRT
<213> ORGANISM: Artificial Sequence
<220> FEATURE:
<223> OTHER INFORMATION: 2447_3A12 LCDR1

<400> SEQUENCE: 54

Ser Leu Arg Ser Tyr Tyr
1               5

<210> SEQ ID NO 55
<211> LENGTH: 3
<212> TYPE: PRT
<213> ORGANISM: Artificial Sequence
<220> FEATURE:
<223> OTHER INFORMATION: 2447_3A12 LCDR2

<400> SEQUENCE: 55

Gly Lys Asn
1

<210> SEQ ID NO 56
<211> LENGTH: 11
<212> TYPE: PRT
<213> ORGANISM: Artificial Sequence
<220> FEATURE:
<223> OTHER INFORMATION: 2447_3A12 LCDR3

<400> SEQUENCE: 56

Asn Ser Arg Asp Ser Ser Gly Asn His Arg Val
1               5                   10

<210> SEQ ID NO 57
<211> LENGTH: 125
<212> TYPE: PRT
<213> ORGANISM: Artificial Sequence
<220> FEATURE:
<223> OTHER INFORMATION: 2447_3A12 VH

<400> SEQUENCE: 57

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Arg Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95
```

```
Ala Arg Asp Pro His Ile Leu Thr Gly Tyr Tyr Arg Gly Gly Trp Phe
            100                 105                 110

Asp Pro Trp Gly Gln Gly Thr Leu Val Thr Val Ser Ser
        115                 120                 125

<210> SEQ ID NO 58
<211> LENGTH: 108
<212> TYPE: PRT
<213> ORGANISM: Artificial Sequence
<220> FEATURE:
<223> OTHER INFORMATION: 2447_3A12 VL

<400> SEQUENCE: 58

Ser Tyr Glu Leu Thr Gln Asp Pro Ala Val Ser Val Val Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Arg Val Phe Gly Gly Gly Thr Lys Leu Thr Val Leu
            100                 105

<210> SEQ ID NO 59
<211> LENGTH: 248
<212> TYPE: PRT
<213> ORGANISM: Artificial Sequence
<220> FEATURE:
<223> OTHER INFORMATION: 2447_3A12 scFv

<400> SEQUENCE: 59

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Arg Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Pro His Ile Leu Thr Gly Tyr Tyr Arg Gly Gly Trp Phe
            100                 105                 110

Asp Pro Trp Gly Gln Gly Thr Leu Val Thr Val Ser Ser Gly Gly Gly
        115                 120                 125

Gly Ser Gly Gly Gly Gly Ser Gly Gly Gly Ala Ser Ser Tyr Glu Leu
    130                 135                 140

Thr Gln Asp Pro Ala Val Ser Val Val Leu Gly Gln Thr Val Arg Ile
145                 150                 155                 160

Thr Cys Gln Gly Asp Ser Leu Arg Ser Tyr Tyr Ala Ser Trp Tyr Gln
                165                 170                 175
```

-continued

```
Gln Lys Pro Gly Gln Ala Pro Val Leu Val Ile Tyr Gly Lys Asn Asn
            180                 185                 190

Arg Pro Ser Gly Ile Pro Asp Arg Phe Ser Gly Ser Ser Ser Gly Asn
            195                 200                 205

Thr Ala Ser Leu Thr Ile Thr Gly Ala Gln Ala Glu Asp Glu Ala Asp
        210                 215                 220

Tyr Tyr Cys Asn Ser Arg Asp Ser Ser Gly Asn His Arg Val Phe Gly
225                 230                 235                 240

Gly Gly Thr Lys Leu Thr Val Leu
                245
```

```
<210> SEQ ID NO 60
<211> LENGTH: 744
<212> TYPE: DNA
<213> ORGANISM: Artificial Sequence
<220> FEATURE:
<223> OTHER INFORMATION: 2447_3A12 scFv

<400> SEQUENCE: 60
gaagtgcagc tggtgcagtc tggagctgag gtgaagaagc ctggggcctc agtgaaggtc      60
tcctgcaagg cttctggtta cacctttacc agctatggta tcagctgggt gcgacaggcc     120
cctggacaag ggcttgagtg gatgggatgg atcagcgctt acaatggtaa cacaaactat     180
gcacagaagc tccggggcag agtcaccatg accacagaca catccacgag cacagcctac     240
atggagctga ggagcctgag atctgacgac acggccgtgt attactgtgc gagagatccg     300
catattttga ctggttatta taggggaggg tggttcgacc cctggggcca gggcaccctg     360
gtcaccgtct cgagtggtgg aggcggttca ggcggaggtg gctctggcgg tggcgctagc     420
tcctatgagc tgactcagga ccctgctgtg tctgtggtct tgggacagac agtcaggatc     480
acatgccaag agacagcct cagaagctat tatgcaagct ggtaccagca gaagccagga     540
caggcccctg tacttgtcat ctatggtaaa aacaaccggc cctcaggat cccagaccga     600 ttctctggct ccagctcagg aaacacagct tccttgacca tcactgggc tcaggcggaa     660 gatgaggctg actattactg taactcccgg gacagcagtg taaccatcg tgtattcggc     720 ggagggacca agctgaccgt ccta                                           744
```

```
<210> SEQ ID NO 61
<211> LENGTH: 8
<212> TYPE: PRT
<213> ORGANISM: Artificial Sequence
<220> FEATURE:
<223> OTHER INFORMATION: 2447_3B07 HCDR1

<400> SEQUENCE: 61

Gly Phe Thr Phe Asp Asp Tyr Ala
1               5
```

```
<210> SEQ ID NO 62
<211> LENGTH: 8
<212> TYPE: PRT
<213> ORGANISM: Artificial Sequence
<220> FEATURE:
<223> OTHER INFORMATION: 2447_3B07 HCDR2

<400> SEQUENCE: 62

Thr Ser Trp Asp Gly Gly Ser Thr
1               5
```

```
<210> SEQ ID NO 63
<211> LENGTH: 10
<212> TYPE: PRT
<213> ORGANISM: Artificial Sequence
<220> FEATURE:
<223> OTHER INFORMATION: 2447_3B07 HCDR3

<400> SEQUENCE: 63

Asp His Ser Ser Gly Trp Tyr Asn Gly Gly
1               5                   10

<210> SEQ ID NO 64
<211> LENGTH: 6
<212> TYPE: PRT
<213> ORGANISM: Artificial Sequence
<220> FEATURE:
<223> OTHER INFORMATION: 2447_3B07 LCDR1

<400> SEQUENCE: 64

Ser Leu Arg Ser Tyr Tyr
1               5

<210> SEQ ID NO 65
<211> LENGTH: 3
<212> TYPE: PRT
<213> ORGANISM: Artificial Sequence
<220> FEATURE:
<223> OTHER INFORMATION: 2447_3B07 LCDR2

<400> SEQUENCE: 65

Gly Lys Asn
1

<210> SEQ ID NO 66
<211> LENGTH: 11
<212> TYPE: PRT
<213> ORGANISM: Artificial Sequence
<220> FEATURE:
<223> OTHER INFORMATION: 2447_3B07 LCDR3

<400> SEQUENCE: 66

Asn Ser Arg Asp Ser Ser Gly Asn His Val Val
1               5                   10

<210> SEQ ID NO 67
<211> LENGTH: 122
<212> TYPE: PRT
<213> ORGANISM: Artificial Sequence
<220> FEATURE:
<223> OTHER INFORMATION: 2447_3B07 VH

<400> SEQUENCE: 67

Gln Val Gln Leu Val Glu Ser Gly Gly Val Val Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Arg Gly Leu Glu Trp Val
            35                  40                  45

Ser Leu Thr Ser Trp Asp Gly Gly Ser Thr Tyr Tyr Ala Asp Ser Val
        50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Leu Tyr Tyr Cys
                85                  90                  95
```

-continued

```
Ala Lys Asp His Ser Ser Gly Trp Tyr Asn Gly Gly Met Asp Val Trp
            100             105             110

Gly Gln Gly Thr Met Val Thr Val Ser Ser
        115             120

<210> SEQ ID NO 68
<211> LENGTH: 108
<212> TYPE: PRT
<213> ORGANISM: Artificial Sequence
<220> FEATURE:
<223> OTHER INFORMATION: 2447_3B07 VL

<400> SEQUENCE: 68

Ser Tyr Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu
            100             105

<210> SEQ ID NO 69
<211> LENGTH: 245
<212> TYPE: PRT
<213> ORGANISM: Artificial Sequence
<220> FEATURE:
<223> OTHER INFORMATION: 2447_3B07 scFv

<400> SEQUENCE: 69

Gln Val Gln Leu Val Glu Ser Gly Gly Val Val Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Arg Gly Leu Glu Trp Val
        35                  40                  45

Ser Leu Thr Ser Trp Asp Gly Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp His Ser Ser Gly Trp Tyr Asn Gly Gly Met Asp Val Trp
            100             105             110

Gly Gln Gly Thr Met Val Thr Val Ser Ser Gly Gly Gly Gly Ser Gly
        115             120             125

Gly Gly Gly Ser Gly Gly Gly Ala Ser Ser Tyr Glu Leu Thr Gln Asp
    130             135             140

Pro Ala Val Ser Val Ala Leu Gly Gln Thr Val Arg Ile Thr Cys Gln
145             150             155             160

Gly Asp Ser Leu Arg Ser Tyr Tyr Ala Ser Trp Tyr Gln Gln Lys Pro
                165             170             175
```

```
Gly Gln Ala Pro Val Leu Val Ile Tyr Gly Lys Asn Asn Arg Pro Ser
            180                 185                 190

Gly Ile Pro Asp Arg Phe Ser Gly Ser Ser Ser Gly Asn Thr Ala Ser
        195                 200                 205

Leu Thr Ile Thr Gly Ala Gln Ala Glu Asp Glu Ala Asp Tyr Tyr Cys
    210                 215                 220

Asn Ser Arg Asp Ser Ser Gly Asn His Val Val Phe Gly Gly Gly Thr
225                 230                 235                 240

Lys Leu Thr Val Leu
                245

<210> SEQ ID NO 70
<211> LENGTH: 735
<212> TYPE: DNA
<213> ORGANISM: Artificial Sequence
<220> FEATURE:
<223> OTHER INFORMATION: 2447_3B07 scFv

<400> SEQUENCE: 70
caggtgcagc tggtggagtc tgggggagtc gtggtacagc ctggggggtc cctgagactc      60
tcctgtgcag cctctggatt cacctttgat gattatgcca tgcactgggt ccgtcaagct     120
ccggggaggg gtctggagtg ggtctctctt actagttggg atggtggtag cacatactat     180
gcagactctg tgaagggtcg attcaccatc tccagagaca cagcaaaaa ctccctgtat     240 ctgcaaatga acagtctgag agctgaggac accgccttgt attactgtgc aaaagatcat     300
agcagcggct ggtacaacgg gggtatggac gtctgggggcc aagggacaat ggtcaccgtc     360
tcgagtggtg gaggcggttc aggcggaggt ggctctggcg gtggcgctag ctcctatgag     420
ctgactcagg accctgctgt gtctgtggcc ttgggacaga cagtcaggat cacatgccaa     480
ggagacagcc tcagaagcta ttatgcaagc tggtaccagc agaagccagg acaggcccct     540
gtacttgtca tctatggtaa aaacaaccgg ccctcaggga tcccagaccg attctctggc     600
tccagctcag gaaacacagc ttccttgacc atcactgggg ctcaggcgga agatgaggct     660
gactattact gtaactcccg ggacagcagt ggtaaccatg tggtattcgg cggagggacc     720
aagctgaccg tccta                                                       735

<210> SEQ ID NO 71
<211> LENGTH: 8
<212> TYPE: PRT
<213> ORGANISM: Artificial Sequence
<220> FEATURE:
<223> OTHER INFORMATION: 2447_3C08 HCDR1

<400> SEQUENCE: 71

Gly Phe Thr Phe Asp Asp Tyr Ala
1               5

<210> SEQ ID NO 72
<211> LENGTH: 8
<212> TYPE: PRT
<213> ORGANISM: Artificial Sequence
<220> FEATURE:
<223> OTHER INFORMATION: 2447_3C08 HCDR2

<400> SEQUENCE: 72

Ile Ser Trp Asn Ser Gly Ser Ile
1               5
```

<210> SEQ ID NO 73
<211> LENGTH: 15
<212> TYPE: PRT
<213> ORGANISM: Artificial Sequence
<220> FEATURE:
<223> OTHER INFORMATION: 2447_3C08 HCDR3

<400> SEQUENCE: 73

Asp Arg Gly Ser Gly Tyr Glu Gly Asn Tyr Tyr Gly Met Asp Val
1               5                   10                  15

<210> SEQ ID NO 74
<211> LENGTH: 6
<212> TYPE: PRT
<213> ORGANISM: Artificial Sequence
<220> FEATURE:
<223> OTHER INFORMATION: 2447_3C08 LCDR1

<400> SEQUENCE: 74

Ser Leu Arg Ser Tyr Tyr
1               5

<210> SEQ ID NO 75
<211> LENGTH: 3
<212> TYPE: PRT
<213> ORGANISM: Artificial Sequence
<220> FEATURE:
<223> OTHER INFORMATION: 2447_3C08 LCDR2

<400> SEQUENCE: 75

Gly Lys Asn
1

<210> SEQ ID NO 76
<211> LENGTH: 11
<212> TYPE: PRT
<213> ORGANISM: Artificial Sequence
<220> FEATURE:
<223> OTHER INFORMATION: 2447_3C08 LCDR3

<400> SEQUENCE: 76

Asn Ser Arg Asp Ser Ser Gly Asn His Tyr Val
1               5                   10

<210> SEQ ID NO 77
<211> LENGTH: 124
<212> TYPE: PRT
<213> ORGANISM: Artificial Sequence
<220> FEATURE:
<223> OTHER INFORMATION: 2447_3C08 VH

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

-continued

```
Ala Lys Asp Arg Gly Ser Gly Tyr Glu Gly Asn Tyr Tyr Gly Met Asp
            100             105             110

Val Trp Gly Gln Gly Thr Leu Val Thr Val Ser Ser
        115                 120

<210> SEQ ID NO 78
<211> LENGTH: 108
<212> TYPE: PRT
<213> ORGANISM: Artificial Sequence
<220> FEATURE:
<223> OTHER INFORMATION: 2447_3C08 VL

<400> SEQUENCE: 78

Ser Tyr Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Thr
    50                  55                  60

Thr Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Tyr Val Phe Gly Thr Gly Thr Lys Val Thr Val Leu
            100                 105

<210> SEQ ID NO 79
<211> LENGTH: 247
<212> TYPE: PRT
<213> ORGANISM: Artificial Sequence
<220> FEATURE:
<223> OTHER INFORMATION: 2447_3C08 scFv

<400> SEQUENCE: 79

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Arg Gly Ser Gly Tyr Glu Gly Asn Tyr Tyr Gly Met Asp
            100             105             110

Val Trp Gly Gln Gly Thr Leu Val Thr Val Ser Ser Gly Gly Gly Gly
        115                 120                 125

Ser Gly Gly Gly Gly Ser Gly Gly Ala Ser Ser Tyr Glu Leu Thr
    130                 135                 140

Gln Asp Pro Ala Val Ser Val Ala Leu Gly Gln Thr Val Arg Ile Thr
145                 150                 155                 160

Cys Gln Gly Asp Ser Leu Arg Ser Tyr Tyr Ala Ser Trp Tyr Gln Gln
                165                 170                 175
```

-continued

Lys Pro Gly Gln Ala Pro Val Leu Val Ile Tyr Gly Lys Asn Asn Arg
          180                 185                 190

Pro Ser Gly Ile Pro Asp Arg Phe Ser Gly Thr Thr Ser Gly Asn Thr
          195                 200                 205

Ala Ser Leu Thr Ile Thr Gly Ala Gln Ala Glu Asp Glu Ala Asp Tyr
          210                 215                 220

Tyr Cys Asn Ser Arg Asp Ser Ser Gly Asn His Tyr Val Phe Gly Thr
225                 230                 235                 240

Gly Thr Lys Val Thr Val Leu
              245

<210> SEQ ID NO 80
<211> LENGTH: 741
<212> TYPE: DNA
<213> ORGANISM: Artificial Sequence
<220> FEATURE:
<223> OTHER INFORMATION: 2447_3C08 scFv

<400> SEQUENCE: 80
gaggtgcagc tgttggagtc tggggggaggc ttggtacagc ctggggggtc cctgagactc      60
tcctgtgcag cctctggatt cacctttgat gattatgcca tgcactgggt ccggcaagct     120
ccagggaagg gcctggagtg ggtctcaggt attagttgga atagtggtag cataggctat     180
gcggactctg tgaagggccg attcaccatc tccagagaca cgccaagaa ctccctgtat      240 ctgcaaatga acagtctgag agctgaggac acggccttgt attactgtgc aaaagatagg     300
ggtagtggct acgaaggaaa ctactacggt atggacgtct ggggccaagg aaccctggtc     360
accgtctcga gtggtggagg cggttcaggc ggaggtggct ctgcggtgg cgctagctcc     420 tatgagctga ctcaggaccc tgctgtgtct gtggccttgg gacagacagt caggatcaca     480
tgccaaggag acagcctcag aagctattat gcaagctggt accagcagaa gccaggacag     540
gcccctgtac ttgtcatcta tggtaaaaac aaccggccct cagggatccc agaccgattc     600
tctggtacca cctcaggaaa cacagcctcc ttgaccatca ctgggctca ggcggaagat      660 gaggctgact attactgtaa ctcccgggac agcagtggta accattatgt cttcggaact     720
gggaccaagg tcaccgtcct a                                                 741

<210> SEQ ID NO 81
<211> LENGTH: 8
<212> TYPE: PRT
<213> ORGANISM: Artificial Sequence
<220> FEATURE:
<223> OTHER INFORMATION: 2447_3H02 HCDR1

<400> SEQUENCE: 81

Gly Phe Thr Phe Asp Asp Tyr Ala
1                 5

<210> SEQ ID NO 82
<211> LENGTH: 8
<212> TYPE: PRT
<213> ORGANISM: Artificial Sequence
<220> FEATURE:
<223> OTHER INFORMATION: 2447_3H02 HCDR2

<400> SEQUENCE: 82

Ile Ser Trp Asp Ser Gly Ser Ile
1                 5

-continued

```
<210> SEQ ID NO 83
<211> LENGTH: 13
<212> TYPE: PRT
<213> ORGANISM: Artificial Sequence
<220> FEATURE:
<223> OTHER INFORMATION: 2447_3H02 HCDR3

<400> SEQUENCE: 83

Asp Val Ser Ser Gly Trp Tyr Trp Tyr Ala Phe Asp Ile
1               5                   10

<210> SEQ ID NO 84
<211> LENGTH: 6
<212> TYPE: PRT
<213> ORGANISM: Artificial Sequence
<220> FEATURE:
<223> OTHER INFORMATION: 2447_3H02 LCDR1

<400> SEQUENCE: 84

Ile Leu Arg Ser Tyr Tyr
1               5

<210> SEQ ID NO 85
<211> LENGTH: 3
<212> TYPE: PRT
<213> ORGANISM: Artificial Sequence
<220> FEATURE:
<223> OTHER INFORMATION: 2447_3H02 LCDR2

<400> SEQUENCE: 85

Gly Lys Asn
1

<210> SEQ ID NO 86
<211> LENGTH: 11
<212> TYPE: PRT
<213> ORGANISM: Artificial Sequence
<220> FEATURE:
<223> OTHER INFORMATION: 2447_3H02 LCDR3

<400> SEQUENCE: 86

Asn Ser Arg Asp Ser Ser Gly Asn Arg Val Val
1               5                   10

<210> SEQ ID NO 87
<211> LENGTH: 122
<212> TYPE: PRT
<213> ORGANISM: Artificial Sequence
<220> FEATURE:
<223> OTHER INFORMATION: 2447_3H02 VH

<400> SEQUENCE: 87

Glu Val Gln Leu Leu Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
            35                  40                  45

Ser Gly Ile Ser Trp Asp Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95
```

```
Ala Lys Asp Val Ser Ser Gly Trp Tyr Trp Tyr Ala Phe Asp Ile Trp
            100                 105                 110

Gly Gln Gly Thr Leu Val Thr Val Ser Ser
        115                 120
```

```
<210> SEQ ID NO 88
<211> LENGTH: 108
<212> TYPE: PRT
<213> ORGANISM: Artificial Sequence
<220> FEATURE:
<223> OTHER INFORMATION: 2447_3H02 VL

<400> SEQUENCE: 88

Ser Tyr Glu Leu Thr Gln Asp Pro Ala Val Ser Val Ala Leu Gly Gln
1               5                   10                  15

Thr Val Arg Ile Thr Cys Gln Gly Asp Ile Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Arg
                85                  90                  95

Val Val Phe Gly Gly Gly Thr Lys Leu Thr Val Leu
            100                 105
```

```
<210> SEQ ID NO 89
<211> LENGTH: 245
<212> TYPE: PRT
<213> ORGANISM: Artificial Sequence
<220> FEATURE:
<223> OTHER INFORMATION: 2447_3H02 scFv

<400> SEQUENCE: 89

Glu Val Gln Leu Leu Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asp Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Val Ser Ser Gly Trp Tyr Trp Tyr Ala Phe Asp Ile Trp
            100                 105                 110

Gly Gln Gly Thr Leu Val Thr Val Ser Ser Gly Gly Gly Ser Gly
        115                 120                 125

Gly Gly Gly Ser Gly Gly Gly Ala Ser Ser Tyr Glu Leu Thr Gln Asp
    130                 135                 140

Pro Ala Val Ser Val Ala Leu Gly Gln Thr Val Arg Ile Thr Cys Gln
145                 150                 155                 160

Gly Asp Ile Leu Arg Ser Tyr Tyr Ala Ser Trp Tyr Gln Gln Lys Pro
                165                 170                 175
```

```
Gly Gln Ala Pro Val Leu Val Ile Tyr Gly Lys Asn Asn Arg Pro Ser
            180                 185             190

Gly Ile Pro Asp Arg Phe Ser Gly Ser Ser Ser Gly Asn Thr Ala Ser
        195             200             205

Leu Thr Ile Thr Gly Ala Gln Ala Glu Asp Glu Ala Asp Tyr Tyr Cys
    210             215             220

Asn Ser Arg Asp Ser Ser Gly Asn Arg Val Val Phe Gly Gly Gly Thr
225                 230             235             240

Lys Leu Thr Val Leu
            245

<210> SEQ ID NO 90
<211> LENGTH: 735
<212> TYPE: DNA
<213> ORGANISM: Artificial Sequence
<220> FEATURE:
<223> OTHER INFORMATION: 2447_3H02 scFv

<400> SEQUENCE: 90
gaggtgcagc tgttggagtc tggggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaggt attagttggg atagtggtag cataggctat     180
gcggactctg tgaagggccg attcaccatc tccagagaca cgccaagaa ctccctgtat     240 ctgcaaatga acagtctgag agctgaggac acggccttgt attactgtgc aaaagatgtt     300
agcagtggct ggtactggta tgctttttgat atctgggggcc agggaaccct ggtcaccgtc     360
tcgagtggtg gaggcggttc aggcggaggt ggctctggcg gtggcgctag ctcctatgag     420
ctgactcagg accctgctgt gtctgtggcc ttgggacaga cagtcaggat cacatgccaa     480
ggagacatcc tcagaagtta ttatgcaagt tggtaccagc agaagccagg acaggcccct     540
gtacttgtca tttatggtaa aaacaaccgg ccctcaggga tcccagaccg attctctggc     600
tccagctcag gaaacacagc ttccttgacc atcactgggg ctcaggcgga agatgaggct     660
gactattact gtaactcccg ggacagcagt ggtaaccgtg tggtattcgg cggagggacc     720
aagctgaccg tccta                                                     735

<210> SEQ ID NO 91
<211> LENGTH: 8
<212> TYPE: PRT
<213> ORGANISM: Artificial Sequence
<220> FEATURE:
<223> OTHER INFORMATION: 2447_3H08 HCDR1

<400> SEQUENCE: 91

Gly Phe Thr Phe Asp Asp Tyr Ala
1               5

<210> SEQ ID NO 92
<211> LENGTH: 8
<212> TYPE: PRT
<213> ORGANISM: Artificial Sequence
<220> FEATURE:
<223> OTHER INFORMATION: 2447_3H08 HCDR2

<400> SEQUENCE: 92

Ile Ser Trp Asn Ser Gly Ser Ile
1               5
```

-continued

```
<210> SEQ ID NO 93
<211> LENGTH: 13
<212> TYPE: PRT
<213> ORGANISM: Artificial Sequence
<220> FEATURE:
<223> OTHER INFORMATION: 2447_3H08 HCDR3

<400> SEQUENCE: 93

Asp Arg Ser Ser Gly Trp Tyr Thr Gly Ser Phe Asp Tyr
1               5                   10

<210> SEQ ID NO 94
<211> LENGTH: 6
<212> TYPE: PRT
<213> ORGANISM: Artificial Sequence
<220> FEATURE:
<223> OTHER INFORMATION: 2447_3H08 LCDR1

<400> SEQUENCE: 94

Ser Leu Arg Ser Tyr Tyr
1               5

<210> SEQ ID NO 95
<211> LENGTH: 3
<212> TYPE: PRT
<213> ORGANISM: Artificial Sequence
<220> FEATURE:
<223> OTHER INFORMATION: 2447_3H08 LCDR2

<400> SEQUENCE: 95

Gly Lys Asn
1

<210> SEQ ID NO 96
<211> LENGTH: 11
<212> TYPE: PRT
<213> ORGANISM: Artificial Sequence
<220> FEATURE:
<223> OTHER INFORMATION: 2447_3H08 LCDR3

<400> SEQUENCE: 96

Gln Ser Arg Asp Ser Ser Asp Asn Arg Val Leu
1               5                   10

<210> SEQ ID NO 97
<211> LENGTH: 122
<212> TYPE: PRT
<213> ORGANISM: Artificial Sequence
<220> FEATURE:
<223> OTHER INFORMATION: 2447_3H08 VH

<400> SEQUENCE: 97

Glu Val Gln Leu Leu Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

-continued

Ala Arg Asp Arg Ser Ser Gly Trp Tyr Thr Gly Ser Phe Asp Tyr Trp
            100                 105                 110

Gly Gln Gly Thr Leu Val Thr Val Ser Ser
        115                 120

<210> SEQ ID NO 98
<211> LENGTH: 108
<212> TYPE: PRT
<213> ORGANISM: Artificial Sequence
<220> FEATURE:
<223> OTHER INFORMATION: 2447_3H08 VL

<400> SEQUENCE: 98

Ser Tyr Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Arg Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Ile Gly Ala Gln Ala Glu
65                  70                  75                  80

Asp Glu Ala Asp Tyr Tyr Cys Gln Ser Arg Asp Ser Ser Asp Asn Arg
                85                  90                  95

Val Leu Phe Gly Gly Gly Thr Lys Val Thr Val Leu
            100                 105

<210> SEQ ID NO 99
<211> LENGTH: 245
<212> TYPE: PRT
<213> ORGANISM: Artificial Sequence
<220> FEATURE:
<223> OTHER INFORMATION: 2447_3H08 scFv

<400> SEQUENCE: 99

Glu Val Gln Leu Leu Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ser Ser Gly Trp Tyr Thr Gly Ser Phe Asp Tyr Trp
            100                 105                 110

Gly Gln Gly Thr Leu Val Thr Val Ser Ser Gly Gly Gly Ser Gly
        115                 120                 125

Gly Gly Gly Ser Gly Gly Gly Ala Ser Ser Tyr Glu Leu Thr Gln Asp
    130                 135                 140

Pro Ala Val Ser Val Ala Leu Gly Gln Thr Val Arg Ile Thr Cys Gln
145                 150                 155                 160

Gly Asp Ser Leu Arg Ser Tyr Tyr Ala Ser Trp Tyr Arg Gln Lys Pro
                165                 170                 175

-continued

```
Gly Gln Ala Pro Val Leu Val Ile Tyr Gly Lys Asn Asn Arg Pro Ser
            180                     185                 190

Gly Ile Pro Asp Arg Phe Ser Gly Ser Ser Ser Gly Asn Thr Ala Ser
        195                 200                 205

Leu Thr Ile Ile Gly Ala Gln Ala Glu Asp Glu Ala Asp Tyr Tyr Cys
    210                 215                 220

Gln Ser Arg Asp Ser Ser Asp Asn Arg Val Leu Phe Gly Gly Gly Thr
225                 230                 235                 240

Lys Val Thr Val Leu
                245
```

```
<210> SEQ ID NO 100
<211> LENGTH: 735
<212> TYPE: DNA
<213> ORGANISM: Artificial Sequence
<220> FEATURE:
<223> OTHER INFORMATION: 2447_3H08 scFv

<400> SEQUENCE: 100
gaggtgcagc tgttggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaggt attagttgga atagtggtag catagactat     180
gcagactccg tgaagggccg attcaccatc tccagagaca attccaagaa cacgctgtat     240
ctgcaaatga acagcctgag agctgaggac acagctgtgt actactgtgc gagagatcgg     300
agtagtggct ggtacacggg gtcctttgac tactggggcc agggcaccct ggtcaccgtc     360
tcgagtggtg gaggcggttc aggcggaggt ggctctggcg gtggcgctag ctcctatgag     420
ctgactcagg accctgctgt gtctgtggcc ttgggacaga cagtcaggat cacatgccaa     480
ggagacagcc tcagaagcta ttatgcaagc tggtaccggc agaagccagg acaggcccct     540
gtacttgtca tctatggtaa aaacaaccgg ccctcaggga tcccagaccg attctctggc     600
tccagctcgg gaaacacagc ttccttgacc atcattgggg ctcaggcgga agacgaggct     660
gactattact gtcagtcccg ggacagcagt gataaccgtg ttctattcgg cggagggacc     720
aaggtcaccg tccta                                                      735
```

```
<210> SEQ ID NO 101
<211> LENGTH: 8
<212> TYPE: PRT
<213> ORGANISM: Artificial Sequence
<220> FEATURE:
<223> OTHER INFORMATION: G03 HCDR1

<400> SEQUENCE: 101

Gly Tyr Thr Phe Thr Ser Tyr Trp
1               5
```

```
<210> SEQ ID NO 102
<211> LENGTH: 8
<212> TYPE: PRT
<213> ORGANISM: Artificial Sequence
<220> FEATURE:
<223> OTHER INFORMATION: G03 HCDR2

<400> SEQUENCE: 102

Ile Asn Pro Gly Thr Gly Tyr Ile
1               5
```

```
<210> SEQ ID NO 103
<211> LENGTH: 7
<212> TYPE: PRT
<213> ORGANISM: Artificial Sequence
<220> FEATURE:
<223> OTHER INFORMATION: G03 HCDR3

<400> SEQUENCE: 103

Ser Thr Ala Pro Phe Asp Tyr
1               5

<210> SEQ ID NO 104
<211> LENGTH: 6
<212> TYPE: PRT
<213> ORGANISM: Artificial Sequence
<220> FEATURE:
<223> OTHER INFORMATION: G03 LCDR1

<400> SEQUENCE: 104

Gln Asp Ile Lys Ser Tyr
1               5

<210> SEQ ID NO 105
<211> LENGTH: 3
<212> TYPE: PRT
<213> ORGANISM: Artificial Sequence
<220> FEATURE:
<223> OTHER INFORMATION: G03 LCDR2

<400> SEQUENCE: 105

Tyr Ala Thr
1

<210> SEQ ID NO 106
<211> LENGTH: 9
<212> TYPE: PRT
<213> ORGANISM: Artificial Sequence
<220> FEATURE:
<223> OTHER INFORMATION: G03 LCDR3

<400> SEQUENCE: 106

Leu Gln Tyr Asp Glu Ser Pro Tyr Thr
1               5

<210> SEQ ID NO 107
<211> LENGTH: 116
<212> TYPE: PRT
<213> ORGANISM: Artificial Sequence
<220> FEATURE:
<223> OTHER INFORMATION: G03 VH

<400> SEQUENCE: 107

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met His Trp Val Gln Gln Ala Pro Gly Lys Gly Leu Glu Trp Ile
        35                  40                  45

Gly Tyr Ile Asn Pro Gly Thr Gly Tyr Ile Glu Tyr Asn Gln Lys Phe
    50                  55                  60

Lys Asp Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95
```

Ala Ser Ser Thr Ala Pro Phe Asp Tyr Trp Gly Gln Gly Thr Leu Val
            100                     105                     110

Thr Val Ser Ser
        115

<210> SEQ ID NO 108
<211> LENGTH: 107
<212> TYPE: PRT
<213> ORGANISM: Artificial Sequence
<220> FEATURE:
<223> OTHER INFORMATION: G03 VL

<400> SEQUENCE: 108

Glu Ile Val Leu Thr Gln Ser Pro Gly Thr Leu Ser Leu Ser Pro Gly
1               5                       10                      15

Glu Arg Ala Thr Leu Ser Cys Lys Ala Ser Gln Asp Ile Lys Ser Tyr
            20                      25                      30

Leu Ser Trp Tyr Gln Gln Lys Pro Gly Gln Ala Pro Arg Leu Leu Ile
        35                      40                      45

Tyr Tyr Ala Thr Arg Leu Ala Asp Gly Ile Pro Asp Arg Phe Ser Gly
    50                      55                      60

Ser Gly Ser Gly Thr Asp Phe Thr Leu Thr Ile Ser Arg Leu Glu Pro
65                      70                      75                      80

Glu Asp Phe Ala Val Tyr Tyr Cys Leu Gln Tyr Asp Glu Ser Pro Tyr
                85                      90                      95

Thr Phe Gly Gln Gly Thr Lys Leu Glu Ile Lys
            100                     105

<210> SEQ ID NO 109
<211> LENGTH: 238
<212> TYPE: PRT
<213> ORGANISM: Artificial Sequence
<220> FEATURE:
<223> OTHER INFORMATION: G03 scFv

<400> SEQUENCE: 109

Glu Val Gln Leu Val Gln Ser Gly Ala Glu Val Lys Lys Pro Gly Ala
1               5                       10                      15

Thr Val Lys Ile Ser Cys Lys Val Ser Gly Tyr Thr Phe Thr Ser Tyr
            20                      25                      30

Trp Met His Trp Val Gln Gln Ala Pro Gly Lys Gly Leu Glu Trp Ile
        35                      40                      45

Gly Tyr Ile Asn Pro Gly Thr Gly Tyr Ile Glu Tyr Asn Gln Lys Phe
    50                      55                      60

Lys Asp Arg Val Thr Ile Thr Ala Asp Lys Ser Thr Asp Thr Ala Tyr
65                      70                      75                      80

Met Glu Leu Ser Ser Leu Arg Ser Glu Asp Thr Ala Val Tyr Tyr Cys
                85                      90                      95

Ala Ser Ser Thr Ala Pro Phe Asp Tyr Trp Gly Gln Gly Thr Leu Val
            100                     105                     110

Thr Val Ser Ser Gly Gly Gly Ser Gly Gly Gly Gly Ser Gly Gly
        115                     120                     125

Gly Ala Ser Glu Ile Val Leu Thr Gln Ser Pro Gly Thr Leu Ser Leu
        130                     135                     140

Ser Pro Gly Glu Arg Ala Thr Leu Ser Cys Lys Ala Ser Gln Asp Ile
145                     150                     155                     160

Lys Ser Tyr Leu Ser Trp Tyr Gln Gln Lys Pro Gly Gln Ala Pro Arg
                165                     170                     175

```
Leu Leu Ile Tyr Tyr Ala Thr Arg Leu Ala Asp Gly Ile Pro Asp Arg
            180                 185                 190

Phe Ser Gly Ser Gly Ser Gly Thr Asp Phe Thr Leu Thr Ile Ser Arg
            195                 200                 205

Leu Glu Pro Glu Asp Phe Ala Val Tyr Tyr Cys Leu Gln Tyr Asp Glu
            210                 215                 220

Ser Pro Tyr Thr Phe Gly Gln Gly Thr Lys Leu Glu Ile Lys
225                 230                 235

<210> SEQ ID NO 110
<211> LENGTH: 113
<212> TYPE: PRT
<213> ORGANISM: Artificial Sequence
<220> FEATURE:
<223> OTHER INFORMATION: mucin 1

<400> SEQUENCE: 110

Ser Phe Phe Phe Leu Ser Phe His Ile Ser Asn Leu Gln Phe Asn Ser
1               5                   10                  15

Ser Leu Glu Asp Pro Ser Thr Asp Tyr Tyr Gln Glu Leu Gln Arg Asp
            20                  25                  30

Ile Ser Glu Met Phe Leu Gln Ile Tyr Lys Gln Gly Gly Phe Leu Gly
            35                  40                  45

Leu Ser Asn Ile Lys Phe Arg Pro Gly Ser Val Val Val Gln Leu Thr
            50                  55                  60

Leu Ala Phe Arg Glu Gly Thr Ile Asn Val His Asp Val Glu Thr Gln
65                  70                  75                  80

Phe Asn Gln Tyr Lys Thr Glu Ala Ala Ser Arg Tyr Asn Leu Thr Ile
                85                  90                  95

Ser Asp Val Ser Val Ser Asp Val Pro Phe Pro Phe Ser Ala Gln Ser
            100                 105                 110

Gly

<210> SEQ ID NO 111
<211> LENGTH: 182
<212> TYPE: PRT
<213> ORGANISM: Artificial Sequence
<220> FEATURE:
<223> OTHER INFORMATION: Synthetic_CD4

<400> SEQUENCE: 111

Thr Ser Ile Thr Ala Tyr Lys Ser Glu Gly Glu Ser Ala Glu Phe Ser
1               5                   10                  15

Phe Pro Leu Asn Leu Gly Glu Glu Ser Leu Gln Gly Glu Leu Arg Trp
            20                  25                  30

Lys Ala Glu Lys Ala Pro Ser Ser Gln Ser Trp Ile Thr Phe Ser Leu
            35                  40                  45

Lys Asn Gln Lys Val Ser Val Gln Lys Ser Thr Ser Asn Pro Lys Phe
            50                  55                  60

Gln Leu Ser Glu Thr Leu Pro Leu Thr Leu Gln Ile Pro Gln Val Ser
65                  70                  75                  80

Leu Gln Phe Ala Gly Ser Gly Asn Leu Thr Leu Thr Leu Asp Arg Gly
                85                  90                  95

Ile Leu Tyr Gln Glu Val Asn Leu Val Val Met Lys Val Thr Gln Pro
            100                 105                 110

Asp Ser Asn Thr Leu Thr Cys Glu Val Met Gly Pro Thr Ser Pro Lys
            115                 120                 125
```

```
Met Arg Leu Ile Leu Lys Gln Glu Asn Gln Glu Ala Arg Val Ser Arg
    130                 135                 140

Gln Glu Lys Val Ile Gln Val Gln Ala Pro Glu Ala Gly Val Trp Gln
145                 150                 155                 160

Cys Leu Leu Ser Glu Gly Glu Glu Val Lys Met Asp Ser Lys Ile Gln
                165                 170                 175

Val Leu Ser Lys Gly Leu
            180

<210> SEQ ID NO 112
<211> LENGTH: 135
<212> TYPE: DNA
<213> ORGANISM: Artificial Sequence
<220> FEATURE:
<223> OTHER INFORMATION: hinge domain

<400> SEQUENCE: 112
accacgacgc cagcgccgcg accaccaaca ccggcgccca ccatcgcgtc gcagcccctg     60
tccctgcgcc cagaggcgtg ccggccagcg gcggggggcg cagtgcacac gagggggctg    120
gacttcgcct gtgat                                                    135

<210> SEQ ID NO 113
<211> LENGTH: 81
<212> TYPE: DNA
<213> ORGANISM: Artificial Sequence
<220> FEATURE:
<223> OTHER INFORMATION: CD28 transmembrane domain

<400> SEQUENCE: 113
ttttgggtgc tggtggtggt tggtggagtc ctggcttgct atagcttgct agtaacagtg     60
gcctttatta ttttctgggt g                                               81

<210> SEQ ID NO 114
<211> LENGTH: 123
<212> TYPE: DNA
<213> ORGANISM: Artificial Sequence
<220> FEATURE:
<223> OTHER INFORMATION: CD28 costimulatory domain

<400> SEQUENCE: 114
aggagtaaga ggagcaggct cctgcacagt gactacatga acatgactcc ccgccgcccc     60
gggcccaccc gcaagcatta ccagccctat gccccaccac gcgacttcgc agcctatcgc    120
tcc                                                                  123

<210> SEQ ID NO 115
<211> LENGTH: 336
<212> TYPE: DNA
<213> ORGANISM: Artificial Sequence
<220> FEATURE:
<223> OTHER INFORMATION: CD3 zeta intracellular signaling domain

<400> SEQUENCE: 115
agagtgaagt tcagcaggag cgcagacgcc cccgcgtacc agcagggcca gaaccagctc     60
tataacgagc tcaatctagg acgaagagag gagtacgatg ttttggacaa gagacgtggc    120
cgggaccctg agatggggggg aaagccgaga aggaagaacc ctcaggaagg cctgtacaat    180
gaactgcaga agataagat ggcggaggcc tacagtgaga ttgggatgaa aggcgagcgc    240
cggaggggca gggggcacga tggcctttac cagggtctca gtacagccac caaggacacc    300
```

-continued

```
tacgacgccc ttcacatgca ggccctgccc cctcgc                                      336
```

```
<210> SEQ ID NO 116
<211> LENGTH: 15
<212> TYPE: PRT
<213> ORGANISM: Artificial Sequence
<220> FEATURE:
<223> OTHER INFORMATION: linker

<400> SEQUENCE: 116

Gly Gly Gly Gly Ser Gly Gly Gly Gly Ser Gly Gly Gly Ala Ser
1               5                   10                  15

<210> SEQ ID NO 117
<211> LENGTH: 4
<212> TYPE: PRT
<213> ORGANISM: Artificial Sequence
<220> FEATURE:
<223> OTHER INFORMATION: linker

<400> SEQUENCE: 117

Gly Gly Gly Ser
1

<210> SEQ ID NO 118
<211> LENGTH: 5
<212> TYPE: PRT
<213> ORGANISM: Artificial Sequence
<220> FEATURE:
<223> OTHER INFORMATION: linker

<400> SEQUENCE: 118

Gly Gly Gly Gly Ser
1               5

<210> SEQ ID NO 119
<211> LENGTH: 15
<212> TYPE: PRT
<213> ORGANISM: Artificial Sequence
<220> FEATURE:
<223> OTHER INFORMATION: linker

<400> SEQUENCE: 119

Gly Gly Gly Gly Ser Gly Gly Gly Gly Ser Gly Gly Gly Gly Ser
1               5                   10                  15

<210> SEQ ID NO 120
<211> LENGTH: 20
<212> TYPE: PRT
<213> ORGANISM: Artificial Sequence
<220> FEATURE:
<223> OTHER INFORMATION: linker

<400> SEQUENCE: 120

Gly Gly Gly Gly Ser Gly Gly Gly Gly Ser Gly Gly Gly Gly Ser Gly
1               5                   10                  15

Gly Gly Gly Ser
            20

<210> SEQ ID NO 121
<211> LENGTH: 20
<212> TYPE: PRT
<213> ORGANISM: Artificial Sequence
<220> FEATURE:
<223> OTHER INFORMATION: tandem repeats

<400> SEQUENCE: 121
```

-continued

```
His Gly Val Thr Ser Ala Pro Asp Thr Arg Pro Ala Pro Gly Ser Thr
1                 5                 10                15

Ala Pro Pro Ala
            20
```